US008263041B2

(12) United States Patent
Rybak et al.

(10) Patent No.: US 8,263,041 B2
(45) Date of Patent: Sep. 11, 2012

(54) ANTIGEN ASSOCIATED WITH THE NEOVASCULATURE OF TUMOUR METASTASES

(75) Inventors: Jascha Nikolai Rybak, Toronto (CA); Christoph Rosli, Dossenheim (DE); Alessandra Villa, Milan (IT); Giovanni Neri, Siena (IT); Dario Neri, Buchs (CH)

(73) Assignee: Philogen, S.p.A., Siena (IT)

( * ) Notice: Subject to any disclaimer, the term of this patent is extended or adjusted under 35 U.S.C. 154(b) by 0 days.

(21) Appl. No.: 12/593,872

(22) PCT Filed: Mar. 31, 2008

(86) PCT No.: PCT/IB2008/000965
§ 371 (c)(1),
(2), (4) Date: May 14, 2010

(87) PCT Pub. No.: WO2008/120101
PCT Pub. Date: Oct. 9, 2008

(65) Prior Publication Data
US 2010/0247541 A1 Sep. 30, 2010

Related U.S. Application Data

(60) Provisional application No. 60/909,580, filed on Apr. 2, 2007, provisional application No. 60/948,564, filed on Jul. 9, 2007.

(51) Int. Cl.
*A61K 49/00* (2006.01)
*A61K 39/44* (2006.01)
(52) U.S. Cl. .................... 424/9.1; 424/134.1; 424/178.1; 424/183.1
(58) Field of Classification Search ........................ None
See application file for complete search history.

(56) References Cited

U.S. PATENT DOCUMENTS

| 5,420,012 | A | 5/1995 | Partanen et al. | |
|---|---|---|---|---|
| 2006/0024724 | A1* | 2/2006 | Hussa et al. | 435/6 |
| 2006/0024757 | A1 | 2/2006 | Hussa et al. | |
| 2006/0115428 | A1 | 6/2006 | Menrad et al. | |

FOREIGN PATENT DOCUMENTS

| EP | 0 580 859 | 2/1994 |
|---|---|---|
| EP | 0603735 | 6/1994 |
| WO | WO 01/83816 | 11/2001 |
| WO | WO 2004/000216 | 12/2003 |
| WO | WO 2004/067038 | 8/2004 |
| WO | WO2004/094612 | 11/2004 |
| WO | WO 2005/009366 | 2/2005 |
| WO | WO 2005/086612 | 9/2005 |
| WO | WO 2006/026020 | 3/2006 |
| WO | WO 2006/050834 | 5/2006 |
| WO | WO 2007/128563 | 11/2007 |
| WO | WO 2008/120101 | 10/2008 |
| WO | WO 2009/013619 | 1/2009 |
| WO | WO 2009/056268 | 5/2009 |

OTHER PUBLICATIONS

Varma et al. Endometriosis and the neoplastic process. Reproduction (2004) 127 293-304.*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28.*
Brown et al. Tolerance of single, but not multiple, amino acid replacements in antibody VH CDR 2: a means of minimizing B cell wastage from somatic hypermutation? J. Immuno. May 1996, 3285-91.*
Paul, Fundamental Immunology, 3rd Edition, 1993, pp. 292-295.I.*
Rudikoff et al Single amino acid substitution altering antigen-binding specificity. Proc Natl Acad Sci U S A. Mar. 1982;79(6):1979-83.*
Chevalier et al., "Presence of ED-A Containing Fibronectin in Human Articular Cartilage from Patients with Osteoarthritis and Rheumatoid Arthritis," *The Journal of Rheumatology*, vol. 23, No. 6, pp. 1022-1030, 1996.
Claudepierre et al., "Increased Ed-B fibronectin plasma levels in spondyloarthropathies: comparison with rheumatoid arthritis patients and a healthy population," *Rheumatology*, vol. 38, No. 11, pp. 1099-1103, 1999.
Davies et al., "Affinity improvement of single antibody VH domains: residues in all three hypervariable regions affect antigen binding," *Immunotechnology*, vol. 2, pp. 169-179, 1996.
Holt et al., "Domain antibodies: proteins for therapy," *Trends in Biotechnology*, vol. 21, No. 11, pp. 484-490, 2003.
Kaspar et al., "Fibronectin as target for tumor therapy," *Int. J. Cancer*, vol. 118, pp. 1331-1339, 2006.
Kriegsmann et al., "Expression of fibronectin splice variants and oncofetal glycosylated fibronectin in the synovial membranes of patients with rheumatoid arthritis and osteoarthritis," *Rheumatol. Int.*, vol. 24, pp. 25-33, 2004.
Liao et al., "The EIIIA Segment of Fibronectin Is a Ligand for Integrins $\alpha_9\beta_1$ and $\alpha_4\beta_1$ Providing a Novel Mechanism for Regulating Cell Adhesion by Alternative Splicing," *Journal of Biological Chemistry*, vol. 277, No. 17, pp. 14467-14474, 2002.
Okamura et al., "The Extra Domain A of Fibronectin Activates Toll-like Receptor 4," *Journal of Biological Chemistry*, vol. 276, No. 13, pp. 10229-10233, 2001.
Oyama et al., "Oncodevelopmental regulation of the alternative splicing of fibronectin pre-messenger RNA in human lung tissues," *Cancer Research*, vol. 50, pp. 1075-1078, 1990.
Peters et al., "Preferential Recognition of a Fragment Species of Osteoarthritic Synovial Fluid Fibronectin by Antibodies to the Alternatively Spliced EIIIA Segment," *Arthritis and Rheumatism*, vol. 44, No. 11, pp. 2572-2585, 2001.
Schwager et al., "Preclinical characterization of DEKAVIL (F8-IL10), a novel clinical-stage immunocytokine which inhibits the progression of collagen-induced arthritis," *Arthritis and Research Therapy*, vol. 11, R142, 2009.
Trachsel et al., "Antibody-mediated delivery of IL-10 inhibits the progression of established collagen-induced arthritis," *Arthritis Research and Therapy*, vol. 9, No. 1, R9, 2007.

(Continued)

*Primary Examiner* — Maher Haddad
(74) *Attorney, Agent, or Firm* — Klarquist Sparkman, LLP.

(57) ABSTRACT

The invention relates to a binding member that binds the Extra Domain-A (ED-A) isoform of fibronectin for the treatment of tumor metastases.

11 Claims, 9 Drawing Sheets

OTHER PUBLICATIONS

Borsi et al., "Preparation of Phage Antibodies to the ED-A Domain of Human Fibronectin," *Experimental Cell Research*, 240:244-251, 1998.

Linnala et al., "Isoforms of cellular fibronectin and tenascin in amniotic fluid," *FEBS Letters*, 337(2):167-170, 1994.

Rybak et al., "The Extra-domain A of Fibronectin Is a Vascular Marker of Sold Tumors and Metastases," *Cancer Res.*, 67(22):10948-10957, 2007.

Scarpino et al., "Expression of EDA/EDB Isoforms of Fibronectin in Papillary Carcinoma of the Thyroid," *J. Pathol.*, 188:163-167, 1999.

Vartio et al., "Differential expression of the ED sequence-containing form of cellular fibronectin in embryonic and adult human tissues," *J. of Cell Sci.*, 88(4):419-430, 1987.

Villa et al., "A high-affinity human monoclonal antibody specific to the alternatively spliced EDA domain of fibronectin efficiently targets tumor neo-vasculature in vivo," *Int. J. Cancer*, 122:2405-2413, 2008.

Adams et al., "High Affinity Restricts the Localization and Tumor Penetration of Single-Chain Fv Antibody Molecules," *Cancer Research*, vol. 61, pp. 4750-4755, 2001.

Balza et al., "Transforming growth factor β regulates the levels of different fibronectin isoforms in normal cultured fibroblasts," *FEBS Letters*, vol. 228, No. 1, pp. 42-44, 1988.

Berndorff et al., "Imaging of Tumor Angiogenesis Using $^{99m}$Tc-Labeled Human Recombinant Anti-ED-B Fibronectin Antibody Fragments, " *J. Nucl. Med.*, vol. 47, pp. 1707-1716, 2006.

Berndorff et al., "Radioimmunotherapy of Solid Tumors by Targeting Extra Domain B Fibronectin: Identification of the Best-Suited Radioimmunoconjugate," *Clinical Cancer Research*, vol. 11, No. 19 Suppl., pp. 7053s-7063s, 2005.

Berndt et al., "Evidence of ED-B⁻ fibronectin synthesis in human tissues by non-radioactive RNA in situ hybridization. Investigations on carcinoma (oral squamous cell and breast carcinoma), chronic inflammation (rheumatoid synovitis) and fibromatosis (Morbus Dupuytren)," *Histochem. Cell Biol.*, vol. 109, pp. 249-255, 1998.

Berndt et al., "Differential expression of tenascin-C splicing domains in urothelial carcinomas of the urinary bladder," *J. Cancer Res. Clin. Oncol.*, vol. 132, pp. 537-546, 2006.

Birchler et al., "Infrared photodetection for the in vivo localisation of phage-derived antibodies directed against angiogenic markers," *Journal of Immunological Methods*, vol. 231, pp. 239-248, 1999.

Birchler et al., "Selective targeting and photocoagulation of ocular angiogenesis mediated by a phage-derived human antibody fragment," *Nature Biotechnology*, vol. 17, pp. 984-988, 1999.

Borsi et al., "Monoclonal Antibodies in the Analysis of Fibronectin Isoforms Generated by Alternative Splicing of mRNA Precursors in Normal and Transformed Human Cells," *Journal of Cell Biology*, vol. 104, pp. 595-600, 1987.

Borsi et al., "Expression of Different Tenascin Isoforms in Normal, Hyperplastic and Neoplastic Human Breast Tissues," *Int. J. Cancer*, vol. 52, pp. 688-692, 1992.

Borsi et al., "Transforming growth factor-β regulates the splicing pattern of fibronectin messenger RNA precursor," *FEBS Letters*, vol. 261, No. 1, pp. 175-178, 1990.

Borsi et al., "The Alternative Splicing Pattern of the Tenascin-C Pre-mRNA Is Controlled by the Extracellular pH," *Journal of Biological Chemistry*, vol. 270, No. 11, pp. 6243-6245, 1995.

Borsi et al., "Selective Targeting of Tumoral Vasculature: Comparison of Different Formats of an Antibody (L19) to the ED-B Domain of Fibronectin," *Int. J. Cancer*, vol. 102, pp. 75-85, 2002.

Brack et al., "Tumor-Targeting Properties of Novel Antibodies Specific to the Large Isoform of Tenascin-C," *Clinical Cancer Research*, vol. 12, No. 10, pp. 3200-3208, 2006.

Burrows et al., "Up-Regulation of Endoglin on Vascular Endothelial Cells in Human Solid Tumors: Implications for Diagnosis and Therapy," *Clinical Cancer Research*, vol. 1, pp. 1623-1634, 1995.

Carnemolla et al., "Identification of a Glioblastoma-Associated Tenascin-C Isoform by a High Affinity Recombinant Antibody," *American Journal of Pathology*, vol. 154, No. 5, pp. 1345-1352, 1999.

Carnemolla et al., "A Tumor-associated Fibronectin Isoform Generated by Alternative Splicing of Messenger RNA Precursors," *Journal of Cell Biology*, vol. 108, pp. 1139-1148, 1989.

Carnemolla et al., "Phage Antibodies with Pan-Species Recognition of the Oncofoetal Angiogenesis Marker Fibronectin ED-B Domain," *Int. J. Cancer*, vol. 68, pp. 397-405, 1996.

Carnemolla et al., "Enhancement of the antitumor properties of interleukin-2 by its targeted delivery to the tumor blood vessel extracellular matrix," *Blood*, vol. 99, No. 5, pp. 1659-1665, 2002.

Castellani et al., "Transformed Human Cells Release Different Fibronectin Variants Than Do Normal Cells," *Journal of Cell Biology*, vol. 103, pp. 1671-1677, 1986.

Castellani et al., "The Fibronectin Isoform Containing the ED-B Oncofetal Domain: A Marker of Angiogenesis," *Int. J. Cancer*, vol. 59, pp. 612-618, 1994.

Castronovo et al., "A Chemical Proteomics Approach for the Identification of Accessible Antigens Expressed in Human Kidney Cancer," *Molecular and Cellular Proteomics*, vol. 5, No. 11, pp. 2083-2091, 2006.

Demartis et al., "Selective targeting of tumour neovasculature by a radiohalogenated human antibody fragment specific for the ED-B domain of fibronectin," *Eur. J. Nucl. Med.*, vol. 28, pp. 534-539, 2001.

Fabbrini et al., "Selective occlusion of tumor blood vessels by targeted delivery of an antibody-photosensitizer conjugate," *Int. J. Cancer*, vol. 118, pp. 1805-1813, 2006.

Giovannoni et al., "Isolation of anti-angiogenesis antibodies from a large combinatorial repertoire by colony filter screening," *Nucleic Acids Research*, vol. 29, No. 5, p. e27 (1-6), 2001.

Hanahan et al., "The hallmarks of cancer," *Cell*, vol. 100, No. 1, pp. 57-70, 2000.

Luster et al., "Plasma Protein β-2-Glycoprotein 1 Mediates Interaction between the Anti-tumor Monoclonal Antibody 3G4 and Anionic Phospholipids on Endothelial Cells," *Journal of Biological Chemistry*, vol. 281, No. 40, pp. 29863-29871, 2006.

Mariani et al., "Tumor targeting potential of the monoclonal antibody BC-1 against oncofetal fibronectin in nude mice bearing human tumor implants," *Cancer*, vol. 80, No. S12, pp. 2378-2384, 1997.

Marlind et al., "Antibody-Mediated Delivery of Interleukin-2 to the Stroma of Breast Cancer Strongly Enhances the Potency of Chemotherapy," *Clin. Cancer Res.*, vol. 14, No. 20, pp. 6515-6524, 2008.

Menrad et al., "ED-B fibronectin as a target for antibody-based cancer treatments," *Expert Opinion Ther. Targets*, vol. 9, No. 3, pp. 491-500, 2005.

Neri et al., "Tumour Vascular Targeting," *Nature Rev. Cancer*, vol. 5, pp. 436-446, 2005.

Niesner et al., "Quantitation of the Tumor-Targeting Properties of Antibody Fragments Conjugated to Cell-Permeating HIV-1 TAT Peptides," *Bioconjugate Chem.*, vol. 13, pp. 729-736, 2002.

Nilsson et al., "Targeted Delivery of Tissue Factor to the ED-B Domain of Fibronectin, a Marker of Angiogenesis, Mediates the Infarction of Solid Tumors in Mice," *Cancer Research*, vol. 61, pp. 711-716, 2001.

Oyama et al., "Coordinate Oncodevelopmental Modulation of Alternative Splicing of Fibronectin Pre-Messenger RNA at ED-A, ED-B, and CS1 Regions in Human Liver Tumors," *Cancer Research*, vol. 35, pp. 2005-2011, 1993.

Oyama et al., "Deregulation of Alternative Splicing of Fibronectin Pre-mRNA in Malignant Human Liver Tumors," *Journal of Biological Chemistry*, vol. 264, No. 18, pp. 10331-10334, 1989.

Padro et al., "Increased angiogenesis in the bone marrow of patients with acute myeloid leukemia," *Blood*, vol. 95, No. 8, pp. 2637-2644, 2000.

Paganelli et al., "Pre-targeted immunodetection in glioma patients: tumour localization and single-photon emission tomography imaging of [$^{99m}$Tc]PnAO-biotin," *Eur. J. Nucl. Med.*, vol. 21, pp. 314-321, 1994.

Payne, "Progress in immunoconjugate cancer therapeutics," *Cancer Cell*, vol. 3, No. 3, pp. 207-212, 2003.

Riva et al., "Treatment of Intracranial Human Glioblastoma by Direct Intratumoral Administration of $^{131}$I-Labelled Anti-Tenascin Monoclonal Antibody BC-2," *Int. J. Cancer*, vol. 51, pp. 7-13, 1992.

Riva et al., "Local Treatment of Malignant Gliomas by Direct Infusion of Specific Monoclonal Antibodies Labeled with $^{131}$I: Comparison of the Results Obtained in Recurrent and Newly Diagnosed Tumors," *Cancer Research*, vol. 55, pp. 5952s-5956s, 1995.

Rybak et al., "Ligand-Based Vascular Targeting of Disease," *ChemMedChem*, vol. 2, pp. 22-40, 2007.

Santimaria et al., "Immunoscintigraphic Detection of the ED-B Domain of Fibronectin, a Marker of Angiogenesis, in Patients with Cancer," *Clinical Cancer Research*, vol. 9, pp. 571-579, 2003.

Schliemann et al., "Complete eradication of human B-cell lymphoma xenografts using rituximab in combination with the immunocytokine L19-IL2," *Blood*, vol. 113, pp. 2275-2283, 2009.

Schrama et al., "Antibody targeted drugs as cancer therapeutics," *Nature Rev. Drug Disc.*, vol. 5, pp. 147-159, 2006.

Silacci et al., "Human monoclonal antibodies to domain C of tenascin-C selectively target solid tumors in vivo," *Protein Engineering, Design & Selection*, vol. 19, No. 10, pp. 471-478, 2006.

Spaeth et al., "Radioimmunotherapy targeting the extra domain B of fibronectin in C6 rat gliomas: a preliminary study about the therapeutic efficacy of iodine-131-labeled SIP(L19)," *Nuclear Medicine and Biology*, vol. 33, pp. 661-666, 2006.

Tarli et al., "A High-Affinity Human Antibody That Targets Tumoral Blood Vessels," *Blood*, vol. 94, No. 1, pp. 192-198, 1999.

Thorpe, "Vascular Targeting Agents as Cancer Therapeutics," *Clinical Cancer Research*, vol. 10, pp. 415-427, 2004.

Think et al., "Radioimmunotherapy of Head and Neck Cancer Xenografts Using $^{131}$I-Labeled Antibody L19-SIP for Selective Targeting of Tumor Vasculature," *J. Nucl. Med.*, vol. 47, pp. 1127-1135, 2006.

Trachsel et al., "Antibodies for angiogenesis inhibition, vascular targeting and endothelial cell transcytosis," *Advanced Drug Delivery Reviews*, vol. 58, pp. 735-754, 2006.

Viti et al., "Increased Binding Affinity and Valence of Recombinant Antibody Fragments Lead to Improved Targeting of Tumoral Angiogenesis," *Cancer Research*, vol. 59, pp. 347-352, 1999.

Zardi et al., "Transformed human cells produce a new fibronectin isoform by preferential alternative splicing of a previously unobserved exon," *EMBO Journal*, vol. 6, No. 8, pp. 2337-2342, 1987.

Aguayo et al., "Angiogenesis in acute and chronic leukemias and myelodysplastic syndromes," *Blood*, vol. 96, No. 6, pp. 2240-2245, 2000.

Ballard et al., "Vascular tenascin-C regulates cardiac endothelial phenotype and neovascularization," *The FASEB Journal*, vol. 20, No. 6, pp. 717-719, 2006.

Chilosi et al., "Constitutive Expression of Tenascin in T-Dependent Zones of Human Lymphoid Tissues," *American Journal of Pathology*, vol. 143, No. 5, pp. 1348-1355, 1993.

El-Sorady et al., "Bone Marrow Angiogenesis in Patients with Hematological Malignancies: Role of VEGF," *Journal of the Egyptian Nat. Cancer Inst.*, vol. 12, No. 2, pp. 131-136, 2000.

Estey, "Modulation of angiogenesis in patients with myelodysplastic syndrome," *Best Practice & Research Clinical Haematology*, vol. 17, No. 4, pp. 623-639, 2004.

Schliemann et al., "Three clinical-stage tumor targeting antibodies reveal differential expression of oncofetal fibronectin and tenascin-C isoforms in human lymphoma," *Leukemia Research*, vol. 33, pp. 1718-1722, 2009.

Smolej and Kasparova, "Choice of endothelial marker is crucial for assessment of bone marrow microvessel density in chronic lymphocytic leukemia," *APMIS*, vol. 116, No. 12, pp. 1058-1062, 2008.

Soini et al., "Tenascin immunoreactivity in normal and pathological bone marrow," *Journal of Clinical Pathology*, vol. 46, No. 3, pp. 218-221, 1993.

Wang et al. "Identification of a Mutated Fibronectin As a Tumor Antigen Recognized by CD4$^+$T Cells: Its Role in Extracellular Matrix Formation and Tumor Metastasis," *The Journal of Experimental Medicine*, vol. 195, No. 11, pp. 1397-1406, 2002.

\* cited by examiner

Figure 2
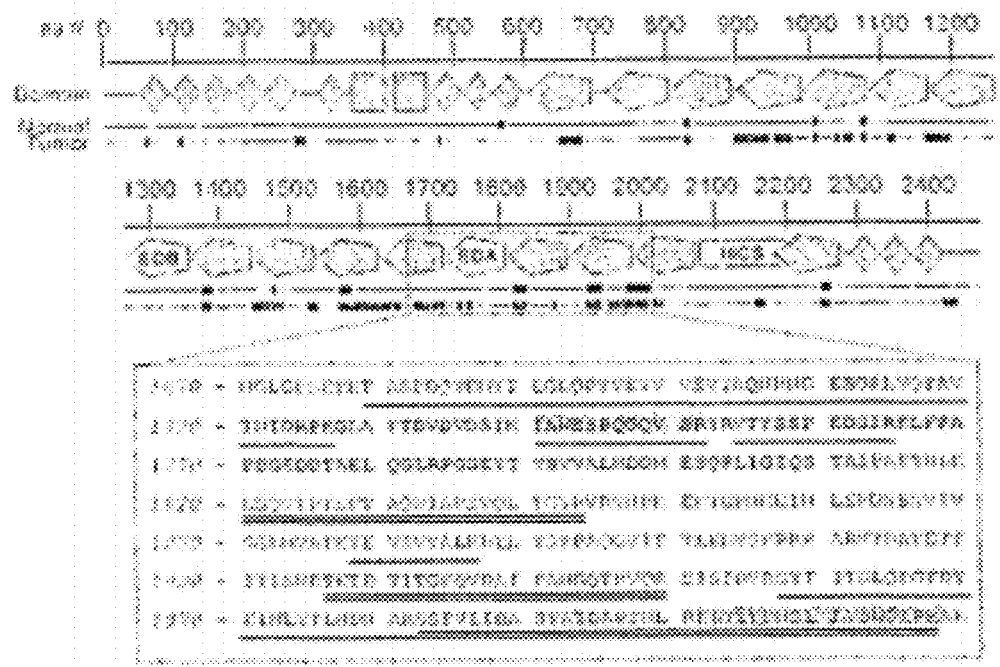
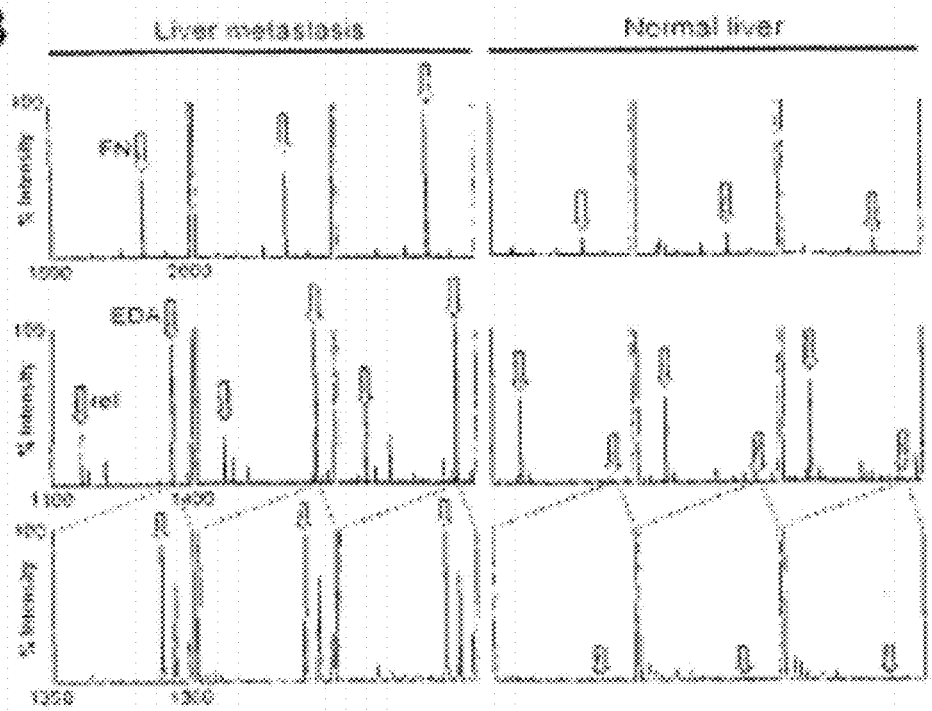

Figure 3
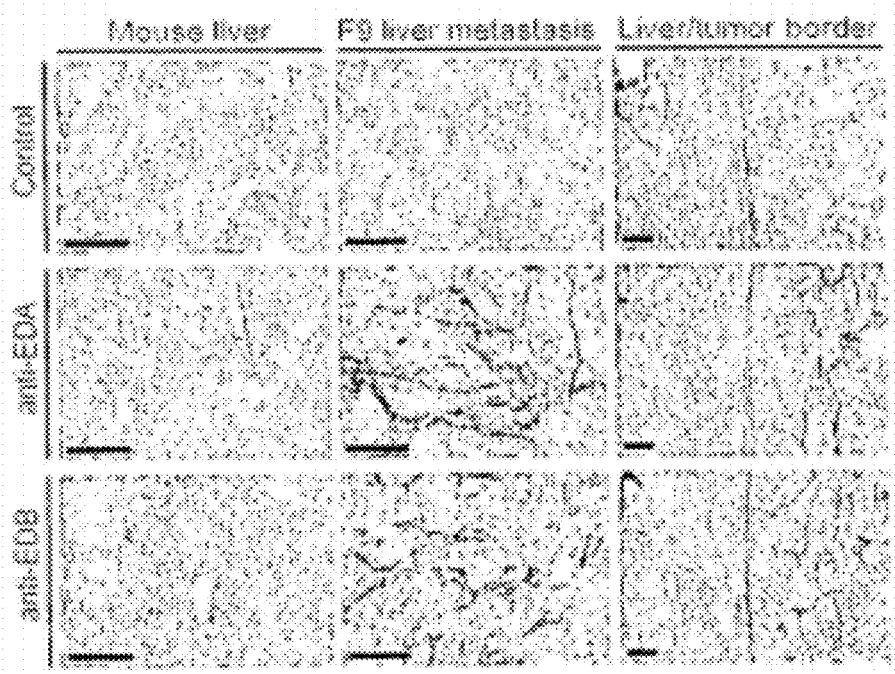
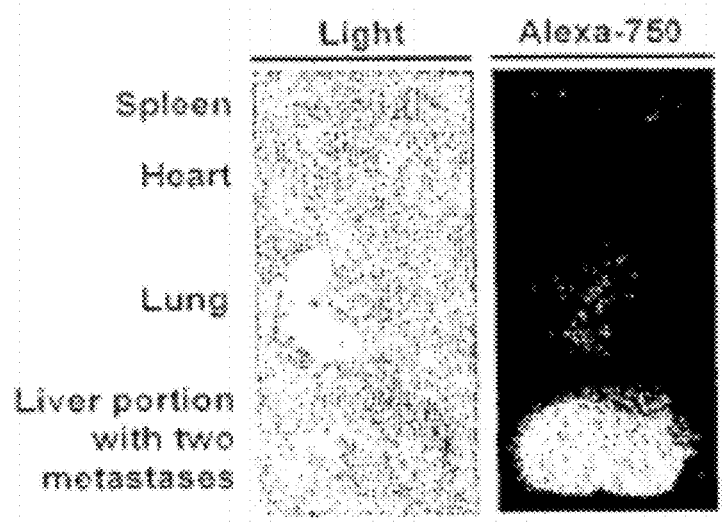

```
human  1  NIDRPKGLAFTDVDVDSIKIAWESPQGQVSRYRVTYSSPEDGIHELFPAPDGEEDTAELQ
          ************************************************ ********* ******
mouse  1  NIDRPKGLAFTDVDVDSIKIAWESPQGQVSRYRVTYSSPEDGIRELFPAPDGEDDTAELQ human  61 GLRPGSEYTVSVVALHDDMESQPLIGTQST
          *************************** *
mouse  61 GLRPGSEYTVSVVALHDDMESQPLIGIQST
```

GAGGTGCAGCTGGTGGAGTCTGGGGGAGGCTTGGTACAGCCTG
GGGGGTCCCTGAGACTCTCCTGTGCAGCCTCTGGATTCACCTT
TAGCCCGCGGAGGATGAGCTGGGTCCGCCAGGCTCCAGGGAAG
GGCTGGAGTGGGTCTCAGCTATTAGTGGTAGTGGTGGTAGCA
CATACTACGCAGACTCCGTGAAGGGCCGGTTCACCATCTCCAG
AGACAATTCCAAGAACACGCTGTATCTGCAAATGAACAGCCTG
AGAGCCGAGGACACGGCCGTATATTACTGTGCGAAAAGTACTC
ATTTGTATCTTTTTGACTACTGGGGCCAGGGAACCCTGGTCAC
CGTCTCGAGT

B

GGCGGTGGAGGTTCTGGCGGCGGTGGCAGTGGCGGTGGAGGTT
CCGGGGGTGGAGGATCT

GAAATTGTGTTGACGCAGTCTCCAGGCACCCTGTCTTTGTCTC
CAGGGGAAAAAGCCACCCTCTCCTGCAGGGCCAGTCAGAGTGT
TAGCTCTGCGTGGTTAGCCTGGTACCAGCAGAAACCTGGCCAG
GCTCCCAGGCTCCTCATCTATGGTGCATCCAGCAGGGCCACTG
GCATCCCAGACAGGTTCAGTGGCAGTGGGTCTGGGACAGACTT
CACTCTCACCATCAGCAGACTGGAGCCTGAAGATTTTGCAGTG
TATTACTGTCAGCAGATGCGTGGTCGGCCGCCGACGTTCGGCC
AAGGGACCAAGGTGGAAATCAAAGCGGCCGCAGAACAAAAACT
CATCTCAGAAGAGGATCTGAATGGGGCCGCATAGACTGTGAAA

EVQLVESGGGLVQPGGSLRLSCAASGFTFSPRRMSWVRQ
APGKGLEWVSAISGSGGSTYYADSVKGRFTISRDNSKNT
LYLQMNSLRAEDTAVYYCAKSTHLYLFDYWGQGTLVTVS
S

B

GGGGSGGGGSGGGGSGGGGS

C

EIVLTQSPGTLSLSPGERATLSCRASQSVSSAWLAWYQQ
KPGQAPRLLIYGASSRATGIPDRFSGSGSGTDFTLTISR
LEPEDFAVYYCQQMRGRPPTFGQGTKVEIKAAAEQKLIS
EEDLNGAA

Figure 7

SEQUENCE LISTING

<160> NUMBER OF SEQ ID NOS: 193

<210> SEQ ID NO 1
<211> LENGTH: 118
<212> TYPE: PRT
<213> ORGANISM: Artificial sequence
<220> FEATURE:
<223> OTHER INFORMATION: Synthetic sequence: Amino acid sequence of the anti-ED-A antibody H1 heavy chain (VH)

<400> SEQUENCE: 1

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Pro Arg
            20                  25                  30

Arg Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
            115
```

<210> SEQ ID NO 2
<211> LENGTH: 125
<212> TYPE: PRT
<213> ORGANISM: Artificial sequence
<220> FEATURE:
<223> OTHER INFORMATION: Synthetic sequence: Amino acid sequence of the anti-ED-A antibody H1 light chain (VL)

<400> SEQUENCE: 2

```
Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Ser Ala
            20                  25                  30

Trp Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
            50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
            115                 120                 125
```

<210> SEQ ID NO 3
<211> LENGTH: 3
<212> TYPE: PRT
<213> ORGANISM: Artificial sequence
<220> FEATURE:
<223> OTHER INFORMATION: Synthetic sequence: Amino acid sequence of the heavy chain CDR1 of anti-ED-A antibody H1

<400> SEQUENCE: 3

```
Pro Arg Arg
1
```

<210> SEQ ID NO 4
<211> LENGTH: 6
<212> TYPE: PRT
<213> ORGANISM: Artificial sequence
<220> FEATURE:

<223> OTHER INFORMATION: Synthetic sequence: Amino acid sequence of the
      heavy chain CDR2 of anti-ED-A antibody H1

<400> SEQUENCE: 4

Ser Gly Ser Gly Gly Ser
1               5

<210> SEQ ID NO 5
<211> LENGTH: 6
<212> TYPE: PRT
<213> ORGANISM: Artificial sequence
<220> FEATURE:
<223> OTHER INFORMATION: Synthetic sequence: Amino acid sequence of the
      heavy chain CDR3 of anti-ED-A antibody H1

<400> SEQUENCE: 5

Ser Thr His Leu Tyr Leu
1               5

<210> SEQ ID NO 6
<211> LENGTH: 3
<212> TYPE: PRT
<213> ORGANISM: Artificial sequence
<220> FEATURE:
<223> OTHER INFORMATION: Synthetic sequence: Amino acid sequence of the
      light chain CDR1 of anti-ED-A antibody H1

<400> SEQUENCE: 6

Ser Ala Trp
1

<210> SEQ ID NO 7
<211> LENGTH: 7
<212> TYPE: PRT
<213> ORGANISM: Artificial sequence
<220> FEATURE:
<223> OTHER INFORMATION: Synthetic sequence: Amino acid sequence of the
      light chain CDR2 of anti-ED-A antibody H1

<400> SEQUENCE: 7

Gly Ala Ser Ser Arg Ala Thr
1               5

<210> SEQ ID NO 8
<211> LENGTH: 6
<212> TYPE: PRT
<213> ORGANISM: Artificial sequence
<220> FEATURE:
<223> OTHER INFORMATION: Synthetic sequence: Amino acid sequence of the
      light chain CDR3 of anti-ED-A antibody H1

<400> SEQUENCE: 8

Met Arg Gly Arg Pro Pro
1               5

<210> SEQ ID NO 9

<400> SEQUENCE: 9

000

<210> SEQ ID NO 10

<400> SEQUENCE: 10

000

<210> SEQ ID NO 11

```
<211> LENGTH: 20
<212> TYPE: PRT
<213> ORGANISM: Artificial sequence
<220> FEATURE:
<223> OTHER INFORMATION: Synthetic sequence: Amino acid sequence of the
      anti-ED-A antibody H1 linker sequence

<400> SEQUENCE: 11

Gly Gly Gly Gly Ser Gly Gly Gly Ser Gly Gly Gly Gly Ser Gly
1               5                   10                  15

Gly Gly Gly Ser
            20

<210> SEQ ID NO 12
<211> LENGTH: 354
<212> TYPE: DNA
<213> ORGANISM: Artificial sequence
<220> FEATURE:
<223> OTHER INFORMATION: Synthetic sequence: Nucleotide sequence of the
      anti-ED-A antibody H1 heavy chain (VH)

<400> SEQUENCE: 12
gaggtgcagc tggtggagtc tgggggaggc ttggtacagc ctgggggtc cctgagactc        60 tcctgtgcag cctctggatt cacctttagc ccgcggagga tgagctgggt ccgccaggct      120
ccagggaagg gctggagtg gtctcagct attagtggta gtggtggtag cacatactac        180
gcagactccg tgaagggccg gttcaccatc tccagagaca attccaagaa cacgctgtat      240
ctgcaaatga acagcctgag agccgaggac acggccgtat attactgtgc gaaaagtact      300
catttgtatc tttttgacta ctggggccag ggaaccctgg tcaccgtctc gagt            354

<210> SEQ ID NO 13
<211> LENGTH: 387
<212> TYPE: DNA
<213> ORGANISM: Artificial sequence
<220> FEATURE:
<223> OTHER INFORMATION: Synthetic sequence: Nucleotide sequence of the
      anti-ED-A antibody H1 light chain (VL)

<400> SEQUENCE: 13
gaaattgtgt tgacgcagtc tccaggcacc ctgtctttgt ctccagggga aaaagccacc       60
ctctcctgca gggccagtca gagtgttagc tctgcgtggt tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagatgcgtg gtcggccgcc gacgttcggc     300
caagggacca aggtggaaat caaagcggcc gcagaacaaa aactcatctc agaagaggat     360
ctgaatgggg ccgcatagac tgtgaaa                                         387

<210> SEQ ID NO 14
<211> LENGTH: 60
<212> TYPE: DNA
<213> ORGANISM: Artificial sequence
<220> FEATURE:
<223> OTHER INFORMATION: Synthetic sequence: Nucleotide sequence of the
      anti-ED-A antibody H1 linker sequence

<400> SEQUENCE: 14
ggcggtggag gttctggcgg cggtggcagt ggcggtggag gttccggggg tggaggatct        60

<210> SEQ ID NO 15
<211> LENGTH: 17
<212> TYPE: PRT
```

<213> ORGANISM: Mus musculus

<400> SEQUENCE: 15

Phe Leu Thr Thr Thr Pro Asn Ser Leu Leu Val Ser Trp Gln Ala Pro
1               5                   10                  15

Arg

<210> SEQ ID NO 16
<211> LENGTH: 12
<212> TYPE: PRT
<213> ORGANISM: Mus musculus

<400> SEQUENCE: 16

Ile Ala Trp Glu Ser Pro Gln Gly Gln Val Ser Arg
1               5                   10

<210> SEQ ID NO 17
<211> LENGTH: 52
<212> TYPE: DNA
<213> ORGANISM: Artificial sequence
<220> FEATURE:
<223> OTHER INFORMATION: Synthetic sequence: Partially degenerate primer
<220> FEATURE:
<221> NAME/KEY: misc_feature
<222> LOCATION: 27, 28, 30, 31, 33, 34
<223> OTHER INFORMATION: n is a or g or c or t

<400> SEQUENCE: 17
ctggagcctg gcggacccag ctcatmnnmn nmnngctaaa ggtgaatcca ga        52

<210> SEQ ID NO 18
<211> LENGTH: 58
<212> TYPE: DNA
<213> ORGANISM: Artificial sequence
<220> FEATURE:
<223> OTHER INFORMATION: Synthetic sequence: Partially degenerate primer
<220> FEATURE:
<221> NAME/KEY: misc_feature
<222> LOCATION: 28, 29, 31, 32, 34, 35
<223> OTHER INFORMATION: n is a or g or c or t

<400> SEQUENCE: 18
ccaggtttct gctggtacca ggctaamnnm nnmnngctaa cactctgact ggccctgc    58

<210> SEQ ID NO 19
<211> LENGTH: 26
<212> TYPE: DNA
<213> ORGANISM: Artificial sequence
<220> FEATURE:
<223> OTHER INFORMATION: Synthetic sequence: Primer LMB3long

<400> SEQUENCE: 19
caggaaacag ctatgaccat gattac                                      26

<210> SEQ ID NO 20
<211> LENGTH: 30
<212> TYPE: DNA
<213> ORGANISM: Artificial sequence
<220> FEATURE:
<223> OTHER INFORMATION: Synthetic sequence: Primer fdseqlong

<400> SEQUENCE: 20
gacgttagta aatgaatttt ctgtatgagg                                  30

<210> SEQ ID NO 21
<211> LENGTH: 118
<212> TYPE: PRT

```
<213> ORGANISM: Artificial sequence
<220> FEATURE:
<223> OTHER INFORMATION: Synthetic sequence: Amino acid sequence of the
      anti-ED-A antibody B2 VH domain

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ala Ala
            20                  25                  30

Lys Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 22
<211> LENGTH: 125
<212> TYPE: PRT
<213> ORGANISM: Artificial sequence
<220> FEATURE:
<223> OTHER INFORMATION: Synthetic sequence: Amino acid sequence of the
      anti-ED-A antibody B2 VL domain

<400> SEQUENCE: 22

Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Val Ala
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 23
<211> LENGTH: 3
<212> TYPE: PRT
<213> ORGANISM: Artificial sequence
<220> FEATURE:
<223> OTHER INFORMATION: Synthetic sequence: Amino acid sequence of the
      heavy chain CDR1 of anti-ED-A antibody B2

<400> SEQUENCE: 23

Ala Ala Lys
1
```

<210> SEQ ID NO 24

<400> SEQUENCE: 24

000

<210> SEQ ID NO 25

<400> SEQUENCE: 25

000

<210> SEQ ID NO 26
<211> LENGTH: 3
<212> TYPE: PRT
<213> ORGANISM: Artificial sequence
<220> FEATURE:
<223> OTHER INFORMATION: Synthetic sequence: Amino acid sequence of the
      light chain CDR1 of anti-ED-A antibody B2

<400> SEQUENCE: 26

Val Ala Phe
1

<210> SEQ ID NO 27

<400> SEQUENCE: 27

000

<210> SEQ ID NO 28
<211> LENGTH: 5
<212> TYPE: PRT
<213> ORGANISM: Artificial sequence
<220> FEATURE:
<223> OTHER INFORMATION: Synthetic sequence: Linker sequence of F8
      diabody

<400> SEQUENCE: 28

Gly Ser Ser Gly Gly
1               5

<210> SEQ ID NO 29
<211> LENGTH: 15
<212> TYPE: DNA
<213> ORGANISM: Artificial sequence
<220> FEATURE:
<223> OTHER INFORMATION: Synthetic sequence: Linker sequence of F8
      diabody

<400> SEQUENCE: 29
gggtccagtg gcggt                                                    15

<210> SEQ ID NO 30

<400> SEQUENCE: 30

000

<210> SEQ ID NO 31
<211> LENGTH: 118
<212> TYPE: PRT
<213> ORGANISM: Artificial sequence
<220> FEATURE:
<223> OTHER INFORMATION: Synthetic sequence: Amino acid sequence of the
      anti-ED-A antibody G9 VH domain

<400> SEQUENCE: 31

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser His Met
                20                  25                  30

Gln Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
            115

<210> SEQ ID NO 32
<211> LENGTH: 125
<212> TYPE: PRT
<213> ORGANISM: Artificial sequence
<220> FEATURE:
<223> OTHER INFORMATION: Synthetic sequence: Amino acid sequence of the
      anti-ED-A antibody G9 VL domain

<400> SEQUENCE: 32

Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Thr Ala
                20                  25                  30

Phe Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
            115                 120                 125

<210> SEQ ID NO 33
<211> LENGTH: 3
<212> TYPE: PRT
<213> ORGANISM: Artificial sequence
<220> FEATURE:
<223> OTHER INFORMATION: Synthetic sequence: Amino acid sequence of the
      heavy chain CDR1 of anti-ED-A antibody G9

<400> SEQUENCE: 33

His Met Gln
1

<210> SEQ ID NO 34

<400> SEQUENCE: 34

000
```

```
<210> SEQ ID NO 35

<400> SEQUENCE: 35

000

<210> SEQ ID NO 36
<211> LENGTH: 3
<212> TYPE: PRT
<213> ORGANISM: Artificial sequence
<220> FEATURE:
<223> OTHER INFORMATION: Synthetic sequence: Amino acid sequence of the
      light chain CDR1 of anti-ED-A antibody G9

<400> SEQUENCE: 36

Thr Ala Phe
1

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41
<211> LENGTH: 118
<212> TYPE: PRT
<213> ORGANISM: Artificial sequence
<220> FEATURE:
<223> OTHER INFORMATION: Synthetic sequence: Amino acid sequence of the
      anti-ED-A antibody C5 VH domain

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Ile
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110
```

```
Leu Val Thr Val Ser Ser
        115

<210> SEQ ID NO 42
<211> LENGTH: 125
<212> TYPE: PRT
<213> ORGANISM: Artificial sequence
<220> FEATURE:
<223> OTHER INFORMATION: Synthetic sequence: Amino acid sequence of the
      anti-ED-A antibody C5 VL domain

<400> SEQUENCE: 42

Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Leu His
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 43
<211> LENGTH: 3
<212> TYPE: PRT
<213> ORGANISM: Artificial sequence
<220> FEATURE:
<223> OTHER INFORMATION: Synthetic sequence: Amino acid sequence of the
      heavy chain CDR1 of anti-ED-A antibody C5

<400> SEQUENCE: 43

Pro Ile Thr
1

<210> SEQ ID NO 44

<400> SEQUENCE: 44

000

<210> SEQ ID NO 45

<400> SEQUENCE: 45

000

<210> SEQ ID NO 46
<211> LENGTH: 3
<212> TYPE: PRT
<213> ORGANISM: Artificial sequence
<220> FEATURE:
<223> OTHER INFORMATION: Synthetic sequence: Amino acid sequence of the
      light chain CDR1 of anti-ED-A antibody C5

<400> SEQUENCE: 46

Leu His Phe
1
```

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51
<211> LENGTH: 118
<212> TYPE: PRT
<213> ORGANISM: Artificial sequence
<220> FEATURE:
<223> OTHER INFORMATION: Synthetic sequence: Amino acid sequence of the
      anti-ED-A antibody D5 VH domain

<400> SEQUENCE: 51

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Val Met
            20                  25                  30

Lys Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115
```

<210> SEQ ID NO 52
<211> LENGTH: 125
<212> TYPE: PRT
<213> ORGANISM: Artificial sequence
<220> FEATURE:
<223> OTHER INFORMATION: Synthetic sequence: Amino acid sequence of the
      anti-ED-A antibody D5 VL domain

<400> SEQUENCE: 52

```
Glu Ile Val Leu Thr Gln Ser Pro Gly Thr Leu Ser Leu Ser Pro Gly
 1               5                  10                  15

Glu Lys Ala Thr Leu Ser Cys Arg Ala Ser Gln Ser Val Ser Asn Ala
            20                  25                  30
```

```
Phe Leu Ala Trp Tyr Gln Gln Lys Pro Gly Gln Ala Pro Arg Leu Leu
            35                  40                  45
Ile Tyr Gly Ala Ser Ser Arg Ala Thr Gly Ile Pro Asp Arg Phe Ser
 50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Met Arg Gly Arg Pro
                 85                  90                  95
Pro Thr Phe Gly Gln Gly Thr Lys Val Glu Ile Lys Ala Ala Ala Glu
            100                 105                 110
Gln Lys Leu Ile Ser Glu Glu Asp Leu Asn Gly Ala Ala
            115                 120                 125
```

```
<210> SEQ ID NO 53
<211> LENGTH: 3
<212> TYPE: PRT
<213> ORGANISM: Artificial sequence
<220> FEATURE:
<223> OTHER INFORMATION: Synthetic sequence: Amino acid sequence of the
      heavy chain CDR1 of anti-ED-A antibody D5

<400> SEQUENCE: 53

Val Met Lys
1

<210> SEQ ID NO 54

<400> SEQUENCE: 54

000

<210> SEQ ID NO 55

<400> SEQUENCE: 55

000

<210> SEQ ID NO 56
<211> LENGTH: 3
<212> TYPE: PRT
<213> ORGANISM: Artificial sequence
<220> FEATURE:
<223> OTHER INFORMATION: Synthetic sequence: Amino acid sequence of the
      light chain CDR1 of anti-ED-A antibody D5

<400> SEQUENCE: 56

Asn Ala Phe
1

<210> SEQ ID NO 57

<400> SEQUENCE: 57

000

<210> SEQ ID NO 58

<400> SEQUENCE: 58

000

<210> SEQ ID NO 59

<400> SEQUENCE: 59
```

000

<210> SEQ ID NO 60

<400> SEQUENCE: 60

000

<210> SEQ ID NO 61
<211> LENGTH: 118
<212> TYPE: PRT
<213> ORGANISM: Artificial sequence
<220> FEATURE:
<223> OTHER INFORMATION: Synthetic sequence: Amino acid sequence of the
      anti-ED-A antibody E5 VH domain

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Gly
            20                  25                  30

Ser Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 62
<211> LENGTH: 125
<212> TYPE: PRT
<213> ORGANISM: Artificial sequence
<220> FEATURE:
<223> OTHER INFORMATION: Synthetic sequence: Amino acid sequence of the
      anti-ED-A antibody E5 VL domain

<400> SEQUENCE: 62

Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Leu Ala
            20                  25                  30

His Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

```
<210> SEQ ID NO 63
<211> LENGTH: 3
<212> TYPE: PRT
<213> ORGANISM: Artificial sequence
<220> FEATURE:
<223> OTHER INFORMATION: Synthetic sequence: Amino acid sequence of the
      heavy chain CDR1 of anti-ED-A antibody E5

<400> SEQUENCE: 63

Thr Gly Ser
1

<210> SEQ ID NO 64

<400> SEQUENCE: 64

000

<210> SEQ ID NO 65

<400> SEQUENCE: 65

000

<210> SEQ ID NO 66
<211> LENGTH: 3
<212> TYPE: PRT
<213> ORGANISM: Artificial sequence
<220> FEATURE:
<223> OTHER INFORMATION: Synthetic sequence: Amino acid sequence of the
      light chain CDR1 of anti-ED-A antibody E5

<400> SEQUENCE: 66

Leu Ala His
1

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71
<211> LENGTH: 118
<212> TYPE: PRT
<213> ORGANISM: Artificial sequence
<220> FEATURE:
<223> OTHER INFORMATION: Synthetic sequence: Amino acid sequence of the
      anti-ED-A antibody C8 VH domain

<400> SEQUENCE: 71
```

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Leu Gln
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
            115
```

```
<210> SEQ ID NO 72
<211> LENGTH: 125
<212> TYPE: PRT
<213> ORGANISM: Artificial sequence
<220> FEATURE:
<223> OTHER INFORMATION: Synthetic sequence: Amino acid sequence of the
      anti-ED-A antibody C8 VL domain

<400> SEQUENCE: 72
```

```
Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Leu Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
            115                 120                 125
```

```
<210> SEQ ID NO 73
<211> LENGTH: 3
<212> TYPE: PRT
<213> ORGANISM: Artificial sequence
<220> FEATURE:
<223> OTHER INFORMATION: Synthetic sequence: Amino acid sequence of the
      heavy chain CDR1 of anti-ED-A antibody C8

<400> SEQUENCE: 73

Leu Gln Thr
1
```

```
<210> SEQ ID NO 74

<400> SEQUENCE: 74

000
```

<210> SEQ ID NO 75

<400> SEQUENCE: 75

000

<210> SEQ ID NO 76
<211> LENGTH: 3
<212> TYPE: PRT
<213> ORGANISM: Artificial sequence
<220> FEATURE:
<223> OTHER INFORMATION: Synthetic sequence: Amino acid sequence of the
      light chain CDR1 of anti-ED-A antibody C8

<400> SEQUENCE: 76

Leu Pro Phe
1

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81
<211> LENGTH: 118
<212> TYPE: PRT
<213> ORGANISM: Artificial sequence
<220> FEATURE:
<223> OTHER INFORMATION: Synthetic sequence: Amino acid sequence of the
      anti-ED-A antibody F8 VH domain

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 82
<211> LENGTH: 125
<212> TYPE: PRT
<213> ORGANISM: Artificial sequence
<220> FEATURE:
<223> OTHER INFORMATION: Synthetic sequence: Amino acid sequence of the
      anti-ED-A antibody F8 VL domain

<400> SEQUENCE: 82

Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Met Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 83
<211> LENGTH: 3
<212> TYPE: PRT
<213> ORGANISM: Artificial sequence
<220> FEATURE:
<223> OTHER INFORMATION: Synthetic sequence: Amino acid sequence of the
      heavy chain CDR1 of anti-ED-A antibody F8

<400> SEQUENCE: 83

Leu Phe Thr
1

<210> SEQ ID NO 84

<400> SEQUENCE: 84

000

<210> SEQ ID NO 85

<400> SEQUENCE: 85

000

<210> SEQ ID NO 86
<211> LENGTH: 3
<212> TYPE: PRT
<213> ORGANISM: Artificial sequence
<220> FEATURE:
<223> OTHER INFORMATION: Synthetic sequence: Amino acid sequence of the
      light chain CDR1 of anti-ED-A antibody F8

<400> SEQUENCE: 86

Met Pro Phe
1

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91
<211> LENGTH: 118
<212> TYPE: PRT
<213> ORGANISM: Artificial sequence
<220> FEATURE:
<223> OTHER INFORMATION: Synthetic sequence: Amino acid sequence of the
      anti-ED-A antibody F1 VH domain

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gln Ala
            20                  25                  30

Arg Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 92
<211> LENGTH: 125
<212> TYPE: PRT
<213> ORGANISM: Artificial sequence
<220> FEATURE:
<223> OTHER INFORMATION: Synthetic sequence: Amino acid sequence of the
      anti-ED-A antibody F1 VL domain

<400> SEQUENCE: 92

Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Ala Pro
            20                  25                  30

```
Phe Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
                100                 105                 110

Gln Lys Leu Ile Ser Glu Glu Asp Leu Asn Gly Ala Ala
                115                 120                 125

<210> SEQ ID NO 93
<211> LENGTH: 3
<212> TYPE: PRT
<213> ORGANISM: Artificial sequence
<220> FEATURE:
<223> OTHER INFORMATION: Synthetic sequence: Amino acid sequence of the
      heavy chain CDR1 of anti-ED-A antibody F1

<400> SEQUENCE: 93

Gln Ala Arg
1

<210> SEQ ID NO 94

<400> SEQUENCE: 94

000

<210> SEQ ID NO 95

<400> SEQUENCE: 95

000

<210> SEQ ID NO 96
<211> LENGTH: 3
<212> TYPE: PRT
<213> ORGANISM: Artificial sequence
<220> FEATURE:
<223> OTHER INFORMATION: Synthetic sequence: Amino acid sequence of the
      light chain CDR1 of anti-ED-A antibody F1

<400> SEQUENCE: 96

Ala Pro Phe
1

<210> SEQ ID NO 97

<400> SEQUENCE: 97

000

<210> SEQ ID NO 98

<400> SEQUENCE: 98

000

<210> SEQ ID NO 99

<400> SEQUENCE: 99
```

000

<210> SEQ ID NO 100

<400> SEQUENCE: 100

000

<210> SEQ ID NO 101
<211> LENGTH: 118
<212> TYPE: PRT
<213> ORGANISM: Artificial sequence
<220> FEATURE:
<223> OTHER INFORMATION: Synthetic sequence: Amino acid sequence of the
      anti-ED-A antibody B7 VH domain

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Phe
            20                  25                  30

Asp Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 102
<211> LENGTH: 125
<212> TYPE: PRT
<213> ORGANISM: Artificial sequence
<220> FEATURE:
<223> OTHER INFORMATION: Synthetic sequence: Amino acid sequence of the
      anti-ED-A antibody B7 VL domain

<400> SEQUENCE: 102

Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Leu Ala
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

```
<210> SEQ ID NO 103
<211> LENGTH: 3
<212> TYPE: PRT
<213> ORGANISM: Artificial sequence
<220> FEATURE:
<223> OTHER INFORMATION: Synthetic sequence: Amino acid sequence of the
      heavy chain CDR1 of anti-ED-A antibody B7

<400> SEQUENCE: 103

His Phe Asp
1

<210> SEQ ID NO 104

<400> SEQUENCE: 104

000

<210> SEQ ID NO 105

<400> SEQUENCE: 105

000

<210> SEQ ID NO 106
<211> LENGTH: 3
<212> TYPE: PRT
<213> ORGANISM: Artificial sequence
<220> FEATURE:
<223> OTHER INFORMATION: Synthetic sequence: Amino acid sequence of the
      light chain CDR1 of anti-ED-A antibody B7

<400> SEQUENCE: 106

Leu Ala Phe
1

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111
<211> LENGTH: 118
<212> TYPE: PRT
<213> ORGANISM: Artificial sequence
<220> FEATURE:
<223> OTHER INFORMATION: Synthetic sequence: Amino acid sequence of the
      anti-ED-A antibody E8 VH domain

<400> SEQUENCE: 111
```

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Asp Met
            20                  25                  30

His Met Ser Trp Val Arg Gln Ala Pro Gly Lys Gly Leu Glu Trp Val
                35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
            115

<210> SEQ ID NO 112
<211> LENGTH: 125
<212> TYPE: PRT
<213> ORGANISM: Artificial sequence
<220> FEATURE:
<223> OTHER INFORMATION: Synthetic sequence: Amino acid sequence of the
      anti-ED-A antibody E8 VL domain

<400> SEQUENCE: 112

Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
            115                 120                 125

<210> SEQ ID NO 113
<211> LENGTH: 3
<212> TYPE: PRT
<213> ORGANISM: Artificial sequence
<220> FEATURE:
<223> OTHER INFORMATION: Synthetic sequence: Amino acid sequence of the
      heavy chain CDR1 of anti-ED-A antibody E8

<400> SEQUENCE: 113

Asp Met His
1

<210> SEQ ID NO 114

<400> SEQUENCE: 114

000
```

<210> SEQ ID NO 115

<400> SEQUENCE: 115

000

<210> SEQ ID NO 116
<211> LENGTH: 3
<212> TYPE: PRT
<213> ORGANISM: Artificial sequence
<220> FEATURE:
<223> OTHER INFORMATION: Synthetic sequence: Amino acid sequence of the
      light chain CDR1 of anti-ED-A antibody E8

<400> SEQUENCE: 116

Ser Ser Phe
1

<210> SEQ ID NO 117
<211> LENGTH: 350
<212> TYPE: PRT
<213> ORGANISM: Mus musculus

<400> SEQUENCE: 117

Asn Gly Leu Gly Pro Ser Lys Thr Lys Thr Ala Ser Pro Asp Gln Thr
1               5                   10                  15

Glu Met Thr Ile Glu Gly Leu Gln Pro Thr Val Glu Tyr Val Val Ser
            20                  25                  30

Val Tyr Ala Gln Asn Arg Asn Gly Glu Ser Gln Pro Leu Val Gln Thr
        35                  40                  45

Ala Val Thr Asn Ile Asp Arg Pro Lys Gly Leu Ala Phe Thr Asp Val
    50                  55                  60

Asp Val Asp Ser Ile Lys Ile Ala Trp Glu Ser Pro Gln Gly Gln Val
65                  70                  75                  80

Ser Arg Tyr Arg Val Thr Tyr Ser Ser Pro Glu Asp Gly Ile Arg Glu
                85                  90                  95

Leu Phe Pro Ala Pro Asp Gly Glu Asp Asp Thr Ala Glu Leu Gln Gly
            100                 105                 110

Leu Arg Pro Gly Ser Glu Tyr Thr Val Ser Val Val Ala Leu His Asp
        115                 120                 125

Asp Met Glu Ser Gln Pro Leu Ile Gly Ile Gln Ser Thr Ala Ile Pro
    130                 135                 140

Ala Pro Thr Asn Leu Lys Leu Ser Gln Val Thr Pro Thr Ser Phe Thr
145                 150                 155                 160

Ala Gln Trp Ile Ala Pro Ser Val Gln Leu Thr Gly Tyr Arg Val Arg
                165                 170                 175

Val Asn Pro Lys Glu Lys Thr Gly Pro Met Lys Glu Ile Asn Leu Ser
            180                 185                 190

Pro Asp Ser Ser Ser Val Ile Val Ser Gly Leu Met Val Ala Thr Lys
        195                 200                 205

Tyr Glu Val Ser Val Tyr Ala Leu Lys Asp Thr Leu Thr Ser Arg Pro
    210                 215                 220

Ala Gln Gly Val Ile Thr Thr Leu Glu Asn Val Ser Pro Pro Arg Arg
225                 230                 235                 240

Ala Arg Val Thr Asp Ala Thr Glu Thr Thr Ile Thr Ile Ser Trp Arg
                245                 250                 255

Thr Lys Thr Glu Thr Ile Thr Gly Phe Gln Val Asp Ala Ile Pro Ala
            260                 265                 270

```
Asn Gly Gln Thr Pro Val Gln Arg Ser Ile Ser Pro Asp Val Arg Ser
            275                 280                 285

Tyr Thr Ile Thr Gly Leu Gln Pro Gly Thr Asp Tyr Lys Ile His Leu
        290                 295                 300

Tyr Thr Leu Asn Asp Asn Ala Arg Ser Ser Pro Val Ile Ile Asp Ala
305                 310                 315                 320

Ser Thr Ala Ile Asp Ala Pro Ser Asn Leu Arg Phe Leu Thr Thr Thr
                325                 330                 335

Pro Asn Ser Leu Leu Val Ser Trp Gln Ala Pro Arg Ala Arg
            340                 345                 350
```

<210> SEQ ID NO 118
<211> LENGTH: 90
<212> TYPE: PRT
<213> ORGANISM: Homo sapiens

<400> SEQUENCE: 118

```
Asn Ile Asp Arg Pro Lys Gly Leu Ala Phe Thr Asp Val Asp Val Asp
1               5                   10                  15

Ser Ile Lys Ile Ala Trp Glu Ser Pro Gln Gly Gln Val Ser Arg Tyr
            20                  25                  30

Arg Val Thr Tyr Ser Ser Pro Glu Asp Gly Ile His Glu Leu Phe Pro
        35                  40                  45

Ala Pro Asp Gly Glu Glu Asp Thr Ala Glu Leu Gln Gly Leu Arg Pro
    50                  55                  60

Gly Ser Glu Tyr Thr Val Ser Val Val Ala Leu His Asp Asp Met Glu
65                  70                  75                  80

Ser Gln Pro Leu Ile Gly Thr Gln Ser Thr
            85                  90
```

<210> SEQ ID NO 119
<211> LENGTH: 90
<212> TYPE: PRT
<213> ORGANISM: Mus musculus

<400> SEQUENCE: 119

```
Asn Ile Asp Arg Pro Lys Gly Leu Ala Phe Thr Asp Val Asp Val Asp
1               5                   10                  15

Ser Ile Lys Ile Ala Trp Glu Ser Pro Gln Gly Gln Val Ser Arg Tyr
            20                  25                  30

Arg Val Thr Tyr Ser Ser Pro Glu Asp Gly Ile Arg Glu Leu Phe Pro
        35                  40                  45

Ala Pro Asp Gly Glu Asp Asp Thr Ala Glu Leu Gln Gly Leu Arg Pro
    50                  55                  60

Gly Ser Glu Tyr Thr Val Ser Val Val Ala Leu His Asp Asp Met Glu
65                  70                  75                  80

Ser Gln Pro Leu Ile Gly Ile Gln Ser Thr
            85                  90
```

<210> SEQ ID NO 120
<211> LENGTH: 288
<212> TYPE: PRT
<213> ORGANISM: Artificial sequence
<220> FEATURE:
<223> OTHER INFORMATION: Synthetic sequence: Antigen (11A12) containing
      the ED-A domain of human fibronectin

<400> SEQUENCE: 120

```
Met Arg Ser Tyr Arg Thr Glu Ile Asp Lys Pro Ser Gln Met Gln Val
1               5                   10                  15
```

Thr Asp Val Gln Asp Asn Ser Ile Ser Val Lys Trp Leu Pro Ser Ser
            20                  25                  30

Ser Pro Val Thr Gly Tyr Arg Val Thr Thr Pro Lys Asn Gly Pro
        35                  40                  45

Gly Pro Thr Lys Thr Lys Thr Ala Gly Pro Asp Gln Thr Glu Met Thr
    50                  55                  60

Ile Glu Gly Leu Gln Pro Thr Val Glu Tyr Val Val Ser Val Tyr Ala
65                  70                  75                  80

Gln Asn Pro Ser Gly Glu Ser Gln Pro Leu Val Gln Thr Ala Val Thr
                85                  90                  95

Asn Ile Asp Arg Pro Lys Gly Leu Ala Phe Thr Asp Val Asp Val Asp
            100                 105                 110

Ser Ile Lys Ile Ala Trp Glu Ser Pro Gln Gly Gln Val Ser Arg Tyr
        115                 120                 125

Arg Val Thr Tyr Ser Ser Pro Glu Asp Gly Ile His Glu Leu Phe Pro
    130                 135                 140

Ala Pro Asp Gly Glu Glu Asp Thr Ala Glu Leu Gln Gly Leu Arg Pro
145                 150                 155                 160

Gly Ser Glu Tyr Thr Val Ser Val Val Ala Leu His Asp Asp Met Glu
                165                 170                 175

Ser Gln Pro Leu Ile Gly Thr Gln Ser Thr Ala Ile Pro Ala Pro Thr
            180                 185                 190

Asp Leu Lys Phe Thr Gln Val Thr Pro Thr Ser Leu Ser Ala Gln Trp
        195                 200                 205

Thr Pro Pro Asn Val Gln Leu Thr Gly Tyr Arg Val Arg Val Thr Pro
    210                 215                 220

Lys Glu Lys Thr Gly Pro Met Lys Glu Ile Asn Leu Ala Pro Asp Ser
225                 230                 235                 240

Ser Ser Val Val Val Ser Gly Leu Met Val Ala Thr Lys Tyr Glu Val
                245                 250                 255

Ser Val Tyr Ala Leu Lys Asp Thr Leu Thr Ser Arg Pro Ala Gln Gly
            260                 265                 270

Val Val Thr Thr Leu Glu Asn Val Arg Ser His His His His His
        275                 280                 285

<210> SEQ ID NO 121
<211> LENGTH: 867
<212> TYPE: DNA
<213> ORGANISM: Artificial sequence
<220> FEATURE:
<223> OTHER INFORMATION: Synthetic sequence: Nucleotide sequence of
      antigen (11A12)

<400> SEQUENCE: 121
atgagatcct accgaacaga aattgacaaa ccatcccaga tgcaagtgac cgatgttcag      60
gacaacagca ttagtgtcaa gtggctgcct tcaagttccc ctgttactgg ttacagagta    120
accaccactc ccaaaaatgg accaggacca acaaaaacta aaactgcagg tccagatcaa    180
acagaaatga ctattgaagg cttgcagccc acagtggagt atgtggttag tgtctatgct    240
cagaatccaa gcggagagag tcagcctctg gttcagactg cagtaaccaa cattgatcgc    300
cctaaaggac tggcattcac tgatgtggat gtcgattcca tcaaaattgc ttgggaaagc    360
ccacaggggc aagtttccag gtacagggtg acctactcga gccctgagga tggaatccat    420
gagctattcc ctgcacctga tggtgaagaa gacactgcag agctgcaagg cctcagaccg    480
ggttctgagt acacagtcag tgtggttgcc ttgcacgatg atatggagag ccagcccctg    540

-continued

```
attggaaccc agtccacagc tattcctgca ccaactgacc tgaagttcac tcaggtcaca    600
cccacaagcc tgagcgccca gtggacacca cccaatgttc agctcactgg atatcgagtg    660
cgggtgaccc ccaaggagaa gaccggacca atgaaagaaa tcaaccttgc tcctgacagc    720
tcatccgtgg ttgtatcagg acttatggtg gccaccaaat atgaagtgag tgtctatgct    780
cttaaggaca ctttgacaag cagaccagct cagggagttg tcaccactct ggagaatgtc    840
agatctcatc accatcacca tcactaa                                         867

<210> SEQ ID NO 122
<211> LENGTH: 10
<212> TYPE: PRT
<213> ORGANISM: Mus musculus

<400> SEQUENCE: 122

His Tyr Gln Ile Asn Gln Gln Trp Glu Arg
1               5                   10

<210> SEQ ID NO 123
<211> LENGTH: 9
<212> TYPE: PRT
<213> ORGANISM: Mus musculus

<400> SEQUENCE: 123

Val Gly Asp Thr Tyr Glu Arg Pro Lys
1               5

<210> SEQ ID NO 124
<211> LENGTH: 17
<212> TYPE: PRT
<213> ORGANISM: Mus musculus

<400> SEQUENCE: 124

His Ala Leu Gln Ser Ala Ser Ala Gly Ser Gly Ser Phe Thr Asp Val
1               5                   10                  15

Arg

<210> SEQ ID NO 125
<211> LENGTH: 7
<212> TYPE: PRT
<213> ORGANISM: Mus musculus

<400> SEQUENCE: 125

Ile Gly Asp Gln Trp Asp Lys
1               5

<210> SEQ ID NO 126
<211> LENGTH: 11
<212> TYPE: PRT
<213> ORGANISM: Mus musculus

<400> SEQUENCE: 126

Thr Phe Tyr Gln Ile Gly Asp Ser Trp Glu Lys
1               5                   10

<210> SEQ ID NO 127
<211> LENGTH: 16
<212> TYPE: PRT
<213> ORGANISM: Mus musculus

<400> SEQUENCE: 127

Trp Lys Glu Ala Thr Ile Pro Gly His Leu Asn Ser Tyr Thr Ile Lys
1               5                   10                  15
```

<210> SEQ ID NO 128
<211> LENGTH: 14
<212> TYPE: PRT
<213> ORGANISM: Mus musculus

<400> SEQUENCE: 128

Glu Ala Thr Ile Pro Gly His Leu Asn Ser Tyr Thr Ile Lys
1               5                   10

<210> SEQ ID NO 129
<211> LENGTH: 21
<212> TYPE: PRT
<213> ORGANISM: Mus musculus

<400> SEQUENCE: 129

Gly Leu Thr Pro Gly Val Ile Tyr Glu Gly Gln Leu Ile Ser Ile Gln
1               5                   10                  15

Gln Tyr Gly His Arg
            20

<210> SEQ ID NO 130
<211> LENGTH: 12
<212> TYPE: PRT
<213> ORGANISM: Mus musculus

<400> SEQUENCE: 130

Trp Ser Arg Pro Gln Ala Pro Ile Thr Gly Tyr Arg
1               5                   10

<210> SEQ ID NO 131
<211> LENGTH: 19
<212> TYPE: PRT
<213> ORGANISM: Mus musculus

<400> SEQUENCE: 131

Ser Asp Asn Val Pro Pro Thr Asp Leu Gln Phe Val Glu Leu Thr
1               5                   10                  15

Asp Val Lys

<210> SEQ ID NO 132
<211> LENGTH: 16
<212> TYPE: PRT
<213> ORGANISM: Mus musculus

<400> SEQUENCE: 132

Val Thr Ile Met Trp Thr Pro Pro Asp Ser Val Val Ser Gly Tyr Arg
1               5                   10                  15

<210> SEQ ID NO 133
<211> LENGTH: 15
<212> TYPE: PRT
<213> ORGANISM: Mus musculus

<400> SEQUENCE: 133

Val Glu Val Leu Pro Val Ser Leu Pro Gly Glu His Gly Gln Arg
1               5                   10                  15

<210> SEQ ID NO 134
<211> LENGTH: 18
<212> TYPE: PRT
<213> ORGANISM: Mus musculus

<400> SEQUENCE: 134

Asn Thr Phe Ala Glu Ile Thr Gly Leu Ser Pro Gly Val Thr Tyr Leu
1               5                   10                  15

Phe Lys

<210> SEQ ID NO 135
<211> LENGTH: 8
<212> TYPE: PRT
<213> ORGANISM: Mus musculus

<400> SEQUENCE: 135

Val Phe Ala Val His Gln Gly Arg
1               5

<210> SEQ ID NO 136
<211> LENGTH: 10
<212> TYPE: PRT
<213> ORGANISM: Mus musculus

<400> SEQUENCE: 136

Thr Val Leu Val Thr Trp Thr Pro Pro Arg
1               5                   10

<210> SEQ ID NO 137
<211> LENGTH: 10
<212> TYPE: PRT
<213> ORGANISM: Mus musculus

<400> SEQUENCE: 137

Gln Tyr Asn Val Gly Pro Leu Ala Ser Lys
1               5                   10

<210> SEQ ID NO 138
<211> LENGTH: 16
<212> TYPE: PRT
<213> ORGANISM: Mus musculus

<400> SEQUENCE: 138

Asn Leu Gln Pro Gly Ser Glu Tyr Thr Val Thr Leu Val Ala Val Lys
1               5                   10                  15

<210> SEQ ID NO 139
<211> LENGTH: 12
<212> TYPE: PRT
<213> ORGANISM: Mus musculus

<400> SEQUENCE: 139

Ala Thr Gly Val Phe Thr Thr Leu Gln Pro Leu Arg
1               5                   10

<210> SEQ ID NO 140
<211> LENGTH: 13
<212> TYPE: PRT
<213> ORGANISM: Mus musculus

<400> SEQUENCE: 140

Leu Gly Val Arg Pro Ser Gln Gly Gly Glu Ala Pro Arg
1               5                   10

<210> SEQ ID NO 141
<211> LENGTH: 28
<212> TYPE: PRT
<213> ORGANISM: Mus musculus

<400> SEQUENCE: 141

Val Val Thr Pro Leu Ser Pro Pro Thr Asn Leu His Leu Glu Ala Asn

```
1               5                  10                  15

Pro Asp Thr Gly Val Leu Thr Val Ser Trp Glu Arg
                20                  25

<210> SEQ ID NO 142
<211> LENGTH: 10
<212> TYPE: PRT
<213> ORGANISM: Mus musculus

<400> SEQUENCE: 142

Ser Thr Thr Pro Asp Ile Thr Gly Tyr Arg
1               5                  10

<210> SEQ ID NO 143
<211> LENGTH: 17
<212> TYPE: PRT
<213> ORGANISM: Mus musculus

<400> SEQUENCE: 143

Val Thr Trp Ala Pro Pro Ser Ile Glu Leu Thr Asn Leu Leu Val
1               5                  10                  15

Arg

<210> SEQ ID NO 144
<211> LENGTH: 27
<212> TYPE: PRT
<213> ORGANISM: Mus musculus

<400> SEQUENCE: 144

Thr Gly Leu Asp Ser Pro Thr Gly Phe Asp Ser Ser Asp Ile Thr Ala
1               5                  10                  15

Asn Ser Phe Thr Val His Trp Val Ala Pro Arg
                20                  25

<210> SEQ ID NO 145
<211> LENGTH: 9
<212> TYPE: PRT
<213> ORGANISM: Mus musculus

<400> SEQUENCE: 145

Ala Pro Ile Thr Gly Tyr Ile Ile Arg
1               5

<210> SEQ ID NO 146
<211> LENGTH: 11
<212> TYPE: PRT
<213> ORGANISM: Mus musculus

<400> SEQUENCE: 146

His His Ala Glu His Ser Val Gly Arg Pro Arg
1               5                  10

<210> SEQ ID NO 147
<211> LENGTH: 18
<212> TYPE: PRT
<213> ORGANISM: Mus musculus

<400> SEQUENCE: 147

Glu Glu Ser Pro Pro Leu Ile Gly Gln Gln Ala Thr Val Ser Asp Ile
1               5                  10                  15

Pro Arg

<210> SEQ ID NO 148
```

```
<211> LENGTH: 21
<212> TYPE: PRT
<213> ORGANISM: Mus musculus

<400> SEQUENCE: 148

Ile Thr Tyr Gly Glu Thr Gly Gly Asn Ser Pro Val Gln Glu Phe Thr
1               5                   10                  15

Val Pro Gly Ser Lys
            20

<210> SEQ ID NO 149
<211> LENGTH: 12
<212> TYPE: PRT
<213> ORGANISM: Mus musculus

<400> SEQUENCE: 149

Ser Pro Val Gln Glu Phe Thr Val Pro Gly Ser Lys
1               5                   10

<210> SEQ ID NO 150
<211> LENGTH: 24
<212> TYPE: PRT
<213> ORGANISM: Mus musculus

<400> SEQUENCE: 150

Ser Thr Ala Thr Ile Asn Asn Ile Lys Pro Gly Ala Asp Tyr Thr Ile
1               5                   10                  15

Thr Leu Tyr Ala Val Thr Gly Arg
            20

<210> SEQ ID NO 151
<211> LENGTH: 15
<212> TYPE: PRT
<213> ORGANISM: Mus musculus

<400> SEQUENCE: 151

Gly Asp Ser Pro Ala Ser Ser Lys Pro Val Ser Ile Asn Tyr Lys
1               5                   10                  15

<210> SEQ ID NO 152
<211> LENGTH: 22
<212> TYPE: PRT
<213> ORGANISM: Mus musculus

<400> SEQUENCE: 152

Thr Glu Ile Asp Lys Pro Ser Gln Met Gln Val Thr Asp Val Gln Asp
1               5                   10                  15

Asn Ser Ile Ser Val Arg
            20

<210> SEQ ID NO 153
<211> LENGTH: 12
<212> TYPE: PRT
<213> ORGANISM: Mus musculus

<400> SEQUENCE: 153

Trp Leu Pro Ser Thr Ser Pro Val Thr Gly Tyr Arg
1               5                   10

<210> SEQ ID NO 154
<211> LENGTH: 29
<212> TYPE: PRT
<213> ORGANISM: Mus musculus

<400> SEQUENCE: 154
```

```
Thr Ala Ser Pro Asp Gln Thr Glu Met Thr Ile Glu Gly Leu Gln Pro
1               5                   10                  15

Thr Val Glu Tyr Val Val Ser Val Tyr Ala Gln Asn Arg
            20                  25
```

<210> SEQ ID NO 155
<211> LENGTH: 22
<212> TYPE: PRT
<213> ORGANISM: Mus musculus

<400> SEQUENCE: 155

```
Asn Gly Glu Ser Gln Pro Leu Val Gln Thr Ala Val Thr Thr Ile Pro
1               5                   10                  15

Ala Pro Thr Asn Leu Lys
            20
```

<210> SEQ ID NO 156
<211> LENGTH: 19
<212> TYPE: PRT
<213> ORGANISM: Mus musculus

<400> SEQUENCE: 156

```
Asn Gly Glu Ser Gln Pro Leu Val Gln Thr Ala Val Thr Asn Ile Asp
1               5                   10                  15

Arg Pro Lys
```

<210> SEQ ID NO 157
<211> LENGTH: 12
<212> TYPE: PRT
<213> ORGANISM: Mus musculus

<400> SEQUENCE: 157

```
Ile Ala Trp Glu Ser Pro Gln Gly Gln Val Ser Arg
1               5                   10
```

<210> SEQ ID NO 158
<211> LENGTH: 11
<212> TYPE: PRT
<213> ORGANISM: Mus musculus

<400> SEQUENCE: 158

```
Val Thr Tyr Ser Ser Pro Glu Asp Gly Ile Arg
1               5                   10
```

<210> SEQ ID NO 159
<211> LENGTH: 24
<212> TYPE: PRT
<213> ORGANISM: Mus musculus

<400> SEQUENCE: 159

```
Phe Ser Gln Val Thr Pro Thr Ser Phe Thr Ala Gln Trp Ile Ala Pro
1               5                   10                  15

Ser Val Gln Leu Thr Gly Tyr Arg
            20
```

<210> SEQ ID NO 160
<211> LENGTH: 9
<212> TYPE: PRT
<213> ORGANISM: Mus musculus

<400> SEQUENCE: 160

```
Tyr Glu Val Ser Val Tyr Ala Leu Lys
1               5
```

-continued

```
<210> SEQ ID NO 161
<211> LENGTH: 24
<212> TYPE: PRT
<213> ORGANISM: Mus musculus

<400> SEQUENCE: 161

Thr Lys Thr Glu Thr Ile Thr Gly Phe Gln Val Asp Ala Ile Pro Ala
1               5                   10                  15

Asn Gly Gln Thr Pro Val Gln Arg
            20

<210> SEQ ID NO 162
<211> LENGTH: 22
<212> TYPE: PRT
<213> ORGANISM: Mus musculus

<400> SEQUENCE: 162

Thr Glu Thr Ile Thr Gly Phe Gln Val Asp Ala Ile Pro Ala Asn Gly
1               5                   10                  15

Gln Thr Pro Val Gln Arg
            20

<210> SEQ ID NO 163
<211> LENGTH: 14
<212> TYPE: PRT
<213> ORGANISM: Mus musculus

<400> SEQUENCE: 163

Ser Tyr Thr Ile Thr Gly Leu Gln Pro Gly Thr Asp Tyr Lys
1               5                   10

<210> SEQ ID NO 164
<211> LENGTH: 11
<212> TYPE: PRT
<213> ORGANISM: Mus musculus

<400> SEQUENCE: 164

Ile His Leu Tyr Thr Leu Asn Asp Asn Ala Arg
1               5                   10

<210> SEQ ID NO 165
<211> LENGTH: 19
<212> TYPE: PRT
<213> ORGANISM: Mus musculus

<400> SEQUENCE: 165

Ser Ser Pro Val Ile Ile Asp Ala Ser Thr Ala Ile Asp Ala Pro Ser
1               5                   10                  15

Asn Leu Arg

<210> SEQ ID NO 166
<211> LENGTH: 17
<212> TYPE: PRT
<213> ORGANISM: Mus musculus

<400> SEQUENCE: 166

Phe Leu Thr Thr Thr Pro Asn Ser Leu Leu Val Ser Trp Gln Ala Pro
1               5                   10                  15

Arg

<210> SEQ ID NO 167
<211> LENGTH: 7
```

```
<212> TYPE: PRT
<213> ORGANISM: Mus musculus

<400> SEQUENCE: 167

Ile Thr Gly Tyr Ile Ile Lys
1               5

<210> SEQ ID NO 168
<211> LENGTH: 9
<212> TYPE: PRT
<213> ORGANISM: Mus musculus

<400> SEQUENCE: 168

Tyr Glu Lys Pro Gly Ser Pro Pro Arg
1               5

<210> SEQ ID NO 169
<211> LENGTH: 17
<212> TYPE: PRT
<213> ORGANISM: Mus musculus

<400> SEQUENCE: 169

Pro Tyr Leu Pro Asn Val Asp Glu Glu Val Gln Ile Gly His Val Pro
1               5                  10                  15

Arg

<210> SEQ ID NO 170
<211> LENGTH: 15
<212> TYPE: PRT
<213> ORGANISM: Mus musculus

<400> SEQUENCE: 170

Gly Val Thr Tyr Asn Ile Ile Val Glu Ala Leu Gln Asn Gln Arg
1               5                  10                  15

<210> SEQ ID NO 171
<211> LENGTH: 23
<212> TYPE: PRT
<213> ORGANISM: Mus musculus

<400> SEQUENCE: 171

Arg Pro Gly Ala Ala Glu Pro Ser Pro Asp Gly Thr Thr Gly His Thr
1               5                  10                  15

Tyr Asn Gln Tyr Thr Gln Arg
            20

<210> SEQ ID NO 172
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody H1

<400> SEQUENCE: 172

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Pro Arg
            20                  25                  30

Arg Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
            100                 105                 110

Leu Val Thr Val Ser Ser
            115

<210> SEQ ID NO 173
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody B2

<400> SEQUENCE: 173

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ala Ala
                 20                  25                  30

Lys Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
            100                 105                 110

Leu Val Thr Val Ser Ser
            115

<210> SEQ ID NO 174
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody C5

<400> SEQUENCE: 174

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Pro Ile
                 20                  25                  30

Thr Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
            100                 105                 110

Leu Val Thr Val Ser Ser
```

-continued

```
                115

<210> SEQ ID NO 175
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody D5

<400> SEQUENCE: 175

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Met
            20                  25                  30

Lys Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 176
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody E5

<400> SEQUENCE: 176

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Gly
            20                  25                  30

Ser Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 177
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody C8
```

-continued

<400> SEQUENCE: 177

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Gln
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 178
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody F8

<400> SEQUENCE: 178

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 179
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody F1

<400> SEQUENCE: 179

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Ala
            20                  25                  30

Arg Met Ser Trp Val Arg Gln Ala Pro Gly Lys Gly Leu Glu Trp Val

```
                35                  40                  45
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 180
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody B7

<400> SEQUENCE: 180

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser His Phe
            20                  25                  30

Asp Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 181
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody E8

<400> SEQUENCE: 181

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Met
            20                  25                  30

His Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95
```

-continued

Ala Lys Ser Thr His Leu Tyr Leu Phe Asp Tyr Trp Gly Gln Gly Thr
                100                 105                 110

Leu Val Thr Val Ser Ser
        115

<210> SEQ ID NO 182
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody G9

<400> SEQUENCE: 182

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Met
            20                  25                  30

Gln Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
                100                 105                 110

Leu Val Thr Val Ser Ser
        115

<210> SEQ ID NO 183
<211> LENGTH: 125
<212> TYPE: PRT
<213> ORGANISM: Artificial sequence
<220> FEATURE:
<223> OTHER INFORMATION: Synthetic sequence: VL domain of anti-ED-A
      antibody H1

<400> SEQUENCE: 183

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ala
            20                  25                  30

Trp Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
                100                 105                 110

Gln Lys Leu Ile Ser Glu Glu Asp Leu Asn Gly Ala Ala
            115                 120                 125

<210> SEQ ID NO 184
<211> LENGTH: 125

```
<212> TYPE: PRT
<213> ORGANISM: Artificial sequence
<220> FEATURE:
<223> OTHER INFORMATION: Synthetic sequence: VL domain of anti-ED-A
      antibody B2

<400> SEQUENCE: 184
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Val Ala
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

```
<210> SEQ ID NO 185
<211> LENGTH: 125
<212> TYPE: PRT
<213> ORGANISM: Artificial sequence
<220> FEATURE:
<223> OTHER INFORMATION: Synthetic sequence: VL domain of anti-ED-A
      antibody C5

<400> SEQUENCE: 185
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Leu His
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

```
<210> SEQ ID NO 186
<211> LENGTH: 125
<212> TYPE: PRT
<213> ORGANISM: Artificial sequence
<220> FEATURE:
<223> OTHER INFORMATION: Synthetic sequence: VL domain of anti-ED-A
      antibody D5

<400> SEQUENCE: 186
```

Glu Ile Val Leu Thr Gln Ser Pro Gly Thr Leu Ser Leu Ser Pro Gly
1               5                   10                  15

```
Glu Arg Ala Thr Leu Ser Cys Arg Ala Ser Gln Ser Val Ser Asn Ala
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 187
<211> LENGTH: 125
<212> TYPE: PRT
<213> ORGANISM: Artificial sequence
<220> FEATURE:
<223> OTHER INFORMATION: Synthetic sequence: VL domain of anti-ED-A
      antibody E5

<400> SEQUENCE: 187

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Leu Ala
            20                  25                  30

His Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 188
<211> LENGTH: 125
<212> TYPE: PRT
<213> ORGANISM: Artificial sequence
<220> FEATURE:
<223> OTHER INFORMATION: Synthetic sequence: VL domain of anti-ED-A
      antibody C8

<400> SEQUENCE: 188

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Leu Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
 50                  55                  60
```

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                 85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 189
<211> LENGTH: 125
<212> TYPE: PRT
<213> ORGANISM: Artificial sequence
<220> FEATURE:
<223> OTHER INFORMATION: Synthetic sequence: VL domain of anti-ED-A
      antibody F8

<400> SEQUENCE: 189

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Met Pro
                20                  25                  30

Phe Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                 85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 190
<211> LENGTH: 125
<212> TYPE: PRT
<213> ORGANISM: Artificial sequence
<220> FEATURE:
<223> OTHER INFORMATION: Synthetic sequence: VL domain of anti-ED-A
      antibody F1

<400> SEQUENCE: 190

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ala Pro
                20                  25                  30

Phe Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                 85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
```

```
                115                 120                 125

<210> SEQ ID NO 191
<211> LENGTH: 125
<212> TYPE: PRT
<213> ORGANISM: Artificial sequence
<220> FEATURE:
<223> OTHER INFORMATION: Synthetic sequence: VL domain of anti-ED-A
      antibody B7

<400> SEQUENCE: 191

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Leu Ala
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 192
<211> LENGTH: 125
<212> TYPE: PRT
<213> ORGANISM: Artificial sequence
<220> FEATURE:
<223> OTHER INFORMATION: Synthetic sequence: VL domain of anti-ED-A
      antibody E8

<400> SEQUENCE: 192

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 193
<211> LENGTH: 125
<212> TYPE: PRT
<213> ORGANISM: Artificial sequence
<220> FEATURE:
<223> OTHER INFORMATION: Synthetic sequence: VL domain of anti-ED-A
      antibody G9
```

<400> SEQUENCE: 193

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Thr Ala
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
            115                 120                 125
```

ANTIGEN ASSOCIATED WITH THE NEOVASCULATURE OF TUMOUR METASTASES

CROSS REFERENCE TO RELATED APPLICATIONS

This is the U.S. National Stage of International Application No. PCT/IB2008/000965, filed Mar. 31, 2008, which was published in English under PCT Article 21(2), which in turn claims the benefit of U.S. Provisional Application No. 60/909,580, filed Apr. 2, 2007 and U.S. Provisional Application No. 60/948,564, filed Jul. 9, 2007, which are incorporated by reference in their entirety.

The present invention relates to detection and treatment of metastases, i.e. detection and treatment of secondary tumours arising at a site that is distinct from a site of a primary tumour. The invention involves use of a binding member that binds the ED-A isoform of fibronectin, especially a binding member that binds domain ED-A of fibronectin.

The majority of cancer-related deaths are related to the metastatic spread of the disease (Hanahan and Weinberg 2000) and vigorous neovasculature is a characteristic feature of aggressive tumour metastases.

Tumours are classified as either benign or malignant. Malignant tumours are able to spread from the primary site (the primary tumour) to other parts of the body while benign tumours cannot spread. Malignant tumours can spread from their primary site by invasion and metastasis. Tumours formed as a result of metastasis are known, for example, as metastases, secondary tumours, metastatic lesions or metastatic foci.

Angiogenesis describes the growth of new blood vessels from existing blood vessels. Tumours can induce angiogenesis through secretion of various growth factors (e.g. Vascular Endothelial Growth Factor). Tumour angiogenesis allows tumours to grow beyond a few millimetres in diameter and is also a prerequisite for tumour metastasis. New blood vessels formed as the result of angiogenesis form the neovasculature of the tumour or the tumour metastases.

Fibronectin (FN) is a glycoprotein and is widely expressed in a variety of normal tissues and body fluids. It is a component of the extracellular matrix (ECM), and plays a role in many biological processes, including cellular adhesion, cellular migration, haemostasis, thrombosis, wound healing, tissue differentiation and oncogenic transformation.

Different FN isoforms are generated by alternative splicing of three regions (ED-A, ED-B, IIICS) of the primary transcript FN pre-mRNA, a process that is modulated by cytokines and extracellular pH (Balza 1988; Carnemolla 1989; Borsi 1990; Borsi 1995). Fibronectin contains two type-III globular extra-domains which may undergo alternative splicing: ED-A and ED-B (ffrench-Constant 1995, Hynes 1990, Kaspar et al. 2006). The ED-As of mouse fibronectin and human fibronectin are 96.7% identical (only 3 amino acids differ between the two 90 amino acid sequences, see FIG. 5).

Expression of the ED-A of fibronectin has been reported in tumour cells and in solid tumours at the mRNA level [see, e.g., (Jacobs et al. 2002, Matsumoto et al. 1999, Oyama et al. 1989, Tavian et al. 1994), at the level of isolated protein (Borsi et al. 1987) and at the immunohistochemical level (Borsi et al. 1998, Heikinheimo et al. 1991, Koukoulis et al. 1993, Koukoulis et al. 1995, Lohi et al. 1995, Scarpino et al. 1999). It has also been reported by Borsi et al., 1998, Exp Cell Res, 240, 244-251, that ED-A is present in the neo-vasculature of primary tumours. However no indication that ED-A is associated with the neo-vasculature of tumour metastases has previously been made.

We show herein that the ED-A of fibronectin is selectively expressed in the neovasculature of tumour metastases. As tumour blood vessels are readily accessible for intravenously-administered therapeutic agents (Neri and Bicknell 2005, Rybak et al. 2006, Thorpe 2004, Trachsel and Neri 2006), binding molecules such as antibody molecules that bind the A-FN and/or the ED-A of fibronectin represent novel agents which may be used for the preparation of a medicament for the treatment of the tumour metastases and/or tumour metastasis. The therapy of tumour neo-vasculature (tumour vascular targeting) is a promising approach for the treatment of tumour metastases. Tumour vascular targeting aims at disrupting the vasculature within the tumour itself, reducing blood flow to deprive the tumour of oxygen and nutrients, causing tumour cell death.

Provided herein are anti-ED-A antibodies which selectively recognize the new forming blood vessels of tumour metastases.

This invention in one aspect relates to the use of a binding member, e.g. an antibody molecule, that binds the Extra Domain-A (ED-A) isoform of fibronectin (A-FN), for the preparation of a medicament for the treatment of a tumour metastases and/or tumour metastasis. In another aspect the invention relates to the use of a binding member, e.g. an antibody molecule, that binds the ED-A of fibronectin for the preparation of a medicament for the treatment of tumour metastases and/or tumour metastasis.

In a further aspect, the invention relates to the use of a binding member, e.g. an antibody molecule, that binds the ED-A isoform of fibronectin for delivery, to the neovasculature of tumour metastases, of a molecule conjugated to the binding member. In another aspect, the invention relates to the use of a binding member, e.g. an antibody molecule, that binds the ED-A of fibronectin for delivery, to the neovasculature of tumour metastases, of a molecule conjugated to the binding member. In further aspects, the binding member may be used for the manufacture of a medicament for delivery of such a molecule.

In a yet further aspect, the invention relates to the use of a binding member, e.g. an antibody molecule, that binds the ED-A isoform of fibronectin for the manufacture of a diagnostic product for use in diagnosing a tumour metastases. In a yet further aspect, the invention relates to the use of a binding member, e.g. an antibody molecule, that binds the ED-A of fibronectin for the manufacture of a diagnostic product for use in diagnosing a tumour metastases.

The invention in one aspect also relates to a method of detecting or diagnosing a tumour metastases in a human or animal comprising the steps of:
(a) administering to the human or animal a binding member, e.g. an antibody molecule, which binds the ED-A isoform of fibronectin, and
(b) determining the presence or absence of the binding member at a site distant from a site currently or previously occupied by a primary tumour in the human or animal body;
wherein localisation of the binding member to a site distant from the site currently or previously occupied by the primary tumour in the human or animal indicates the presence of a tumour metastases.

The invention in another aspect relates to a method of detecting or diagnosing a tumour metastases in a human or animal comprising the steps of:

(a) administering to the human or animal a binding member, e.g. an antibody molecule, which binds the ED-A of fibronectin, and
(b) determining the presence or absence of the binding member at a site distant from a site currently or previously occupied by a primary tumour in the human or animal body;
wherein localisation of the binding member to a site distant from the site currently or previously occupied by the primary tumour in the human or animal indicates the presence of a tumour metastases.

The present invention also relates in one aspect to a method of treating a tumour metastases in an individual comprising administering to the individual a therapeutically effective amount of a medicament comprising a binding member, e.g. an antibody molecule, which binds the ED-A isoform of fibronectin. In another aspect, the present invention relates to a method of treating a tumour metastases in an individual comprising administering to the individual a therapeutically effective amount of a medicament comprising a binding member, e.g. an antibody molecule, which binds the ED-A of fibronectin.

In another aspect, the invention relates to a method of delivering a molecule to the neovasculature of tumour metastases in a human or animal comprising administering to the human or animal a binding member, e.g. an antibody molecule, which binds the ED-A isoform of fibronectin, wherein the binding member is conjugated to the molecule. In a further aspect, the invention relates to a method of delivering a molecule to the neovasculature of tumour metastases in a human or animal comprising administering to the human or animal a binding member, e.g. an antibody molecule which binds the ED-A of fibronectin, wherein the binding member is conjugated to the molecule.

The binding member of the invention may be an antibody which binds the ED-A isoform of fibronectin and/or the ED-A of fibronectin, comprising one or more complementarity determining regions (CDRs) of antibody H1, B2, C5, D5, E5, C8, F8, F1, B7, E8 or G9, or variants thereof. Preferably, a binding member of the invention is an antibody which binds the ED-A isoform of fibronectin and/or the ED-A of fibronectin, comprising one or more complementarity determining regions (CDRs) of antibody B2, C5, D5, C8, F8, B7 or G9, or variants thereof. Most preferably, a binding member of the invention is an antibody which binds the ED-A isoform of fibronectin and/or the ED-A of fibronectin, comprising one or more complementarity determining regions (CDRs) of antibody F8 or variants thereof.

The binding member of the invention may comprise a set of H and/or L CDRs of antibody H1, B2, C5, D5, E5, C8, F8, F1, B7, E8 or G9, or a set of H and/or L CDRs of antibody H1, B2, C5, D5, E5, C8, F8, F1, B7, E8 or G9 with ten or fewer, e.g. one, two, three, four, or five, amino acid substitutions within the disclosed set of H and/or L CDRs. Preferably, the binding member of the invention comprises a set of H and/or L CDRs of antibody B2, C5, D5, C8, F8, B7 or G9 with ten or fewer, e.g. one, two, three, four, or five, amino acid substitutions within the disclosed set of H and/or L CDRs. Preferably, The binding member of the invention comprises a set of H and/or L CDRs of antibody F8 with ten or fewer, e.g. one, two, three, four, or five, amino acid substitutions within the disclosed set of H and/or L CDRs.

Substitutions may potentially be made at any residue within the set of CDRs, and may be within CDR1, CDR2 and/or CDR3.

For example, a binding member of the invention may comprise one or more CDRs as described herein, e.g. a CDR3, and optionally also a CDR1 and CDR2 to form a set of CDRs.

A binding member of the invention may also comprise an antibody molecule, e.g. a human antibody molecule. The binding member normally comprises an antibody VH and/or VL domain. VH domains of binding members are also provided as part of the invention. Within each of the VH and VL domains are complementarity determining regions, ("CDRs"), and framework regions, ("FRs"). A VH domain comprises a set of HCDRs, and a VL domain comprises a set of LCDRs. An antibody molecule may comprise an antibody VH domain comprising a VH CDR1, CDR2 and CDR3 and a framework. It may alternatively or also comprise an antibody VL domain comprising a VL CDR1, CDR2 and CDR3 and a framework. The VH and VL domains and CDRs of antibodies H1, B2, C5, D5, E5, C8, F8, F1, B7, E8 and G9 are described herein. All VH and VL sequences, CDR sequences, sets of CDRs and sets of HCDRs and sets of LCDRs disclosed herein represent aspects and embodiments of a binding member for use in the invention. As described herein, a "set of CDRs" comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "set of CDRs" includes HCDRs and LCDRs.

A binding member of the invention may comprise an antibody VH domain comprising complementarity determining regions HCDR1, HCDR2 and HCDR3 and a framework, wherein HCDR1 is SEQ ID NO: 3, 23, 33, 43, 53, 63, 73, 83, 93, 103 or 113, and wherein optionally HCDR2 is SEQ ID NO: 4 and/or HCDR3 is SEQ ID NO: 5. Preferably, the HCDR1 is SEQ ID NO: 23, 33, 43, 53, 73, 83 or 103. Most preferably, the HCDR1 is SEQ ID NO: 83.

Typically, a VH domain is paired with a VL domain to provide an antibody antigen-binding site, although as discussed further below a VH or VL domain alone may be used to bind antigen. Thus, a binding member of the invention may further comprise an antibody VL domain comprising complementarity determining regions LCDR1, LCDR2 and LCDR3 and a framework, wherein LCDR1 is SEQ ID NO: 6, 26, 36, 46, 56, 66, 76, 86, 96, 106 or 116 and wherein optionally LCDR2 is SEQ ID NO: 7 and/or LCDR3 is SEQ ID NO: 8. Preferably, the LCDR1 is SEQ ID NO: 26, 36, 46, 56, 76, 86 or 106. Most preferably, the LCDR1 is SEQ ID NO: 86.

In one aspect the binding member of the invention is an isolated antibody molecule for the ED-A of fibronectin, comprising a VH domain and a VL domain, wherein the VH domain comprises a framework and a set of complementarity determining regions HCDR1, HCDR2 and HCDR3 and wherein the VL domain comprises complementarity determining regions LCDR1, LCDR2 and LCDR3 and a framework, and wherein
HCDR1 has amino acid sequence SEQ ID NO: 3, 23, 33, 43, 53, 63, 73, 83, 93, 103 or 113,
HCDR2 has amino acid sequence SEQ ID NO: 4,
HCDR3 has amino acid sequence SEQ ID NO: 5,
LCDR1 has amino acid sequence SEQ ID NO: 6, 26, 36, 46, 56, 66, 76, 86, 96, 106 or 116;
LCDR2 has amino acid sequence SEQ ID NO: 7; and
LCDR3 has amino acid sequence SEQ ID NO: 8.

One or more CDRs or a set of CDRs of an antibody may be grafted into a framework (e.g. human framework) to provide an antibody molecule for use in the invention. Framework regions may comprise human germline gene segment sequences. Thus, the framework may be germlined, whereby one or more residues within the framework are changed to match the residues at the equivalent position in the most similar human germline framework. A binding member of the invention may be an isolated antibody molecule having a VH domain comprising a set of HCDRs in a human germline framework, e.g. DP47. Normally the binding member also has a VL domain comprising a set of LCDRs, e.g. in a human germline framework. The human germline framework of the VL domain may be DPK22.

A VH domain of the invention may have amino acid sequence SEQ ID NO: 1, 21, 31, 41, 51, 61, 71, 81, 91, 101 or 111. Preferably, a VH domain of the invention has amino acid sequence SEQ ID NO: 21, 31, 41, 51, 71, 81 or 101. Most preferably, a VH domain of the invention has amino acid sequence SEQ ID NO: 81. A VL domain of the invention may have the amino acid SEQ ID NO: 2, 22, 32, 42, 52, 62, 72, 82, 92, 102 or 112. Preferably, a VL domain of the invention has amino acid SEQ ID NO: 22, 32, 42, 52, 72, 82 or 102. Most preferably, a VL domain of the invention has amino acid SEQ ID NO: 82.

A binding member of the invention may be a single chain Fv (scFv), comprising a VH domain and a VL domain joined via a peptide linker. The skilled person may select an appropriate length and sequence of linker, e.g. at least 5 or 10 amino acids in length, up to about 15, 20 or 25 amino acids in length. The scFv may consist of or comprise amino acid sequence SEQ ID NO: 9.

A binding member of the invention may be a diabody (WO94/13804; Holliger 1993a), which is a molecule comprising a first polypeptide with a VH domain and a VL domain joined via a peptide linker and a second polypeptide with a VH domain and a VL domain joined via a peptide linker wherein the VH domain and the VL domain of the first polypeptide pair with the VL domain and VH domain of the second polypeptide, respectively. The first and second polypeptides may be the same (whereby pairing results in a bivalent molecule) or different (whereby pairing results in a bispecific molecule). The skilled person may select an appropriate length and sequence of linker, e.g. 5 or fewer amino acids in length. The linker may have amino acid sequence SEQ ID NO: 28.

A binding member of the invention may comprise an antigen-binding site within a non-antibody molecule, normally provided by one or more CDRs e.g. a set of CDRs in a non-antibody protein scaffold. Binding members, including non-antibody and antibody molecules, are described in more detail elsewhere herein.

A binding member of the invention may be conjugated to a molecule that has biocidal or cytotoxic activity. Alternatively, a binding member of the invention may be conjugated to a radioisotope. As a further alternative, a binding member of the invention may be labelled with a detectable label.

These and other aspects of the invention are described in further detail below.

BRIEF DESCRIPTION OF THE DRAWINGS

FIG. 2 A: Shows the location of the fibronectin peptides identified in the proteomic analysis of normal mouse liver (Normal) and F9 liver metastases from mice (Tumor) on the fibronectin domain structure. The partial fibronectin amino acid sequence shown corresponds to SEQ ID NO: 117. B: The peptides identified in the proteomic analysis of normal mouse liver samples and F9 liver metastases from mice were submitted to an LC-MS/MS experiment. The peptides were first separated by HPLC and subsequently eluted in 192 fractions. Each fraction was spotted as a separate spot onto a MALDI target plate and MALDI TOF MS spectra were acquired of each fraction. Mass spectra of two different particular HPLC fractions (upper row and middle row, respectively) are shown for three replicate F9 mouse liver metastases samples (see panel labelled: "Liver metastasis") and three replicate samples of normal mouse liver (see panel labelled: "Normal liver"). The ion peak heights are normalized to the internal standard (see Materials and Methods) and thus allow a semi-quantitative comparison of corresponding peptides in the different samples. In the upper row, the peak indicated with an arrow (labelled "FN" in the first sample shown) corresponds to the peptide FLTTTPNSLLVSWQAPR (SEQ ID NO: 15) which derives from a constant region of fibronectin (fibronectin-type-III domain 16). The ion peak of this peptide is higher in the F9 mouse liver metastases samples (Liver metastasis) but is also present in the normal mouse liver samples (Normal liver), indicating that the fibronectin molecule is, in principle, present in both F9 mouse liver metastases and normal mouse liver but it seems to be more abundant in the F9 mouse liver metastases samples. In the middle row, the peak indicated with the right hand arrow (labelled "EDA") corresponds to the peptide IAWESPQGQVSR (SEQ ID NO: 16) which derives from the alternatively spliced extra-domain A of fibronectin. This ED-A peptide is only detectable in F9 mouse liver metastases samples (Liver metastasis) and not in the normal mouse liver samples (Normal liver). The reference peptide indicated with the left hand arrow (labelled "ref") was used to identify the HPLC fraction in which the ED-A peptide elutes. This means that the presence of the peak of the reference peptide in the spectra shown for the normal mouse liver samples (Normal liver) is proof that the mass spectra of the fractions in which the ED-A peptide would be detectable, if it was present in the normal mouse liver samples, is shown. The bottom row shows a close-up view of the mass spectra at the position of the ED-A peptide ion peak (indicated by the arrow) proving the absence of this peptide from the normal liver samples.

FIG. 3 A: Immunohistochemical staining (darker lines) of F9 liver metastases and adjacent normal mouse liver tissue with flag-tagged parent anti-ED-A antibody (anti-ED-A) revealed a strong vascular pattern of staining in the metastases, while no specific staining was detectable in adjacent normal liver tissue. In the negative controls (Control) the flag-tagged parent anti-ED-A antibody was omitted. The staining pattern observed with the flag-tagged parent anti-ED-A antibody is similar to the staining pattern observed with flag-tagged anti-ED-B scFv(L19) antibody (anti-EDB) which recognizes the fibronectin extra-domain B, a well established marker of neovascular structures. B: Shows the organs (spleen, heart, lung and a liver portion with two metastases) of Sv190 mice which were injected with F9DR tumour cells, and three weeks later were further injected in the tail vein with (200 µl/mouse, i.e. 60 µg antibody/mouse) Alexa 750-labelled parent anti-ED-A antibody (in a final concentration of 0.3 mg/ml). The mouse organs were excised six hours after injection of the Alexa 750-labelled parent anti-ED-A antibody. Alexa 750-labelled parent anti-ED-A antibody staining was visualized using a home-built infrared fluorescent imager (Birchler et al. 1999) equipped with a tungsten halogen lamp, excitation and emission filters specific for Alexa 750, and a monochrome CCD camera.

FIG. 5: Shows an alignment between the human ED-A (top sequence; SEQ ID NO: 118) and the mouse ED-A (bottom sequence; SEQ ID NO: 119). The asterisks indicate the amino acid positions where the amino acids of the human ED-A and the mouse ED-A are identical.

FIG. 6 A: Shows the nucleotide sequence of the anti-ED-A antibody H1 heavy chain (VH) (SEQ ID NO: 12). The nucleotide sequence of the heavy chain CDR1 of anti-ED-A antibody H1 is underlined. The nucleotide sequence of the heavy chain CDR2 of the anti-ED-A antibody H1 is shown in italics and underlined. The nucleotide sequence of the heavy chain CDR3 of anti-ED-A antibody H1 is shown in bold and underlined. B: Shows the nucleotide sequence of the anti-ED-A antibody H1 linker sequence (SEQ ID NO: 14). C: Shows the nucleotide sequence of the anti-ED-A antibody H1 light chain (VL) (SEQ ID NO: 13). The nucleotide sequence of the light chain CDR1 of anti-ED-A antibody H1 is underlined. The nucleotide sequence of the light chain CDR2 of the anti-ED-A antibody H1 is shown in italics and underlined. The nucleotide sequence of the light chain CDR3 of anti-ED-A antibody H1 is shown in bold and underlined.

FIG. 7 A: Shows the amino acid sequence of the anti-ED-A antibody H1 heavy chain (VH) (SEQ ID NO: 1). The amino acid sequence of the heavy chain CDR1 (SEQ ID NO: 3) of anti-ED-A antibody H1 is underlined. The amino acid sequence of the heavy chain CDR2 (SEQ ID NO: 4) of the anti-ED-A antibody H1 is shown in italics and underlined. The amino acid sequence of the heavy chain CDR3 (SEQ ID NO: 5) of anti-ED-A antibody H1 is shown in bold and underlined. B: Shows the amino acid sequence of the anti-ED-A antibody H1 linker sequence (SEQ ID NO: 11). C: Shows the amino acid sequence of the anti-ED-A antibody H1 light chain (VL) (SEQ ID NO: 2). The amino acid sequence of the light chain CDR1 (SEQ ID NO: 6) of anti-ED-A antibody H1 is underlined. The amino acid sequence of the light chain CDR2 (SEQ ID NO: 7) of the anti-ED-A antibody H1 is shown in italics and underlined. The amino acid sequence of the light chain CDR3 (SEQ ID NO: 8) of anti-ED-A antibody H1 is shown in bold and underlined.

TERMINOLOGY

Fibronectin

Figure 1:
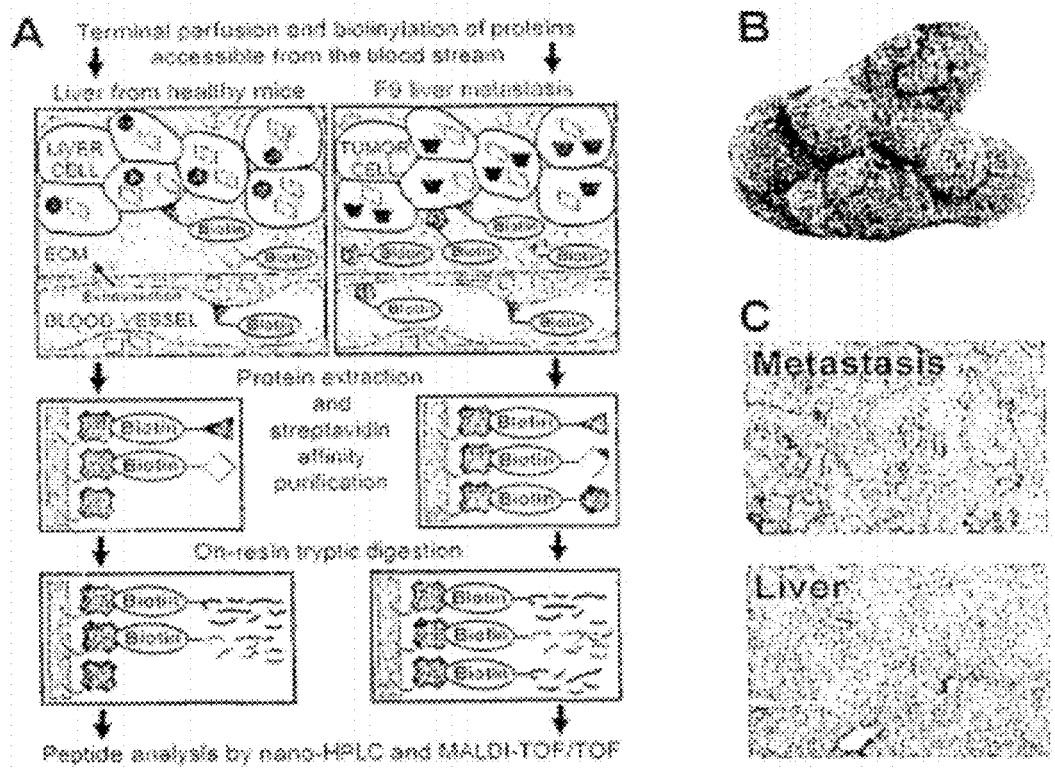
FIG. 1A: Shows a schematic representation of the perfusion based proteomic methodology used for the comparative analysis of accessible proteins in liver from healthy mice and F9 liver metastases from mice. B: Shows the large metastatic foci developed by F9 liver metastases. C: Shows the selective and efficient staining of the blood vessels of F9 liver metastases (Metastasis) as well as the strong staining of the blood vessels and labelling of some sinusoids in normal liver (Liver). Staining corresponds to darker lines and it is obtained after tumour-bearing mice were perfused with 15 ml of a 1.8 mM solution of sulfosuccinimidyl-6-[biotin-amido]hexanoate (1 mg/ml) in PBS, pH 7.4, supplemented with 10% Dextran-40 as plasma expander under terminal anaesthesia followed by histochemical staining with a streptavidin-alkaline phosphatase conjugate.

Fibronectin is an antigen subject to alternative splicing, and a number of alternative isoforms of fibronectin are known, as described elsewhere herein. Extra Domain-A (EDA or ED-A) is also known as ED, extra type III repeat A (EIIIA) or EDI. The sequence of human ED-A has been published by Kornblihtt et al. (1984), Nucleic Acids Res. 12, 5853-5868 and Paolella et al. (1988), Nucleic Acids Res. 16, 3545-3557. The sequence of human ED-A is also available on the SwissProt database as amino acids 1631-1720 (Fibronectin type-III 12; extra domain 2) of the amino acid sequence deposited under accession number P02751. The sequence of mouse ED-A is available on the SwissProt database as amino acids 1721-1810 (Fibronectin type-III 13; extra domain 2) of the amino acid sequence deposited under accession number P11276.

The ED-A isoform of fibronectin (A-FN) contains the Extra Domain-A (ED-A). The sequence of the human A-FN can be deduced from the corresponding human fibronectin precursor sequence which is available on the SwissProt database under accession number P02751. The sequence of the mouse A-FN can be deduced from the corresponding mouse fibronectin precursor sequence which is available on the SwissProt database under accession number P11276. The A-FN may be the human ED-A isoform of fibronectin. The ED-A may be the Extra Domain-A of human fibronectin.

ED-A is a 90 amino acid sequence which is inserted into fibronectin (FN) by alternative splicing and is located between domain 11 and 12 of FN (Borsi et al., 1987, J. Cell Biol., 104, 595-600). ED-A is mainly absent in the plasma form of FN but is abundant during embryogenesis, tissue remodelling, fibrosis, cardiac transplantation and solid tumour growth.

Alternative Splicing

Alternative splicing refers to the occurrence of different patterns of splicing of a primary RNA transcript of DNA to produce different mRNAs. After excision of introns, selection may determine which exons are spliced together to form the mRNA. Alternative splicing leads to production of different isoforms containing different exons and/or different numbers of exons. For example one isoform may comprise an additional amino acid sequence corresponding to one or more exons, which may comprise one or more domains.

Binding Member

This describes one member of a pair of molecules that bind one another. The members of a binding pair may be naturally derived or wholly or partially synthetically produced. One member of the pair of molecules has an area on its surface, or a cavity, which binds to and is therefore complementary to a particular spatial and polar organization of the other member of the pair of molecules. Examples of types of binding pairs are antigen-antibody, biotin-avidin, hormone-hormone receptor, receptor-ligand, enzyme-substrate. The present invention is concerned with antigen-antibody type reactions.

A binding member normally comprises a molecule having an antigen-binding site. For example, a binding member may be an antibody molecule or a non-antibody protein that comprises an antigen-binding site.

An antigen binding site may be provided by means of arrangement of complementarity determining regions (CDRs) on non-antibody protein scaffolds such as fibronectin or cytochrome B etc. (Haan & Maggos, 2004; Koide 1998; Nygren 1997), or by randomising or mutating amino acid residues of a loop within a protein scaffold to confer binding specificity for a desired target. Scaffolds for engineering novel binding sites in proteins have been reviewed in detail by Nygren et al. (1997). Protein scaffolds for antibody mimics are disclosed in WO/0034784, which is herein incorporated by reference in its entirety, in which the inventors describe proteins (antibody mimics) that include a fibronectin type III domain having at least one randomised loop. A suitable scaffold into which to graft one or more CDRs, e.g., a set of HCDRs, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties such as an ability to enter cells, penetrate deep into tissues or reach targets within other structures, or to bind within protein cavities of the target antigen. Use of antigen binding sites in non-antibody protein scaffolds is reviewed in Wess, 2004. Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from *S. aureus*, transferrin, tetranectin, fibronectin (e.g. 10th fibronectin type III domain) and lipocalins. Other approaches include synthetic "Microbodies" (Selecore GmbH), which are based on cyclotides—small proteins having intra-molecular disulphide bonds.

In addition to antibody sequences and/or an antigen-binding site, a binding member according to the present invention may comprise other amino acids, e.g. forming a peptide or polypeptide, such as a folded domain, or to impart to the molecule another functional characteristic in addition to ability to bind antigen. Binding members of the invention may carry a detectable label, or may be conjugated to a toxin or a targeting moiety or enzyme (e.g. via a peptidyl bond or linker). For example, a binding member may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Although, as noted, CDRs can be carried by non-antibody scaffolds, the structure for carrying a CDR or a set of CDRs of the invention will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat 1987, and updates thereof, now available on the Internet (at immuno.bme.nwu.edu or find "Kabat" using any search engine).

By CDR region or CDR, it is intended to indicate the hypervariable regions of the heavy and light chains of the immunoglobulin as defined by Kabat et al. (1987), (Kabat 1991a, and later editions). An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It can be as short as 2 amino acids although the longest size known is 26. Functionally, HCDR3 plays a role in part in the determination of the specificity of the antibody (Segal 1974; Amit 1986; Chothia 1987; Chothia 1989; Caton 1990; Sharon 1990a; Sharon 1990b; Rabat et al., 1991b).

Antibody Molecule

This describes an immunoglobulin whether natural or partly or wholly synthetically produced. The term also covers any polypeptide or protein comprising an antibody antigen-binding site. It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described later. Antibody fragments that comprise an antibody antigen-binding site include, but are not limited to, antibody molecules such as Fab, Fab', Fab'-SH, scFv, Fv, dAb, Fd; and diabodies.

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

As antibodies can be modified in a number of ways, the term "antibody molecule" should be construed as covering any binding member or substance having an antibody antigen-binding site with the required specificity and/or binding to antigen. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide (e.g. derived from another species or belonging to another antibody class or subclass) are therefore included. Cloning and expression of chimeric antibodies are described in EP-A-0120694 and EP-A-0125023, and a large body of subsequent literature.

Further techniques available in the art of antibody engineering have made it possible to isolate human and humanised antibodies. For example, human hybridomas can be made as described by Eontermann & Dubel (2001). Phage display, another established technique for generating binding members has been described in detail in many publications such as WO92/01047 (discussed further below) and U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160, 6,521,404 and Kontermann & Dubel (2001). Transgenic mice in which the mouse antibody genes are inactivated and functionally replaced with human antibody genes while leaving intact other components of the mouse immune system, can be used for isolating human antibodies (Mendez 1997).

Synthetic antibody molecules may be created by expression from genes generated by means of oligonucleotides synthesized and assembled within suitable expression vectors, for example as described by Knappik et al. (2000) or Krebs et al. (2001).

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward 1989; McCafferty 1990; Holt 2003), which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird 1988; Huston 1988); (viii) bispecific single chain Fv dimers (PCT/US92/09965) and (ix) "diabodies", multivalent or multispecific fragments constructed by gene fusion (WO94/13804; Holliger 1993a). Fv, scFv or diabody molecules may be stabilized by the incorporation of disulphide bridges linking the VH and VL domains (Reiter 1996). Minibodies comprising a scFv joined to a CH3 domain may also be made (Hu 1996). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

Antibody fragments of the invention can be obtained starting from any of the antibody molecules described herein, e.g. antibody molecules comprising VH and/or VL domains or CDRs of any of antibodies described herein, by methods such as digestion by enzymes, such as pepsin or papain and/or by cleavage of the disulfide bridges by chemical reduction. In another manner, antibody fragments of the present invention may be obtained by techniques of genetic recombination likewise well known to the person skilled in the art or else by peptide synthesis by means of, for example, automatic peptide synthesizers such as those supplied by the company Applied Biosystems, etc., or by nucleic acid synthesis and expression.

Functional antibody fragments according to the present invention include any functional fragment whose half-life is increased by a chemical modification, especially by PEGylation, or by incorporation in a liposome.

A dAb (domain antibody) is a small monomeric antigen-binding fragment of an antibody, namely the variable region of an antibody heavy or light chain (Holt 2003). VH dAbs occur naturally in camelids (e.g. camel, llama) and may be produced by immunizing a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. A binding member of the present invention may be a dAb comprising a VH or VL domain substantially as set out herein, or a VH or VL domain comprising a set of CDRs substantially as set out herein.

As used herein, the phrase "substantially as set out" refers to the characteristic(s) of the relevant CDRs of the VH or VL domain of binding members described herein will be either identical or highly similar to the specified regions of which the sequence is set out herein. As described herein, the phrase "highly similar" with respect to specified region(s) of one or more variable domains, it is contemplated that from 1 to about 5, e.g. from 1 to 4, including 1 to 3, or 1 or 2, or 3 or 4, amino acid substitutions may be made in the CDR and/or VH or VL domain.

Bispecific or bifunctional antibodies form a second generation of monoclonal antibodies in which two different variable regions are combined in the same molecule (Holliger 1999). Their use has been demonstrated both in the diagnostic field and in the therapy field from their capacity to recruit new effector functions or to target several molecules on the surface of tumor cells. Where bispecific antibodies are to be used, these may be conventional bispecific antibodies, which can be manufactured in a variety of ways (Holliger 1993b), e.g. prepared chemically or from hybrid hybridomas, or may be any of the bispecific antibody fragments mentioned above. These antibodies can be obtained by chemical methods (Glennie 1987; Repp 1995) or somatic methods (Staerz 1986; Suresh 1986) but likewise by genetic engineering techniques which allow the heterodimerization to be forced and thus facilitate the process of purification of the antibody sought (Merchand 1998). Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against a target antigen, then a library can be made where the other arm is varied and an antibody of appropriate specificity selected. Bispecific whole antibodies may be made by alternative engineering methods as described in Ridgeway 1996.

Various methods are available in the art for obtaining antibodies against a target antigen. The antibodies may be monoclonal antibodies, especially of human, murine, chimeric or humanized origin, which can be obtained according to the standard methods well known to the person skilled in the art.

In general, for the preparation of monoclonal antibodies or their functional fragments, especially of murine origin, it is possible to refer to techniques which are described in particular in the manual "Antibodies" (Harlow and Lane 1988) or to the technique of preparation from hybridomas described by Kohler and Milstein, 1975.

Monoclonal antibodies can be obtained, for example, from an animal cell immunized against A-FN, or one of its fragments containing the epitope recognized by said monoclonal antibodies, e.g. a fragment comprising or consisting of ED-A, or a peptide fragment of ED-A. The A-FN, or one of its fragments, can especially be produced according to the usual working methods, by genetic recombination starting with a nucleic acid sequence contained in the cDNA sequence coding for A-FN or fragment thereof, by peptide synthesis starting from a sequence of amino acids comprised in the peptide sequence of the A-FN and/or fragment thereof.

Monoclonal antibodies can, for example, be purified on an affinity column on which A-FN or one of its fragments containing the epitope recognized by said monoclonal antibodies, e.g. a fragment comprising or consisting of ED-A or a peptide fragment of ED-A, has previously been immobilized. Monoclonal antibodies can be purified by chromatography on protein A and/or G, followed or not followed by ion-exchange chromatography aimed at eliminating the residual protein contaminants as well as the DNA and the LPS, in itself, followed or not followed by exclusion chromatography on Sepharose gel in order to eliminate the potential aggregates due to the presence of dimers or of other multimers. The whole of these techniques may be used simultaneously or successively.

Antigen-Binding Site

This describes the part of a molecule that binds to and is complementary to all or part of the target antigen. In an antibody molecule it is referred to as the antibody antigen-binding site, and comprises the part of the antibody that binds to and is complementary to all or part of the target antigen. Where an antigen is large, an antibody may only bind to a particular part of the antigen, which part is termed an epitope. An antibody antigen-binding site may be provided by one or more antibody variable domains. An antibody antigen-binding site may comprise an antibody light chain variable region (VL) and an antibody heavy chain variable region (VH).

Isolated

This refers to the state in which binding members of the invention or nucleic acid encoding such binding members, will generally be in accordance with the present invention. Thus, binding members, VH and/or VL domains of the present invention may be provided isolated and/or purified, e.g. from their natural environment, in substantially pure or homogeneous form, or, in the case of nucleic acid, free or substantially free of nucleic acid or genes of origin other than the sequence encoding a polypeptide with the required function. Isolated members and isolated nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

Heterogeneous preparations comprising antibody molecules also form part of the invention. For example, such preparations may be mixtures of antibodies with full-length heavy chains and heavy chains lacking the C-terminal lysine, with various degrees of glycosylation and/or with derivatized amino acids, such as cyclization of an N-terminal glutamic acid to form a pyroglutamic acid residue.

One or more binding members for an antigen, e.g. the A-FN or the ED-A of fibronectin, may be obtained by bringing into contact a library of binding members according to the invention and the antigen or a fragment thereof, e.g. a fragment comprising or consisting of ED-A or a peptide fragment of ED-A and selecting one or more binding members of the library able to bind the antigen.

An antibody library may be screened using Iterative Colony Filter Screening (ICFS). In ICFS, bacteria containing the DNA encoding several binding specificities are grown in a liquid medium and, once the stage of exponential growth has been reached, some billions of them are distributed onto a growth support consisting of a suitably pre-treated membrane filter which is incubated until completely confluent bacteriae colonies appear. A second trap substrate consists of another membrane filter, pre-humidified and covered with the desired antigen.

The trap membrane filter is then placed onto a plate containing a suitable culture medium and covered with the growth filter with the surface covered with bacterial colonies pointing upwards. The sandwich thus obtained is incubated at room temperature for about 16 h. It is thus possible to obtain the expression of the genes encoding antibody fragments scFv having a spreading action, so that those fragments binding specifically with the antigen which is present on the trap membrane are trapped. The trap membrane is then treated to point out bound antibody fragments scFv with colorimetric techniques commonly used to this purpose.

The position of the coloured spots on the trap filter allows to go back to the corresponding bacterial colonies which are present on the growth membrane and produced the antibody fragments trapped. Such colonies are gathered and grown and the bacteria—a few millions of them are distributed onto a new culture membrane repeating the procedures described above. Analogous cycles are then carried out until the positive signals on the trap membrane correspond to single positive colonies, each of which represents a potential source of monoclonal antibody fragments directed against the antigen used in the selection. ICFS is described in e.g. WO0246455, which is incorporated herein by reference. A library may also be displayed on particles or molecular complexes, e.g. replicable genetic packages such bacteriophage (e.g. T7) particles, or other in vitro display systems, each particle or molecular complex containing nucleic acid encoding the antibody VH variable domain displayed on it, and optionally also a displayed VL domain if present. Phage display is described in WO92/01047 and e.g. U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160 and U.S. Pat. No. 6,521,404, each of which is herein incorporated by reference in its entirety.

Following selection of binding members able to bind the antigen and displayed on bacteriophage or other library particles or molecular complexes, nucleic acid may be taken from a bacteriophage or other particle or molecular complex displaying a said selected binding member. Such nucleic acid may be used in subsequent production of a binding member or an antibody VH or VL variable domain by expression from nucleic acid with the sequence of nucleic acid taken from a bacteriophage or other particle or molecular complex displaying a said selected binding member.

An antibody VH variable domain with the amino acid sequence of an antibody VH variable domain of a said selected binding member may be provided in isolated form, as may a binding member comprising such a VH domain.

Ability to bind the A-FN or the ED-A of fibronectin or other target antigen or isoform may be further tested, e.g. ability to compete with e.g. any one of anti-ED-A antibodies H1, B2, C5, D5, E5, C8, F8, F1, B7, E8 or G9 for binding to the A-FN or a fragment of the A-FN, e.g the ED-A of fibronectin.

A binding member of the invention may bind the A-FN and/or the ED-A of fibronectin specifically. A binding member of the present invention may bind the A-FN and/or the ED-A of fibronectin with the same affinity as anti-ED-A antibody H1, B2, C5, D5, E5, C8, F8, F1, B7, E8 or G9, e.g. in scFv format, or with an affinity that is better. A binding member of the invention may bind the A-FN and/or the ED-A of fibronectin with a $K_D$ of $3\times10^{-8}$ M or an affinity that is better. Preferably, a binding member of the invention binds the A-FN and/or the ED-A of fibronectin with a $K_D$ of $2\times10^{-8}$ M or an affinity that is better. More preferably, a binding member of the invention binds the A-FN and/or the ED-A of fibronectin with a $K_D$ of $1.7\times10^{-8}$ M or an affinity that is better. Yet more preferably, a binding member of the invention binds the A-FN and/or the ED-A of fibronectin with a $R_D$ of $1.4\times10^{-8}$ M or an affinity that is better. Most preferably, a binding member of the invention binds the A-FN and/or the ED-A of fibronectin with a $K_D$ of $3\times10^{-9}$ M or an affinity that is better.

A binding member of the present invention may bind to the same epitope on A-FN and/or the ED-A of fibronectin as anti-ED-A antibody H1, B2, C5, D5, E5, C8, F8, F1, B7, E8 or G9.

A binding member of the invention may not show any significant binding to molecules other than the A-FN and/or the ED-A of fibronectin. In particular the binding member may not bind other isoforms of fibronectin, for example the ED-B isoform and/or the IIICS isoform of fibronectin.

Variants of antibody molecules disclosed herein may be produced and used in the present invention. The techniques required to make substitutions within amino acid sequences of CDRs, antibody VH or VL domains and binding members generally are available in the art. Variant sequences may be made, with substitutions that may or may not be predicted to have a minimal or beneficial effect on activity, and tested for ability to bind A-FN and/or the ED-A of fibronectin and/or for any other desired property.

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion of an amino acid residue), may be less than about 20 alterations, less than about 15 alterations, less than about 10 alterations or less than about 5 alterations, maybe 5, 4, 3, 2 or 1. Alterations may be made in one or more framework regions and/or one or more CDRs. The alterations normally do not result in loss of function, so a binding member comprising a thus-altered amino acid sequence may retain an ability to bind A-FN and/or the ED-A of fibronectin. For example, it may retain the same quantitative binding as a binding member in which the alteration is not made, e.g. as measured in an assay described herein. The binding member comprising a thus-altered amino acid sequence may have an improved ability to bind A-FN and/or the ED-A of fibronectin.

Novel VH or VL regions carrying CDR-derived sequences of the invention may be generated using random mutagenesis of one or more selected VH and/or VL genes to generate mutations within the entire variable domain. In some embodiments one or two amino acid substitutions are made within an entire variable domain or set of CDRs. Another method that may be used is to direct mutagenesis to CDR regions of VH or VL genes.

As noted above, a CDR amino acid sequence substantially as set out herein may be carried as a CDR in a human antibody variable domain or a substantial portion thereof. The HCDR3 sequences substantially as set out herein represent embodiments of the present invention and for example each of these may be carried as a HCDR3 in a human heavy chain variable domain or a substantial portion thereof.

Variable domains employed in the invention may be obtained or derived from any germ-line or rearranged human variable domain, or may be a synthetic variable domain based on consensus or actual sequences of known human variable domains. A variable domain can be derived from a non-human antibody. A CDR sequence of the invention (e.g. CDR3) may be introduced into a repertoire of variable domains lacking a CDR (e.g. CDR3), using recombinant DNA technology. For example, Marks et al. (1992) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide binding members of the invention. The repertoire may then be displayed in a suitable host system such as the phage display system of WO92/01047, which is herein incorporated by reference in its entirety, or any of a subsequent large body of literature, including Kay, Winter & McCafferty (1996), so that suitable binding members may be selected. A repertoire may consist of from anything from $10^4$ individual members upwards, for example at least $10^5$, at least $10^6$, at least $10^7$, at least $10^8$, at least $10^9$ or at least $10^{10}$ members.

Similarly, one or more, or all three CDRs may be grafted into a repertoire of VH or VL domains that are then screened for a binding member or binding members for the A-FN and/or the ED-A of fibronectin.

One or more of the HCDR1, HCDR2 and HCDR3 of antibody H1, B2, C5, D5, E5, C8, F8, F1, B7, E8 or G9, or the set of HCDRs may be employed, and/or one or more of the X LCDR1, LCDR2 and LCDR3 of antibody H1, B2, C5, D5, E5, C8, F8, F1, B7, E8 or G9 or the set of LCDRs of antibody H1, B2, C5, D5, E5, C8, F8, F1, B7, E8 or G9 may be employed.

Similarly, other VH and VL domains, sets of CDRs and sets of HCDRs and/or sets of LCDRs disclosed herein may be employed.

The A-FN and/or the ED-A of fibronectin may be used in a screen for binding members, e.g. antibody molecules, for use in the preparation of a medicament for the treatment of tumour metastases. The screen may a screen of a repertoire as disclosed elsewhere herein.

In some embodiments, a substantial portion of an immunoglobulin variable domain will comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including antibody constant regions, other variable domains (for example in the production of diabodies) or detectable/functional labels as discussed in more detail elsewhere herein.

Although in some aspects of the invention, binding members comprise a pair of VH and VL domains, single binding domains based on either VH or VL domain sequences form further aspects of the invention. It is known that single immunoglobulin domains, especially VH domains, are capable of binding target antigens in a specific manner. For example, see the discussion of dAbs above.

In the case of either of the single binding domains, these domains may be used to screen for complementary domains capable of forming a two-domain binding member able to bind A-FN and/or the ED-A of fibronectin. This may be achieved by phage display screening methods using the so-called hierarchical dual combinatorial approach as disclosed in WO92/01047, herein incorporated by reference in its entirety, in which an individual colony containing either an H or L chain clone is used to infect a complete library of clones encoding the other chain (L or H) and the resulting two-chain binding member is selected in accordance with phage display techniques such as those described in that reference. This technique is also disclosed in Marks 1992.

Binding members of the present invention may further comprise antibody constant regions or parts thereof, e.g. human antibody constant regions or parts thereof. For example, a VL domain may be attached at its C-terminal end to antibody light chain constant domains including human Cκ or Cλ chains, e.g. Cλ. Similarly, a binding member based on a VH domain may be attached at its C-terminal end to all or part (e.g. a CH1 domain) of an immunoglobulin heavy chain derived from any antibody isotype, e.g. IgG, IgA, IgE and IgM and any of the isotype sub-classes, particularly IgG1 and IgG4. Any synthetic or other constant region variant that has these properties and stabilizes variable regions is also useful in embodiments of the present invention.

Binding members of the invention may be labelled with a detectable or functional label. A label can be any molecule that produces or can be induced to produce a signal, including but not limited to fluorescers, radiolabels, enzymes, chemiluminescers or photosensitizers. Thus, binding may be detected and/or measured by detecting fluorescence or luminescence, radioactivity, enzyme activity or light absorbance. Detectable labels may be attached to antibodies of the invention using conventional chemistry known in the art.

There are numerous methods by which the label can produce a signal detectable by external means, for example, by visual examination, electromagnetic radiation, heat, and chemical reagents. The label can also be bound to another binding member that binds the antibody of the invention, or to a support.

Labelled binding members, e.g. scFv labelled with a detectable label, may be used diagnostically in vivo, ex vivo or in vitro, and/or therapeutically.

For example, radiolabelled binding members (e.g. binding members conjugated to a radioisotope) may be used in radio-diagnosis and radiotherapy. Radioisotopes which may be conjugated to a binding member of the invention include isotopes such as $^{94m}$Tc, $^{99m}$Tc, $^{186}$Re, $^{188}$Re, $^{203}$Pb, $^{67}$Ga, $^{68}$Ga, $^{47}$Sc, $^{111}$In, $^{97}$Ru, $^{62}$Cu, $^{64}$Cu, $^{86}$Y, $^{88}$Y, $^{90}$Y, $^{121}$Sn, $^{161}$Tb, $^{153}$Sm, $^{166}$Ho, $^{105}$Rh and $^{177}$Lu.

For example, a binding member of the invention labelled with a detectable label may be used to detect, diagnose or monitor tumour metastases and/or tumour metastasis in a human or animal. The binding member may be administered to a human or animal, normally a human patient, and the presence or absence of the antibody at a site distant from a site currently or previously occupied by a primary tumour in the human or animal body may be determined; localisation of the antibody molecule to a site distant from the site currently or previously occupied by the primary tumour in the human or animal indicates the presence of a tumour metastases and/or tumour metastasis.

A binding member of the present invention may be used for the manufacture of a diagnostic product for use in diagnosing tumour metastases.

The present invention also provides a method of detecting or diagnosing a tumour metastases in a human or animal comprising the steps of:
(a) administering to the human or animal a binding member of the present invention, for example labelled with a detectable label, which binds the ED-A isoform of fibronectin and/or the ED-A of fibronectin, and
(b) determining the presence or absence of the binding member at a site distant from a site currently or previously occupied by a primary tumour in the human or animal body;

wherein localisation of the binding member to a site distant from the site currently or previously occupied by the primary tumour in the human or animal indicates the presence of a tumour metastases. Where the binding member is labelled with a detectable label, the presence or absence of the detectable label may be determined by detecting the label.

A binding member as described herein may also be used for measuring antigen levels in a competition assay, that is to say a method of measuring the level of antigen in a sample by employing a binding member as provided by the present invention in a competition assay. This may be where the physical separation of bound from unbound antigen is not required. Linking a reporter molecule to the binding member so that a physical or optical change occurs on binding is one possibility. The reporter molecule may directly or indirectly generate detectable signals, which may be quantifiable. The linkage of reporter molecules may be directly or indirectly, covalently, e.g. via a peptide bond or non-covalently. Linkage via a peptide bond may be as a result of recombinant expression of a gene fusion encoding antibody and reporter molecule.

Competition assays can also be used in epitope mapping. In one instance epitope mapping may be used to identify the epitope bound by a binding member. Such an epitope can be linear or conformational. A conformational epitope can comprise at least two different fragments of A-FN or the ED-A of fibronectin, wherein said fragments are positioned in proximity to each other when A-FN or the ED-A of fibronectin is folded in its tertiary or quaternary structure to form a conformational epitope which is recognized by a A-FN or the ED-A of fibronectin binding member. In testing for competition a peptide fragment of the antigen may be employed, especially a peptide including or consisting essentially of an epitope of interest. A peptide having the epitope sequence plus one or more amino acids at either end may be used. Binding members according to the present invention may be such that their binding for antigen is inhibited by a peptide with or including the sequence given.

Further aspects of the present invention employ a conjugate or fusion between a binding member of the invention and a molecule that exerts a biocidal or cytotoxic effect on target cells in the lesions and an antibody directed against an extracellular matrix component which is present in such lesions. For example, the biocidal or cytotoxic molecule may be interleukin-2 (IL-2), doxorubicin, interleukin-12 (IL-12), Interferon-γ (IFN-γ), Tumour Necrosis Factor α (TNFα) or tissue factor (preferably truncated). Such conjugates may be used therapeutically, e.g. for treatment of tumour metastases and/or tumour as referred to herein. Production and use of fusions or conjugates of binding members with biocidal or cytotoxic molecules is described for example in WO01/62298, which is incorporated by reference herein.

In one aspect the invention provides a method of treating tumour metastasis and/or tumour metastases, the method comprising administering a to an individual a therapeutically effective amount of a medicament comprising a binding member of the invention. The binding member may be a conjugate of (i) a molecule which exerts a biocidal or cytotoxic effect on target cells by cellular interaction and (ii) a binding member for the ED-A isoform of fibronectin and/or the ED-A of fibronectin.

In another aspect the invention provides the use of a binding member of the invention for the preparation of a medicament for the treatment of tumour metastases and/or tumour metastasis. The binding member may be a conjugated or fused to a molecule that exerts a biocidal or cytotoxic effect as described herein. The binding member may be a conjugate of (i) a molecule which exerts a biocidal or cytotoxic effect on target cells by cellular interaction and (ii) a binding member for human fibronectin according to the present invention.

In a further aspect the invention provides a conjugate of (i) a molecule which exerts a biocidal or cytotoxic effect on target cells by cellular interaction and (ii) a binding member for human fibronectin according to the present invention, for use in a method of treatment of the human or animal body by therapy. Such treatment may be of tumour metastases and/or tumour metastasis.

A still further aspect of the invention provides a conjugate of (i) a molecule which exerts a biocidal or cytotoxic effect on target cells by cellular interaction and (ii) a binding member for human fibronectin according to the present invention. Such a conjugate preferably comprises a fusion protein comprising the biocidal or cytotoxic molecule and a said binding member, or, where the binding member is two-chain or multi-chain, a fusion protein comprising the biocidal or cytotoxic molecule and a polypeptide chain component of said binding member. Preferably the binding member is a single-chain polypeptide, e.g. a single-chain antibody molecule, such as scFv. Thus a further aspect of the present invention provides a fusion protein comprising the biocidal or cytotoxic molecule and a single-chain Fv antibody molecule of the invention.

The biocidal or cytotoxic molecule that exerts its effect on target cells by cellular interaction, may interact directly with the target cells, may interact with a membrane-bound receptor on the target cell or perturb the electrochemical potential of the cell membrane. Molecules which interact with a membrane-bound receptor include chemokines, cytokines and hormones. Compounds which perturb the electrochemical potential of the cell membrane include hemolysin, ionophores, drugs acting on ion channels. In exemplary preferred embodiments the molecule is interleukin-2, tissue factor (preferably truncated) or doxorubicin. Other embodiments may employ interleukin 12, interferon-gamma, IP-10 and Tumor Necrosis Factor-α (TNF-α).

As discussed further below, the specific binding member is preferably an antibody or comprises an antibody antigen-binding site. Conveniently, the specific binding member may be a single-chain polypeptide, such as a single-chain antibody. This allows for convenient production of a fusion protein comprising single-chain antibody and the biocidal or cytotoxic molecule (e.g. interleukin-2 or tissue factor). In other embodiments, an antibody antigen-binding site is provided by means of association of an antibody VH domain and an antibody VL domain in separate polypeptides, e.g. in a complete antibody or in an antibody fragment such as Fab or diabody. Where the specific binding member is a two-chain or multi-chain molecule (e.g. Fab or whole antibody, respectively), the biocidal or cytotoxic molecule may be conjugated as a fusion polypeptide with one or more polypeptide chains in the specific binding member.

The binding member may be conjugated with the biocidal or cytotoxic molecule by means of a peptide bond, i.e. within a fusion polypeptide comprising said molecule and the specific binding member or a polypeptide chain component thereof. See Taniguchi et al. (1983) Nature 302, 305-310; MaED-A et al. (1983) Biochem. Biophys. Res. Comm. 115: 1040-1047; Devos et al. (1983) Nucl. Acids Res. 11: 4307-4323 for IL-2 sequence information useful in preparation of a fusion polypeptide comprising IL-2. Sequence information for truncated tissue factor is provided by Scarpati et al. (1987) Biochemistry 26: 5234-5238, and Ruf et al. (1991) J. Biol. Chem. 226: 15719-15725. Other means for conjugation include chemical conjugation, especially cross-linking using a bifunctional reagent (e.g. employing DOUBLE-RE-AGENTS™ Cross-linking Reagents Selection Guide, Pierce).

Where slow release is desirable, e.g. where the biocidal or cytotoxic molecule is doxorubicin or other molecule which perturbs the electrochemical potential of the cell membrane, chemical conjugation may be by means of formation of a Schiff base (imine) between a primary amino group of the specific binding member (a polypeptide such as an antibody or antibody fragment) and an oxidised sugar moiety (daunosamine) of the biocidal or cytotoxic molecule such as doxorubicin.

The present invention further provides an isolated nucleic acid encoding a binding member of the present invention. Nucleic acid may include DNA and/or RNA. In one aspect, the present invention provides a nucleic acid that codes for a CDR or set of CDRs or VH domain or VL domain or antibody antigen-binding site or antibody molecule, e.g. scFv or IgG, e.g. IgG1, of the invention as defined above. Preferred nucleotide sequences are the nucleotide sequences encoding VH and/or VL domains disclosed herein.

The present invention also provides constructs in the form of plasmids, vectors, transcription or expression cassettes which comprise at least one polynucleotide as above.

The present invention also provides a recombinant host cell that comprises one or more constructs as above. A nucleic acid encoding any CDR or set of CDRs or VH domain or VL domain or antibody antigen-binding site or antibody molecule, e.g. scFv or IgG1 or IgG4 as provided, itself forms an aspect of the present invention, as does a method of production of the encoded product, which method comprises expression from encoding nucleic acid. Expression may conveniently be achieved by culturing under appropriate conditions recombinant host cells containing the nucleic acid. Following production by expression a VH or VL domain, or binding member may be isolated and/or purified using any suitable technique, then used as appropriate.

Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

A yet further aspect provides a method of production of an antibody VH variable domain, the method including causing expression from encoding nucleic acid. Such a method may comprise culturing host cells under conditions for production of said antibody VH variable domain.

Analogous methods for production of VL variable domains and binding members comprising a VH and/or VL domain are provided as further aspects of the present invention.

A method of production may comprise a step of isolation and/or purification of the product. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals. The expression of antibodies and antibody fragments in prokaryotic cells is well established in the art. For a review, see for example Plückthun 1991. A common bacterial host is E. coli.

Expression in eukaryotic cells in culture is also available to those skilled in the art as an option for production of a binding member for example Chadd & Chamow (2001), Andersen & Krummen (2002), Larrick & Thomas (2001). Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral e.g. 'phage, as appropriate. For further details see, for example, Sambrook & Russell (2001). Many known techniques and protocols for manipulation of nucleic acid, for example in preparation of nucleic acid constructs, mutagenesis, sequencing, introduction of DNA into cells and gene expression, and analysis of proteins, are described in detail in Ausubel 1999.

A further aspect of the present invention provides a host cell containing nucleic acid as disclosed herein. Such a host cell may be in vitro and may be in culture. Such a host cell may be in vivo. In vivo presence of the host cell may allow intracellular expression of the binding members of the present invention as "intrabodies" or intracellular antibodies. Intrabodies may be used for gene therapy.

A still further aspect provides a method comprising introducing nucleic acid of the invention into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system.

The plasmid system may be maintained episomally or may incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene. The purification of the expressed product may be achieved by methods known to one of skill in the art.

In accordance with the invention, the nucleic acid of the invention may be integrated into the genome (e.g. chromosome) of the host cell. Integration may be promoted by inclusion of sequences that promote recombination with the genome, in accordance with standard techniques.

The present invention also provides a method that comprises using a construct as stated above in an expression system in order to express a binding member or polypeptide as above.

Binding members of the present invention are designed to be used in methods of diagnosis or treatment in human or animal subjects, e.g. human. Binding members may be used in diagnosis or treatment of tumour metastases and/or tumour metastasis.

Accordingly, further aspects of the invention provide methods of treatment comprising administration of a binding member as provided, pharmaceutical compositions comprising such a binding member, and use of such a binding member in the manufacture of a medicament for administration, for example in a method of making a medicament or pharmaceutical composition comprising formulating the binding member with a pharmaceutically acceptable excipient. Pharmaceutically acceptable vehicles are well known and will be adapted by the person skilled in the art as a function of the nature and of the mode of administration of the active compound(s) chosen.

Binding members of the present invention will usually be administered in the form of a pharmaceutical composition, which may comprise at least one component in addition to the binding member. Thus pharmaceutical compositions according to the present invention, and for use in accordance with the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, inhaled or by injection, e.g. intravenous.

Pharmaceutical compositions for oral administration such as for example nanobodies etc are also envisaged in the present invention. Such oral formulations may be in tablet, capsule, powder, liquid or semi-solid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be employed, as required. Many methods for the preparation of pharmaceutical formulations are known to those skilled in the art. See, e.g., Robinson, 1978.

A composition may be administered alone or in combination with other treatments, concurrently or sequentially or as a combined preparation with another therapeutic agent or agents, dependent upon the condition to be treated.

A binding member for A-FN and/or the ED-A of fibronectin may be used as part of a combination therapy in conjunction with an additional medicinal component. Combination treatments may be used to provide significant synergistic effects, particularly the combination of a binding member which binds the A-FN and/or the ED-A of fibronectin with one or more other drugs. A binding member for the A-FN and/or the ED-A of fibronectin may be administered concurrently or sequentially or as a combined preparation with another therapeutic agent or agents, for the treatment of one or more of the conditions listed herein.

For example, a binding member of the invention may be used in combination with an existing therapeutic agent for the treatment of tumour metastases and/or tumour metastasis. Existing therapeutic agents for the treatment of tumour metastases and/or tumour metastasis include: doxorubicin, taxol, gemcitabine, sorafenib, melphalan, and avastin.

A binding member of the invention and one or more of the above additional medicinal components may be used in the manufacture of a medicament. The medicament may be for separate or combined administration to an individual, and accordingly may comprise the binding member and the additional component as a combined preparation or as separate preparations. Separate preparations may be used to facilitate separate and sequential or simultaneous administration, and allow administration of the components by different routes e.g. oral and parenteral administration.

In accordance with the present invention, compositions provided may be administered to mammals. Administration may be in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the type of binding member, the method of administration, the scheduling of administration and other factors known to medical practitioners. Prescription of treatment, e.g. decisions on dosage etc, is within the responsibility of general practitioners and other medical doctors, and may depend on the severity of the symptoms and/or progression of a disease being treated.

Appropriate doses of antibody are well known in the art (Ledermann 1991 and Bagshawe 1991. Specific dosages indicated herein, or in the Physician's Desk Reference (2003) as appropriate for the type of medicament being administered, may be used. A therapeutically effective amount or suitable dose of a binding member of the invention can be determined by comparing its in vitro activity and in vivo activity in an animal model. Methods for extrapolation of effective dosages in mice and other test animals to humans are known. The precise dose will depend upon a number of factors, including whether the antibody is for diagnosis, prevention or for treatment, the size and location of the area to be treated, the precise nature of the antibody (e.g. whole antibody, fragment or diabody), and the nature of any detectable label or other molecule attached to the antibody. A typical antibody dose will be in the range 100 µg to 1 g for systemic applications, and 1 µg to 1 mg for topical applications. An initial higher loading dose, followed by one or more lower doses, may be administered. An antibody may be a whole antibody, e.g. the IgG1 or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. Treatments may be every two to four weeks for subcutaneous administration and every four to eight weeks for intravenous administration. In some embodiments of the present invention, treatment is periodic, and the period between administrations is about two weeks or more, e.g. about three weeks or more, about four weeks or more, or about once a month. In other embodiments of the invention, treatment may be given before, and/or after surgery, and may be administered or applied directly at the anatomical site of surgical treatment.

Further aspects and embodiments of the invention will be apparent to those skilled in the art given the present disclosure including the following experimental exemplification.

EXPERIMENTAL

Materials and Methods

Animal Model

Animal experiments were approved by the Swiss Federal Veterinary Office and performed in accordance with the Swiss Animal Protection Ordinance. Mice were monitored regularly. When showing any sign of pain or suffering, or in case of a body weight loss >15% animals were euthanized. Male Sv129 mice (RCC, Füllingsdorf, Switzerland) received intravenous injection of ~$10^6$ mutant F9 murine teratocarcinoma cells (Terrana et al. 1987), which had been kindly provided by Dario Rusciano (SIFI, Catania, Italy). Mice were used 3 weeks after tumour cell injection for in vivo biotinylation, targeting experiments or organ excision for immunohistochemistry.

In Vivo Biotinylation

In vivo biotinylation experiments were performed as described previously (Roesli et al. 2006, Rybak et al. 2005). In brief, the chest of the anesthetized mouse was opened through a median sternotomy. The left heart ventricle was punctured with a perfusion needle and a small cut was made in the right atrium to allow the outflow of the perfusion solutions. Immediately after, perfusion of the systemic circulation was performed with a pressure of 100 mm Hg at a flow rate of 1.5 ml/min. In a first step, perfusion was carried out with 15 ml biotinylation solution (pre-warmed to 38° C.), containing 1 mg/ml sulfo-NHS-LC-biotin (Pierce, Rockford, Ill., USA) in PBS, pH 7.4, supplemented with 10% (w/v) dextran-40 (Amersham Biosciences, Uppsala, Sweden) as plasma expander. Thereby, blood components, which could compete with the biotinylation reaction, were eliminated from circulation within the first few minutes of perfusion and accessible primary amine-containing proteins (and certain glycolipids and phospholipids) in the different tissues could be covalently modified with biotin. To neutralize unreacted biotinylation reagent, the in vivo biotinylation was followed by a 10 min washing step with 50 mM Tris, 10% (w/v) dextran-40, in PBS, pH 7.4, prewarmed to 38° C. During perfusion with biotinylation reagent (and during the first three minutes of the following perfusion with quenching solution)

the region around the heart was washed with 50 mM Tris in PBS, pH 7.4 (38° C.), to quench out-flowing unreacted biotinylation reagent and avoid undesired labelling of molecules at the organ surfaces. After perfusion, organs and tumours were excised and specimens were either freshly snap-frozen for preparation of organ homogenates or embedded in cryoembedding compound (Microm, Walldorf, Germany) and frozen in isopentane in liquid nitrogen for preparation of cryosections for histochemical analysis. Unperfused mice were used as negative controls for the proteomic analysis.

Preparation of Protein Extracts for Proteomic Analysis

Specimens were resuspended in 40 µl per mg tissue of lysis buffer (2% SDS, 50 mM Tris, 10 mM EDTA, Complete E proteinase inhibitor cocktail (Roche Diagnostics, Mannheim, Germany) in PBS, pH 7.4) and homogenized using an Ultra-Turrax T8 disperser (IKA-Werke, Staufen, Germany). Homogenates were sonicated using a Vibra-cell (Sonics, New Town, Conn., USA), followed by 15 min incubation at 99° C. and 20 min centrifugation at 15000×g. The supernatant was used as total protein extract. Protein concentration was determined using the BCA Protein Assay Reagent Kit (Pierce).

Purification of Biotinylated Proteins

For each sample, 960 µl streptavidin-sepharose (Amersham Biosciences, Uppsala, Sweden) slurry were washed three times in buffer A (NP40 1%, SDS 0.1% in PBS), pelleted and mixed with 15 milligrams of total protein extract. Capture of biotinylated proteins was allowed to proceed for 2 h at RT in a revolving mixer. The supernatant was removed and the resin washed three times with buffer A, two times with buffer B (NP40 0.1%, NaCl 1 M in PBS), and once with 50 mM ammonium bicarbonate. Finally, the resin was resuspended in 400 µl of a 50 mM solution of ammonium bicarbonate and 20 µl of sequencing grade modified porcine trypsin (stock solution of 40 ng/µl in 50 mM ammonium bicarbonate) (Promega, Madison, Wis., USA) were added. Protease digestion was carried out overnight at 37° C. under constant agitation. Peptides were desalted, purified and concentrated with C18 microcolumns (ZipTip C18, Millipore, Billerica, Mass., USA). After lyophilisation peptides were stored at −20° C.

Nano Capillary-HPLC with Automated Online Fraction Spotting onto MALDI Target Plates Tryptic peptides were separated by reverse phase high Performance liquid chromatography (RP-HPLC) using an UltiMate nanoscale LC system and a FAMOS microautosampler (LC Packings, Amsterdam, The Netherlands) controlled by the Chromeleon software (Dionex, Sunnyvale, Calif., USA). Mobile phase A consisted of 2% acetonitrile and 0.1% trifluoroacetic acid (TFA) in water, mobile phase B was 80% acetonitrile and 0.1% TFA in water. The flow rate was 300 nl/min. Lyophilized peptides derived from the digestion of biotinylated proteins affinity purified from 1.5 mg of total protein were dissolved in 5 µl of buffer A and loaded on the column (inner diameter: 75 µm, length 15 cm, filled with C18 PepMap 100, 3 µm, 100 Å beads; LC Packings). The peptides were eluted with a gradient of 0-30% B for 7 min, 30-80% B for 67 min, 80-100% B for 3 min and 100% B for 5 min; the column was equilibrated with 100% A for 20 min before analyzing the next sample. Eluting fractions were mixed with a solution of 3 mg/ml cyano-4-hydroxy cinnamic acid, 277 pmol/ml neurotensin (internal standard), 0.1% TFA, and 70% acetonitrile in water and deposed on a 192-well MALDI target plate using an on-line Probot system (Dionex). The flow of the MALDI-matrix solution was set to 1.083 µl/min. Thus, each fraction collected during 20 s contained 361 nl MALDI-matrix solution and 100 nl sample. The end-concentration of neurotensin was 100 fmol per well.

MALDI-TOF/TOF Mass Spectrometry

MALDI-TOF/TOF mass spectrometric analysis was carried out with the 4700 Proteomics Analyzer (Applied Biosystems, Framingham, Mass., USA). For precursor ion selection, all fractions were measured in MS mode before MS/MS was performed. A maximum of 15 precursors per sample spot were selected for subsequent fragmentation by collision induced dissociation. Spectra were processed and analyzed by the Global Protein Server Workstation (Applied Biosystems), which uses internal MASCOT (Matrix Science, London, UK) software for matching MS and MS/MS data against databases of in silico digested proteins. The data obtained were screened against a mouse database downloaded from the NCBI homepage (http://www.ncbi.nlm.nih.gov/). Protein identifications, performed by means of the MASCOT software, were considered to be correct calls within the 95% confidence interval for the best peptide ion.

MALDI-TOF and MALDI-TOF/TOF mass spectrometric analyses were carried out using the 4700 Proteomics Analyzer (Applied Biosystems). Peptide masses were acquired over a range from 750 to 4000 m/z, with a focus mass of 2000 m/z. MS spectra were summed from 2000 laser shots from an Nd:YAG laser operating at 355 nm and 200 Hz. An automated plate calibration was performed using five peptide standards (masses 900-2400 m/z; Applied Biosystems) in six calibration wells. This plate calibration was used to update the instrument default mass calibration, which was applied to all MS and MS/MS spectra. Furthermore, an internal calibration of each MS spectrum using the internal standard peptide added to the MALDI matrix was performed. A maximum of 15 precursors per sample well with a signal-to-noise ratio of >100 was automatically selected for subsequent fragmentation by collision induced dissociation. MS/MS spectra were summed from 2500 to 5000 laser shots. Spectra were processed and analyzed by the Global Protein Server Workstation (Applied Biosystems), which uses internal MASCOT (Matrix Science) software for matching MS and MS/MS data against databases of in-silico digested proteins. The MASCOT search parameters were (i) a mouse database downloaded from the European Bioinformatics Institute (EBI) homepage on the 9Sep. 2006 (ftp.ebi.ac.uk/pub/databases/SPproteomes/fasta/proteomes/59.M_musculus.fasta.gz); (ii) enzyme: trypsin and semi-trypsin; (iii) allowed number of missed cleavages: 1; (iv) variable posttranslational modifications: methionine oxidation; (v) peptide tolerance: ±30 ppm; (vi) MS/MS tolerance: ±0.2 Da; (vii) peptide charge: +1; (viii) minimum ion score C.I. % for peptides: 95 and (ix) maximum peptide rank: 1. Furthermore, an MS/MS peak filtering with the following parameters was used: (i) mass range: 60 Da to 20 Da below precursor mass; (ii) minimum signal-to-noise ratio: 6; (iii) peak density filter: maximum 30 peaks per 200 Da and (iv) maximum number of peaks per spectrum: 65.

Antibodies

The isolation of the anti-ED-B antibody fragment scFv (L19) has been previously described (Pini et al. 1998). The parent anti-ED-A antibody was isolated from the ETH-2 library using published procedures (Giovannoni, Nucleic. Acid Research, 2001, 29(5):E27). The affinity maturation of the parent anti-ED-A antibody, yielding the high affinity anti-ED-A antibodies, is described in the following section.

Affinity Maturation of the Parent Anti-ED-A Antibody

The parent anti-ED-A antibody (an ETH-2-derived antibody) was used as template for the construction of an affinity maturation library. Sequence variability in the VH CDR1 (DP47 germline) and VL CDR1 (DPK22 germline) of the library was introduced by PCP using partially degenerate primers 5'-CTGGAGCCTGGCGGACCCAGCTCATMN-NMNNMNNGCTAAAGGTGAAT CCAGA-3' (SEQ ID NO: 17) for VH and 5'-CCAGGTTTCTGCTGGTACCAG-GCTAA MNNMNNMNNGCTAACACTCTGACTGGC-CCTGC-3' (SEQ ID NO: 18) for VL (all oligonucleotides were purchased from Operon Biotechnologies, Cologne, Germany), in a process that generates random mutations at positions 31, 32 and 33 of the VH CDR1 and at positions 31, 31a and 32 of the VL CDR1. VHVL combinations were assembled in scFv format by PCR assembly using the primers LMB3long (5'-CAGGAAACAGCTATGACCATGATTAC-3') (SEQ ID NO: 19) and fdseqlong (5'-GACGTTAGTAAAT-GAATTTTCTGTATGAGG-3') (SEQ ID NO: 20), using gel-purified VH and VL segments as templates. The assembled VH-VL fragments were doubly digested with NcoI/NotI and cloned into NcoI/NotI-digested pHEN1 phagemid vector (Hoogenboom et al., 1991). The resulting ligation product was electroporated into electrocompetent E. coli TG-1 cells according to (Viti et al., 2000), giving rise to a library containing $1.5 \times 10^7$ individual antibody clones, which was screened for antibodies which bind ED-A with improved affinity.

Selection of Anti-ED-A Antibodies

The antibody library described above was screened for antibodies which bound ED-A with a greater affinity than the parent anti-ED-A antibody using BIAcore analysis. The antigen (11A12) used in the BIAcore analysis contained the ED-A domain of human fibronectin and has the following amino acid sequence (SEQ ID NO: 120):

MRSYRTEIDKPSQMQVTDVQDNSISVKWLPSSSPVTGYRVTTTPKNGPGP

TKTKTAGPDQTEMTIEGLQPTVEYVVSVYAQNPSGESQPLVQTAVTNIDR

PKGLAFTDVDVDSIKIAWESPQGQVSRYRVTYSSPEDGIHELFPAPDGEE

DTAELQGLRPGSEYTVSVVALHDDMESQPLIGTQSTAIPAPTDLKFTQVT

PTSLSAQWTPPNVQLTGYRVRVTPKERTGPMKEINLAPDSSSVVVSGLMV

ATKYEVSVYALKDTLTSRPAQGVVTTLENVRSHHHHHH

The nucleotide sequence of antigen (11A12) (SEQ ID NO: 121) is as follows:

atgagatcctaccgaacagaaattgacaaaccatcccagatgcaagtgac cgatgttcaggacaacagcattagtgtcaagtggctgccttcaagttccc ctgttactggttacagagtaaccaccactcccaaaaatggaccaggacca acaaaaactaaaactgcaggtccagatcaaacagaaatgactattgaagg cttgcagcccacagtggagtatgtggttagtgtctatgctcagaatccaa gcggagagagtcagcctcttccatcaaaattgcttgggaaagcccacagg ggcaagtttccaggtacagggtgacctactcgagccctgaggatggaatc catgagctattccctgcacctgatggtgaagaagacactgcagagctgca aggcctcagaccgggttctgagtacacagtcagtgtggttgccttgcacg atgatatggagagccagcccctgattggaacccagtccacagctattcct gcaccaactgacctgaagttcactcaggtcacacccacaagcctgagcgc ccagtggacaccacccaatgttcagctcactggatatcgagtgcgggtga cccccaaggagaagaccggaccaatgaaagaaatcaaccttgctcctgac agctcatccgtggttgtatcaggacttatggtggccacccaaatatgaagt gagtgtctatgctcttaaggacactttgacaagcagaccagctcagggag ttgtcaccactctggagaatgtcagatctcatcaccatcaccatcactaa The nucleotide sequence of the antigen was amplified by FOR using primers containing BamHI and BglII restriction sites at the 5' and 3' respectively. The resulting PCR product and the vector pQE12 (QIAGEN) were digested with BamHI and BglII restriction endonuclease and subsequently ligated in a reaction containing a ratio of insert to vector of 3:1. The resulting vector was sequenced to check that the sequence was correct.

The antigen was prepared as follows:

A TG1 electrocompetent Preculture in 10 ml 2TY, Amp, 1% Glucose was electroporated in the presence of 1 µl of a DNA miniprep of 11A12. The pre-culture was then diluted 1:100 (8 ml in 800 ml of 2TY, Amp, 0.1% Glucose) and grown to an OD600 of 0.4-0.6 and then induced with IPTG over night. The following day the cells were spun down and the supernatant filtered (Millipore 0.22 µm). After centrifugation and clarification of the culture broth, 11A12 was purified using a Hitrap column on FPLC. The Ni/column was regenerated as follows: the column was rinsed with 5 column volumes (CV) H2O followed by application of 3CV 0.5 M EDTA/0.2 M Tris pH 8 to wash the old Nickel out from the column. This was followed by rinsing of the column with 5CV H2O. The column was then reloaded with 2CV 100 mM NiSO4 followed by rinsing of the column with several CVs H2O. The column was then equilibrated with 5CV lysis buffer (20 mM imidazol/250 mM NaCl/PBS pH 7.4). The cell lysate was filtered (Millipore 0.45 µm) and loaded onto the column (manually). The column was then put back on FPLC and the lysis buffer left to flow until the UV signal was stable (constant), about 3 CV. The elution program was then started: Gradient from 0% to 100% of Elution Buffer (400 mM imidazol/250 mM NaCl/PBS pH 7.4) in 5CV. The fractions containing the eluted antigen were pooled and dialysed in PBS over night.

Expression and Purification of the Anti-ED-A Antibodies

The anti-ED-A antibodies were expressed and purified as follows: A TG1 electrocompetent Preculture in 10 ml 2TY, Amp, 1% Glucose was electroporated in the presence of 1 µl of a DHA miniprep of one of the anti-ED-A antibodies. The pre-culture was then diluted 1:100 (8 ml in 800 ml of 2TY, Amp, 0.1% Glucose) and grown to an OD600 of 0.4-0.6 and then induced with IPTG over night. The following day the cells were spun down and the supernatant filtered (Millipore 0.22 µm). The scFv were purified on a Protein A-Sepharose column and Triethylemmine was used to elute the scFvs from the column. The fractions containing the eluted scFvs were dialysed in PBS over night at 4° C. The scFv fractions were then put on a Superdex 75 column with PBS flowing at 0.5 ml/min and 0.25 ml fractions collected. The monomeric fractions were used for BIAcore analysis.

BIAcore Analysis 1

The BIAcore Chip was flushed overnight at a flow rate of 5 µl/min with HBS-EP buffer BIACORE, 0.01 M Hepes pH 7.4, 0.15 M NaCl, 3 mM EDTA, 0.005% surfactant P20 (same buffer used for the assay). The antigen (11A12) was diluted to a concentration of 50 µg/ml in acetate buffer (pH 4.0) and the COOH groups on the chip were activated by injection of 50 µl of a mix of N-Hydroxy Succinimmide (NHS) and ethyl-N-(dimethylaminopropyl)-carbodiimide (EDC). 40 µl of the 11A12 antigen were injected onto the chip and the residual free COOH groups were blocked with 30 µl of ethanolamine. After a 0.22 µm filtration, 20 µl of each individual bacterial supernatant were injected onto the chip and interaction with the antigen was monitored in real time.

BIAcore Analysis 2

The $k_{on}$, $k_{off}$ and $K_D$ of the parent anti-ED-A antibody and anti-ED-A antibodies B2, C5, D5, C8, F8, B7 and G9 were evaluated using Surface Plasmon Resonance. The chip was equilibrated over night with the same buffer used during the assay at a buffer flow rate of 5 µl/min. The whole coating procedure was performed at this flow rate. The antigen 11A12 was diluted 1:25 with acetate buffer pH 4.00 (provided by BIACORE) to a final concentration of 20 µg/ml. The NHS and EDC were then mixed and 50 µl injected to activate the COOH groups on the CM5 chip. This was followed by injection of 40 µl of the antigen (this lasts about 40"). Then 30 µl of Ethanolammine were injected in order to block the reactivity of eventual free COOH.

Each sample was assayed at a flow rate 20 µl/min. 20 µl of undiluted monomeric protein (as it comes out from the gel filtration) was injected. The dissociation time was left to run for about 200". Then 10 µl of HCl 10 mM was injected to regenerate the chip. The injection of monomeric protein was repeated at different dilutions, i.e. 1:2 dilution (in PBS) followed by regeneration with HCl. This was followed by a third injection of the protein, at a dilution of 1:4 followed again by regenartion with HCl. The $k_{on}$, $k_{off}$ and KD values for each anti-ED-A antibody were evaluated using the BIAevaluation software.

Histochemistry

In order to verify successful in vivo biotinylation, staining of biotinylated structures after was performed as described in (Rybak et al. 2005). Section (10 µm) were cut from freshly-frozen specimens, fixed with acetone, incubated successively with streptavidin:biotinylated alkaline phosphatase complex (Biospa, Milano, Italy) and with Fast-Red TR (Sigma) [in the presence of 1 mM Levamisole to inhibit endogenous alkaline phosphatase] and counterstained with Hematoxylin solution (Sigma).

Immunohistochemical staining with scFv-antibodies, which carried a FLAG-tag, was performed as described earlier (see, e.g., (Brack et al. 2006)). In brief, sections were incubated with the scFv fragments (final concentration, 2-10 µg/mL) and with monoclonal anti-Flag antibody M2 simultaneously. Bound antibodies were detected with rabbit anti-mouse immunoglobulin antibody (Dakocytomation, Glostrup, Denmark) followed by mouse monoclonal alkaline phosphatase-anti-alkaline phosphatase complex (Dakocytomation). Fast Red (Sigma) was used as phosphatase substrate, and sections were counterstained with hematoxylin (Sigma).

All sections were mounted with Glycergel (DakoCytomation, Glostrup, Denmark) and analyzed with an Axiovert 5100 TV microscope (Carl Zeiss, Feldbach, Switzerland) using the Axiovision software (Carl Zeiss).

In Vivo Targeting with Anti-ED-A Antibody

The parent anti-ED-A antibody scFv was labelled with the commercially available infrared fluorophore derivative Alexa Fluor 750 carboxylic acid succinididyl ester (Invitrogen) according to the provider's protocol. The labelled antibody was separated from the unreacted dye by gel filtration using a PD-10 column (GE Healthcare). The degree of labelling, estimated according to the Invitrogen labelling protocol, was 5 dye molecules per antibody molecule. The Alexa 750-labeled parent anti-ED-A scFv antibody (in a final concentration of 0.3 mg/ml) was injected (200 µl/mouse, i.e. 60 µg antibody/mouse) in the tail vein of Sv190 mice 3 weeks after injection of F9DR tumour cells. Mice organs were excised 6 hours after injection of the labelled antibody and imaged with a home-built infrared fluorescence imager (Birchler et al. 1999) equipped with a tungsten halogen lamp, excitation and emission filters specific for Alexa 750, and a monochrome CCD camera.

Biodistribution of F8 Diabody

The F8 diabody comprises the same VH and VL domains as anti-ED-A antibody F8, e.g. as employed in scFv format. The F8 diabody and the anti-ED-A scFv F8 have different linker sequences between the VH and the VL domains. The amino acid sequence of the F8 diabody linker is GSSGG (SEQ ID NO: 28) (nucleotide sequence: gggtccagtggcggt [SEQ ID NO: 29]). Therefore, the F8 diabody linker sequence is five amino acids long, while in the anti-ED-A scFv F8 the linker is 20 amino acids long (see SEQ ID NO: 11). The reduction in the length of the linker between the VL and VH domains, means that intermolecular rather intramolecular pairing of VL and VH domains is favoured. Consequently, the VL domain of one F8 polypeptide is more likely to pair with the VH domain of another F8 polypeptide than it is to pair with the VH domain of the same F8 polypeptide.

The F8 diabody was expressed in *E. coli* TG1 cells as follows: DNA encoding the F8 diabody was introduced into electrocompetent *E. coli* TG1 cells using electroporation. The electroporated *E. coli* cells were precultured in 10 ml 2YT medium, Amp, 1% Glucose. The preculture was diluted 1:100 into 800 ml 2YT medium, Amp, 0.1% Glucose and the culture grown to a density (OD600 nm) of 0.6. Expression of the F8 diabody was then induced using 1 mM of IPTG.

The expressed F8 diabody was labelled with $^{125}$I as follows: 10 µl of sterile PBS was added into an iodogen tube (coated with 50 µl 0.1 mg/ml iodogen in Chloroform) followed by addition of 2 µl $^{125}$I sodium iodide (~200 µCi) and incubation at room temperature (RT) for 5 min.

400 µl of F8 diabody at an OD 0.2 (~60 µg) were then added to the iodogen tube and incubated at RT for 25 min. 1/100 of this mixture was collected in order to measure the radioactivity contained in the mixture (referred to as 'INPUT'). The labelled F8 diabody was then loaded onto a size exclusion chromatography column (PD10: Sephadex G-25 M, GE Healthcare) in order to separate the iodinated F8 diabody from the free iodine. The radioactivity of the collected iodinated F8 diabody was measured and the percentage of iodine incorporated into the F8 diabody calculated (CPM [counts per minute] of iodinated F8 diabody/CPM INPUT) to be between 30-40%.

Four F9 tumour bearing mice were put on Lugol for 2 days (600 µl into 300 ml) in order to block the thyroid and each mouse injected intravenously with 200 µl of the iodinate F8 diabody (about 5-8 µg iodinate F8 diabody [18 µCi] per mouse). After 24 hours the mice were sacrificed and tumour, liver, lung, spleen, heart, kidney, intestine, tail and blood were removed (referred to collectively herein in this context as mouse 'tissues') and used for radioactive counting. The level of radioactivity in each tissue sample was measured using a Perkin gamma-counter. The 'output' was calculated by dividing the percentage of the injected dose (in CPM) by the weight of the tissue (in grams)(% ID/g).

Results

Identification of Differentially Expressed Proteins and Splice Variants

The perfusion-based chemical proteomic methodology used for the comparative analysis of accessible proteins in liver and in F9 liver metastases (Terrana et al. 1987) is depicted in FIG. 1A. These tumours develop large metastatic foci on the surface and inside the mouse liver (FIG. 1B). Under terminal anaesthesia, tumour-bearing mice were perfused with 15 ml of a 1.8 mM solution of sulfosuccinimidyl-6-[biotin-amido]hexanoate (1 mg/ml) in PBS, pH 7.4, supplemented with 10% Dextran-40 as plasma expander. The procedure, which typically lasted 10 minutes, allowed the removal of blood from all the organs of the major circulation and the selective biotinylation of accessible proteins, both on the luminal and abluminal aspects of blood vessels. Virtually all blood vessels of F9 liver metastases were efficiently and selectively labelled with this procedure, as confirmed by histochemical staining with a streptavidin-alkaline phosphatase conjugate (FIG. 1C). In the normal liver, blood vessels were strongly stained, but labelling of some sinusoids was also detected, compatibly with the physiological filter function of the liver (FIG. 1C). The in vivo biotinylation was quenched by perfusion with a solution containing primary amines. Subsequently, specimens of liver metastases were excised from the liver, homogenized and used for the recovery of biotinylated proteins in the presence of the strong detergent SDS by affinity chromatography on streptavidin resin (FIG. 1A). In order to minimize the risk of diffusion of metastatic proteins in the host liver, liver from in vivo biotinylated healthy mice was used for the study of the normal liver vasculature. The use of host liver from F9 tumour mice would have also been problematic because of the little residual healthy tissue and because it would have been difficult to exclude macroscopically the absence of micrometastases. In total, samples from 7 in vivo biotinylated healthy mice and 9 in vivo biotinylated F9 tumour-bearing mice were used for the proteomic analysis. In addition, specimens from 2 healthy and 3 metastases-bearing non-biotinylated mice were used as negative controls. Stringent washing procedures and on-resin tryptic digestion of streptavidin captured proteins from F9 metastases and normal liver (processed in parallel) yielded a collection of peptides, which could be separated, identified and compared using nano-HPLC and MALDI-TOF/TOF mass spectrometric procedures (Roesli et al., 2006).

In total, 1291 different peptides were identified (>95% Mascot confidence level) which were grouped by the Mascot software to 480 different peptide sets. A few of these peptide sets were also found in negative control samples from non-biotinylated mice (like carboxylases which carry endogenous biotin as a co-factor, keratins as contaminants, or very abundant proteins like serum albumin). Of the residual 435 identified peptide sets, 331 could be annotated by the Mascot software unambiguously to a single protein, while 104 peptide sets were annotated to multiple (in total to 358) proteins. In most cases, multiple proteins annotated to the same peptide set belong to a related protein family (e.g., immunoglobulins) or can even be the same proteins with different database entries. Of the 435 different peptide sets, 117 were exclusively found in metastasis specimens, 193 only in healthy liver specimens and 125 in both types of tissues. For example, peptides matching to fibronectin (National Center for Biotechnology Information [NCBI] accession number P11276) were found in four healthy liver specimens and eight metastasis specimens.

Proteins found in both the healthy liver and metastasis specimens (e.g. fibronectin) may be present at substantially different levels in the two samples. If this was the case, this should be reflected in the number of specimens in which the proteins were detected, and/or in the number of peptides (as well as normalized peptide signal intensity; (Scheurer et al. 2005, Scheurer et al. 2005)) observed in the liver and metastasis samples. For instance, 38 tryptic peptides from fibronectin (NCBI accession number P11276) were found only in metastasis specimens, while one peptide was found only in healthy liver specimens. Eleven peptides were found in both types of specimens.

The striking abundance of fibronectin-derived peptides detected in liver metastases, in spite of the fact that liver is the site of fibronectin biosynthesis, prompted us to investigate differences in relative abundance of fibronectin-derived peptides and the over-expression of alternatively spliced domains. Table 1 lists all fibronectin peptides identified in the proteomic analysis. Mouse fibronectin, contains two type-III globular extra-domains which may undergo alternative splicing: ED-A and ED-B (ffrench-Constant 1995, Hynes 1990, Kaspar et al. 2006). In addition, the IIICS segment undergoes different splicing patterns in mice and humans. Interestingly, all three ED-A-derived peptides as well as the IIICS-derived peptide were observed only in the tumour samples.

ED-B-derived peptides would not be visible in this analysis due to the fact that ED-B contains no lysine residue and the two arginines give rise to peptides which are too large in size for detection. FIG. 2A shows the location of the peptides identified in tumour specimens (Tumor) and healthy liver specimens (Normal) on the fibronectin domain structure. FIG. 2B shows the relative intensity of normalized MS signals for two fibronectin-derived peptides: IAWESPQGQVSR (SEQ ID NO: 16) which is located within the ED-A domain and FLTTTPNSLLVSWQAPR (SEQ ID NO: 15), which is located in domain 14. The latter peptide was more abundant in the metastasis specimens, but was clearly detectable also in the normal liver counterpart. By contrast, ED-A-derived peptides gave strong signals in the metastasis samples, but were completely undetectable (i.e., >100-fold lower signal) in normal liver.

Immunohistochemistry

Figure 4:
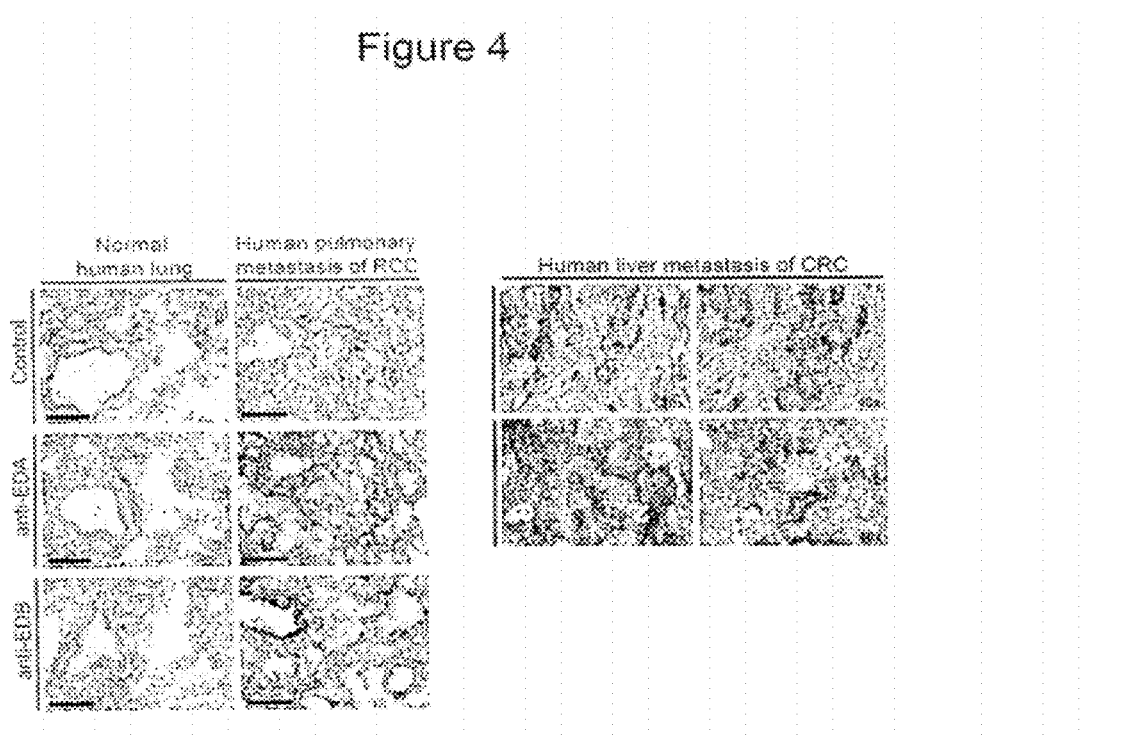
FIG. 4: Shows ED-A expression in human metastases. The flag-tagged parent anti-ED-A antibody was used to asses the expression of ED-A in human metastases by immunohistochemistry. While no positive staining was detectable in negative controls (Control) omitting the flag-tagged parent anti-ED-A antibody and only a very weak background staining was observed on human normal lung tissue sections (Normal human lung) with the flag-tagged parent anti-ED-A antibody, human pulmonary metastases (Human pulmonary metastasis of RCC [renal cell carcinoma]) were strongly positively stained with the flag-tagged parent anti-ED-A antibody (anti-EDA) as shown by the darker lines and shades. The staining pattern of the flag-tagged parent anti-ED-A antibody is mainly vascular and is similar to the staining pattern observed with the flag-tagged anti-ED-B scFv(L19) antibody (anti-EDB) which recognizes the fibronectin extra-domain B, a well established marker of neovascular structures. Similar results were obtained by immunohistochemical analysis of human liver metastases of colorectal carcinoma (Human liver metastasis of CRC) with the flag-tagged parent anti-ED-A antibody. The flag-tagged parent anti-ED-A antibody reveals a strong vascular and stromal staining pattern human liver metastases of colorectal carcinoma.

The most striking discrimination between liver structures and metastatic neovasculature was observed for the ED-A and ED-B domains of fibronectin. In both cases, a strong and specific staining of the metastatic blood vessels was observed, while normal liver and virtually all normal organs (exception made for the endometrium in the proliferative phase and some vessels of the ovaries) scored negative in this immunohistochemical analysis (FIG. 3A). Importantly, ED-A was also found to be strongly expressed in the neovasculature of human lung metastases and liver metastases (FIG. 4).

In Vivo Targeting

In order to test the usefulness of ED-A as a target for ligand-based vascular targeting of metastases, an in vivo targeting experiment using near-infrared fluorescence imaging was performed. The parent anti-ED-A scFv antibody was labelled with Alexa Fluor 750 and injected intravenously into F9 metastases-bearing mice. Near-infrared fluorescence imaging of the excised organs revealed a striking accumulation of the targeting agent in the metastatic lesions (FIG. 3B).

Selection of Anti-ED-A Antibodies

BIAcore Analysis 1

The BIAcore analysis produced a graph for each anti-ED-A antibody which was analysed to deduce the affinity of an antibody for the antigen as follows: The x axis of each graph corresponds to time and the y axis corresponds to Resonance Units (a measure which indicates the binding affinity of the tested antibody for the antigen coated onto the BIAcore chip). Each graph showed 3 peaks and 1 dip which correspond to changes of buffer and are therefore irrelevant for the interpretation of the results.

The ascending part of each graph represents the association phase. The steeper the curve in this part of the graph, the faster the association of the antibody with the antigen. The descending part of each graph represents the dissociation phase of the antibody from the antigen. The flatter the curve in this part of the graph is, the slower the dissociation of the antibody from the antigen.

Anti-ED-A antibodies H1, B2, C5, D5, E5, C8, F8, F1, B7, E8 and G9 all showed a flatter dissociation curve than the parent anti-ED-A antibody from which they were derived, indicating that they bind ED-A, and hence also A-FN, with a greater affinity than the parent anti-ED-A antibody. The graphs for antibodies E5, F1, F8 and H1 showed the flattest dissociation curves of all the anti-ED-A antibodies tested. The association curves of antibodies H1, C5, D5, E5, C8, F8 and F1 were flatter than that observed for the parent anti-ED-A antibody while the association curve observed for antibodies B2, B7, E8 and G9 was as steep as the association curve observed for the parent anti-ED-A antibody. However, as bacterial supernatants of IFTG-induced *E. coli* TG-1 cells were used for the BIAcore analysis of antibodies H1, B2, C5, D5, E5, C8, F8, F1, B7, E8 and G9, the concentration of the tested antibody samples was unknown but most probably lower than the concentration of the parent anti-ED-A antibody sample used for comparison. Consequently, the association curve of antibodies H1, B2, C5, D5, E5, C8, F8, F1, B7, E8 and G9 may be artificially low due to the low concentration of antibody in the samples used for the BIAcore analysis. However, as concentration does not significantly affect the dissociation of an antibody from its target antigen in BIAcore analysis, the flat dissociation curves observed for antibodies H1, B2, C5, D5, E5, C8, F8, F1, B7, E8 and G9 show that these antibodies bind ED-A with at least an equal, and probably a higher affinity, than the parent anti-ED-A antibody. Consequently, anti-ED-A antibodies H1, B2, C5, D5, E5, C8, F8, F1, B7, E8 and G9 are extremely likely to give rise to the same or better results when used in the same in vivo and immunohistochemical studies conducted using the parent anti-ED-A antibody as described elsewhere herein. The in vivo and immunohistochemical data obtained using the parent anti-ED-A antibody therefore provides evidence that anti-ED-A antibodies H1, B2, C5, D5, E5, C8, F8, F1, B7, E8 and 09 may be used for the treatment of tumour metastases.

BIAcore Analysis 2

The $k_{on}$, $k_{off}$ and KD values for each anti-ED-A antibody were evaluated using the BIAevaluation software. The $k_{on}$, $k_{off}$ and KD values of the parent anti-ED-A antibody and anti-ED-A antibodies B2, C5, D5, C8, F8, B7 and G9 for antigen 11A12 are detailed in Table 3. Anti-ED-A antibodies B2, C5, D5, C8, F8, B7 and G9 all have a better $K_D$ values for antigen 11A12 than the parent anti-ED-A antibody from which they were derived, indicating that they bind ED-A, and hence also A-FN, with a greater affinity than the parent anti-ED-A antibody. Consequently, anti-ED-A antibodies B2, C5, D5, C8, F8, B7 and G9 are extremely likely to give rise to the same or better results when used in the same in vivo and immunohistochemical studies conducted using the parent anti-ED-A antibody as described elsewhere herein. The in vivo and immunohistochemical data obtained using the parent anti-ED-A antibody therefore provides evidence that anti-ED-A B2, C5, D5, C8, F8, B7 and G9 may be used for the treatment of tumour metastases.

Biodistribution of F8 Diabody

Figure 8:
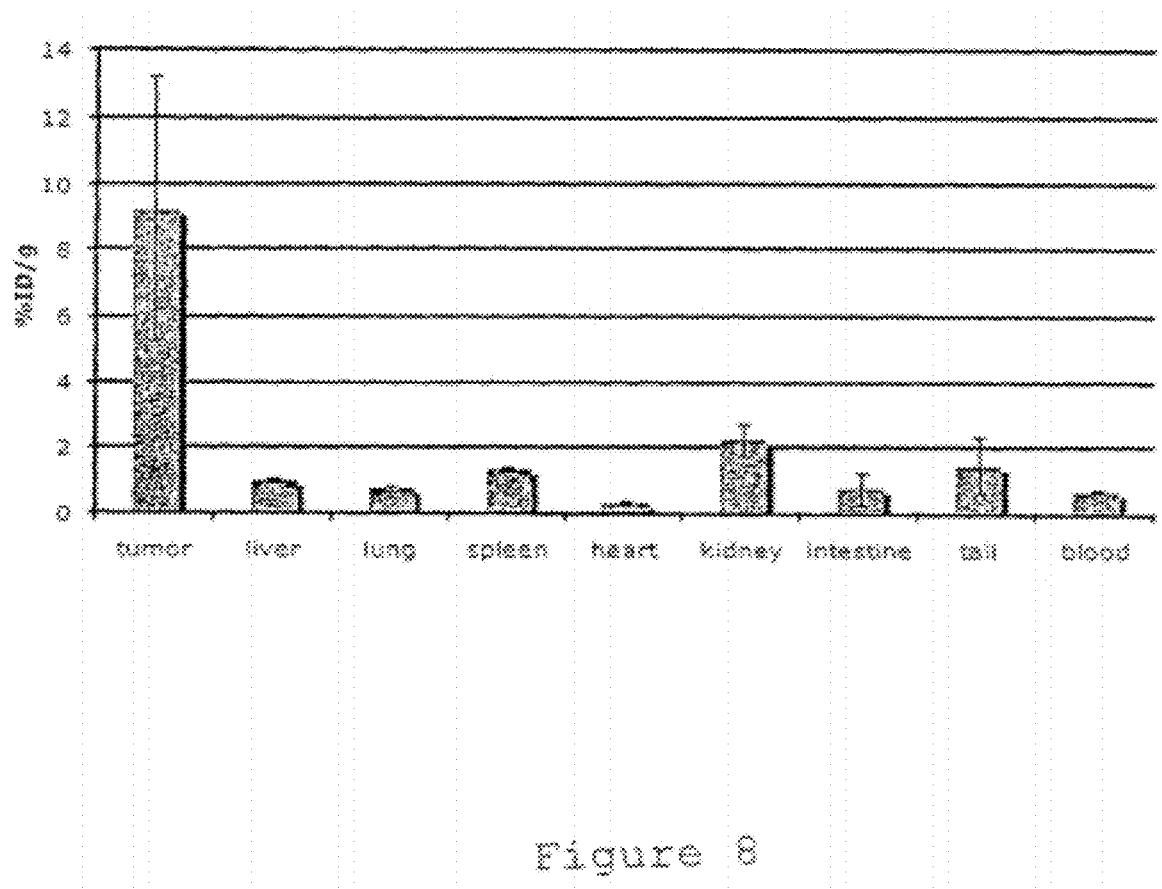
FIG. 8: Shows the biodistribution of the F8 diabody in F9 tumour bearing mice. Four F9 tumour bearing mice were injected intravenously with $I^{125}$ labelled F8 diabody. The mice were sacrificed after twenty four hours and tumour, liver, lung, spleen, heart, kidney, intestine, tail and blood removed. The tumour, liver, lung, spleen, heart, kidney, intestine, tail and blood were then radioactively counted. The percentage (%) of the injected dose (ID) of $I^{125}$ labelled F8 diabody detected per gram (g) of tumour, liver, lung, spleen, heart, kidney, intestine, tail and blood is shown in FIG. 8. The F9 tumours (tumours) contained about four times more of the ID than any of the other mouse tissues analyzed.

The percentage (%) of the injected dose (ID) of $I^{125}$ labelled (iodinated) F8 diabody detected per gram (g) of mouse tissue was very similar for the liver, lung, spleen, heart, kidney, intestine, tail and blood and all, with the exception of the kidney, showed less than 2% ID/g (FIG. 8). In contrast, the F9 tumours contained on average about four times more of the ID than any of the other mouse tissues analyzed (FIG. 8). This demonstrates that the F8 diabody was selectively targeted to the F9 mouse tumours. The percentage of the ID detected in the other tissues most likely represents background load of F8 diabody present in the mice or non-specific labelling of the other mouse tissues. As described elsewhere herein, the biodistribution experiment was performed using four mice and although the percentage of the ID detected per mouse tissue varied (see error bars in FIG. 8) the percentage of F8 diabody detected in the F9 tumours was consistently higher than in any of the other mouse tissues tested.

The biodistribution study was conducted on F9 primary tumours, and the results indicate that the anti-ED-A antibodies in accordance with the present invention are selectively targeted to tumour tissue in vivo. The results provide further indication that the anti-ED-A antibodies of the present invention can be used to achieve the same or better results when used in the same in vivo and immunohistochemical studies conducted using the parent anti-ED-A antibody as described elsewhere herein.

Sequencing

Anti-ED-A antibodies H1, B2, C5, D5, E5, C8, F8, F1, B7, E8 and G9 are all scFv antibodies and were sequenced using conventional methods. The nucleotide sequence of the anti-ED-A antibody H1 is shown in FIG. 6. The amino acid sequence of the anti-ED-A antibody H1 is shown in FIG. 7.

Preferred nucleotide sequences encoding VH and/or VL of anti-ED-A antibodies B2, C5, D5, E5, C8, F8, F1, B7, E8 and G9 are identical to nucleotide sequences encoding VH and/or VL of anti-ED-A antibody H1, except that the nucleotide sequences encoding the H1 CDR1s of the light (VL) and heavy (VH) chain are substituted with the nucleotide sequences encoding the light (VL) and heavy (VH) chain CDR1s listed in Table 2 for the respective antibody.

Some preferred nucleotide sequences encoding the VH and/or VL domains of anti-ED-A F8 diabody are identical to the nucleotide sequences encoding VH and/or VL domains of anti-ED-A antibody H1, except that the nucleotide sequences encoding the H1 CDR1s of the light (VL) and heavy (VH) chain are substituted with the nucleotide sequences encoding the light (VL) and heavy (VH) chain CDR's listed in Table 2 for anti-ED-A antibody F8. A preferred nucleotide sequence encoding the linker linking the VH and VL domains of the anti-ED-A F8 diabody is gggtccagtggcggt (SEQ ID NO: 29).

Anti-ED-A antibodies B2, C5, D5, E5, C8, F8, F1, B7, E8 and G9 have identical amino acid sequences to anti-ED-A antibody H1, except that the amino acid sequences of the H1 CDR1s of the light (VL) and heavy (VH) chain are substituted with the amino acid sequences of the light (VL) and heavy (VH) chain CDR1s listed in Table 2 for the respective antibody. The amino acid sequences of the VH and VL domains of anti-ED-A F8 diabody are identical to the amino acid sequences of anti-ED-A antibody H1, except that the amino acid sequences of the H1 CDR1s of the light (VL) and heavy (VH) chain are substituted with the amino acid sequences of the light (VL) and heavy (VH) chain CDR1s listed in Table 2 for anti-ED-A antibody F8, and the amino acid sequence of the linker in H1 is substituted with the linker amino acid sequence GSSGG (SEQ ID NO: 28).

The amino acid sequence of the anti-ED-A antibody B2 VH domain (SEQ ID NO: 21) is identical to the amino acid sequence of the VH domain of anti-ED-A antibody H1 except that SEQ ID NO: 23 is substituted for the VH CDR1 of H1.

The amino acid sequence of the anti-ED-A antibody C5 VH domain (SEQ ID NO: 41) is identical to the amino acid sequence of the VH domain of anti-ED-A antibody H1 except that SEQ ID NO: 43 is substituted for the VH CDR1 of H1.

The amino acid sequence of the anti-ED-A antibody D5 VH domain (SEQ ID NO: 51) is identical to the amino acid sequence of the VH domain of anti-ED-A antibody H1 except that SEQ ID NO: 53 is substituted for the VH CDR1 of H1.

The amino acid sequence of the anti-ED-A antibody E5 VH domain (SEQ ID NO: 61) is identical to the amino acid sequence of the VH domain of anti-ED-A antibody H1 except that SEQ ID NO: 63 is substituted for the VH CDR1 of H1.

The amino acid sequence of the anti-ED-A antibody C8 VH domain (SEQ ID NO: 71) is identical to the amino acid sequence of the VH domain of anti-ED-A antibody H1 except that SEQ ID NO: 73 is substituted for the VH CDR1 of H1.

The amino acid sequence of the anti-ED-A antibody F8 VH domain (SEQ ID NO: 81) is identical to the amino acid sequence of the VH domain of anti-ED-A antibody H1 except that SEQ ID NO: 83 is substituted for the VH CDR1 of H1. The VH domains of the anti-ED-A F8 diabody have the same amino acid sequence as VH domain of the anti-ED-A scFv antibody F8 (i.e. SEQ ID NO: 81).

The amino acid sequence of the anti-ED-A antibody F1 VH domain (SEQ ID NO: 91) is identical to the amino acid sequence of the VH domain of anti-ED-A antibody H1 except that SEQ ID NO: 93 is substituted for the VH CDR1 of H1.

The amino acid sequence of the anti-ED-A antibody B7 VH domain (SEQ ID NO: 101) is identical to the amino acid sequence of the VH domain of anti-ED-A antibody H1 except that SEQ ID NO: 103 is substituted for the VH CDR1 of H1.

The amino acid sequence of the anti-ED-A antibody E8 VH domain (SEQ ID NO: 111) is identical to the amino acid sequence of the VH domain of anti-ED-A antibody H1 except that SEQ ID NO: 113 is substituted for the VH CDR1 of H1.

The amino acid sequence of the anti-ED-A antibody G9 VH domain (SEQ ID NO: 31) is identical to the amino acid sequence of the VH domain of anti-ED-A antibody H1 except that SEQ ID NO: 33 is substituted for the VH CDR1 of H1.

The amino acid sequence of the anti-ED-A antibody B2 VL domain (SEQ ID NO: 22) is identical to the amino acid sequence of the VL domain of anti-ED-A antibody H1 except that SEQ ID NO: 26 is substituted for the VL CDR1 of H1.

The amino acid sequence of the anti-ED-A antibody O5 VL domain (SEQ ID NO: 42) is identical to the amino acid sequence of the VL domain of anti-ED-A antibody H1 except that SEQ ID NO: 46 is substituted for the VL CDR1 of H1.

The amino acid sequence of the anti-ED-A antibody D5 VL domain (SEQ ID NO: 52) is identical to the amino acid sequence of the VL domain of anti-ED-A antibody H1 except that SEQ ID NO: 56 is substituted for the VL CDR1 of H1.

The amino acid sequence of the anti-ED-A antibody E5 VL domain (SEQ ID NO: 62) is identical to the amino acid sequence of the VL domain of anti-ED-A antibody H1 except that SEQ ID NO: 66 is substituted for the VL CDR1 of H1.

The amino acid sequence of the anti-ED-A antibody C8 VL domain (SEQ ID NO: 72) is identical to the amino acid sequence of the VL domain of anti-ED-A antibody H1 except that SEQ ID NO: 76 is substituted for the VL CDR1 of H1.

The amino acid sequence of the anti-ED-A antibody F8 VL domain (SEQ ID NO: 82) is identical to the amino acid sequence of the VL domain of anti-ED-A antibody H1 except that SEQ ID NO: 86 is substituted for the VL CDR1 of H1. The VL domains of the anti-ED-A F8 diabody have the same amino acid sequence as VL domain of the anti-ED-A antibody F8 (i.e. SEQ ID NO: 82).

The amino acid sequence of the anti-ED-A antibody F1 VL domain (SEQ ID NO: 92) is identical to the amino acid sequence of the VL domain of anti-ED-A antibody H1 except that SEQ ID NO: 96 is substituted for the VL CDR1 of H1.

The amino acid sequence of the anti-ED-A antibody B7 VL domain (SEQ ID NO: 102) is identical to the amino acid sequence of the VL domain of anti-ED-A antibody H1 except that SEQ ID NO: 106 is substituted for the VL CDR1 of H1.

The amino acid sequence of the anti-ED-A antibody E8 VL domain (SEQ ID NO: 112) is identical to the amino acid sequence of the VL domain of anti-ED-A antibody H1 except that SEQ ID NO: 116 is substituted for the VL CDR1 of H1.

The amino acid sequence of the anti-ED-A antibody G9 VL domain (SEQ ID NO: 32) is identical to the amino acid sequence of the VL domain of anti-ED-A antibody H1 except that SEQ ID NO: 36 is substituted for the VL CDR1 of H1.

Optionally, the amino acid at position 5 of the VH domain of anti-ED-A antibodies H1, B2, C5, D5, E5, C8, F8, F1, B7, E8, G9 may be a leucine residue (L) rather than a valine residue (V) as shown in FIG. 7A. In addition, or alternatively, the amino acid at position 18 of the VL domain of anti-ED-A antibodies H1, B2, C5, D5, E5, C8, F8, E1, B7, E8, G9 may be an arginine residue (R) rather than a lysine residue (K) as shown in FIG. 7C.

REFERENCES

All references cited anywhere in this specification, including those cited anywhere above, are hereby incorporated by reference in their entirety and for all purposes.

Amit et al. (1986), Science, 233:747-753.
Andersen et al. (2002) Current Opinion in Biotechnology 13: 117
Ausubel et al. (1999) 4*th* eds., *Short Protocols in Molecular Biology: A Compendium of Methods from Current Protocols in Molecular Biology*, John Wiley & Sons.
Bagshawe K. D. et al. (1991) Antibody, Immunoconjugates and Radiopharmaceuticals 4: 915-922
Balza et al. (1988), *FEBS Lett.*, 228: 42-44.
Birchler et al. (1999), J. Immunol. Methods, 231, 239-248.
Bird et al. (1988) Science, 242, 423-426
Borsi et al. (1987), J. Cell. Biol., 104, 595-600.
Borsi et al. (1990), *FEBS Lett.*, 261: 175-178,
Borsi et al. (1995), J. Biol. Chem., 270: 6243-6245.
Borsi et al. (1998), Exp. Cell Res., 240, 244-251.
Brack et al. (2006), Clin. Cancer Res., 12, 3200-3208.
Carnemolla et al. (1989), J. Cell. Biol., 108: 1139-1148.
Caton et al. (1990), J. Immunol., 144:1965-1968.
Chadd et al. (2001), Current Opinion in Biotechnology 12: 188-194
Chothia et al. (1987), J. Mol. Biol., 196:901-917.
Chothia et al. (1989), Nature, 342:877-883.
Devos et al. (1983), Nucl. Acids Res. 11: 4307-4323.
ffrench-Constant (1995), Exp. Cell Res., 221, 261-271.
Giovannoni, Nucleic. Acid Research, 2001, 29(5):E27.
Glennie M J et al., 1987 J. Immunol. 139, 2367-2375
Haan et al. (2004), BioCentury, 12(5): A1-A6.
Hanahan et al. (2000), Cell 100, 57-70.
Harlow and Lane, Antibodies: A Laboratory Manual, Cold Spring Harbor
Kornblihtt et al. (1984), Nucleic Acids Res. 12, 5853-5868. Laboratory, Cold Spring Harbor N.Y., pp. 726, 1988
Heikinheimo et al. (1991), Virchows Arch. B Cell Pathol. Incl. Mol. Pathol., 61, 101-109.
Holliger and Bohlen 1999 Cancer and metastasis rev. 18: 411-419.
Holliger et al. (1993a), Proc. Natl. Acad. Sci. USA 90 6444-6448.
Holliger et al. (1993b), Current Opinion Biotechnol 4, 446-449.
Holt et al. (2003) Trends in Biotechnology 21, 484-490.
Hoogenboom et al. (1991), Nucleic Acids Res., 19 (15) 4133-7.

Hu et al. (1996), Cancer Res., 56, 3055-3061.
Huston et al. (1988) PNAS USA, 85, 5879-5883.
Hynes, R. O. (1990). Fibronectins (New York: Springer-Verlag).
Jacobs et al. (2002), Hum. Pathol., 33, 29-38.
Kabat et al. (1987) Sequences of Proteins of Immunological Interest. 4$^{th}$ Edition. US Department of Health and Human Services.
Kabat et al. (1991a), Sequences of Proteins of Immunological Interest, 5th Edition. US Department of Health and Human Services, Public Service, NIH, Washington. (a)
Kabat et al. (1991b), J. Immunol., 147:1709-1719.
Kaspar et al. (2006), Int. J. Cancer, 118, 1331-1339.
Knappik et al., (2000) J. Mol. Biol. 296, 57-86.
Kohler and Milstein, Nature, 256:495-497, 1975
Koide et al. (1998), Journal of Molecular Biology, 284: 1141-1151.
Kontermann et al. (2001), S, *Antibody Engineering*, Springer-Verlag New York, LLC; ISBN: 3540413545.
Koukoulis et al. (1993), J. Submicrosc. Cytol. Pathol., 25, 285-295.
Koukoulis et al. (1995), Ultrastruct. Pathol., 19, 37-43.
Krebs et al. (2001), Journal of Immunological Methods, 254 67-84.
Larrick J W and Thomas D W (2001) Current Opinion in Biotechnology 12:411-418.
Ledermann J. A. et al. (1991) Int. J. Cancer 47: 659-664
Lohi et al. (1995), Int. J. Cancer, 63, 442-449.
MaED-A et al. (1983) Biochem. Biophys. Res. Comm. 115: 1040-1047;
Matsumoto et al. (1999), Jpn. J. Cancer Res., 90, 320-325.
McCafferty et al. (1990) Nature, 348, 552-554.
Mendez, M. et al., (1997) Nature Genet, 15(2): 146-156.
Merchand et al., 1998 Nature Biotech. 16:677-681
Neri, D., and Bicknell, R. (2005), Nat Rev Cancer 5, 436-446.
Nygren et al. (1997), Current Opinion in Structural Biology, 7: 463-469.
Oyama et al. (1989), J. Biol. Chem., 264, 10331-10334.
Paolella et al. (1988), Nucleic Acids Res. 16, 3545-3557.
Pini et al. (1998), J. Biol. Chem., 273, 21769-21776.
Plückthun (1991), Bio/Technology 9: 545-551.
Reiter et al. (1996), Nature Biotech, 14, 1239-1245.
Repp et al., 1995 J. Hemat. 377-382.
Ridgeway et al. (1996), Protein Eng., 9, 616-621.
Robinson ed., Sustained and Controlled Release Drug Delivery Systems, Marcel Dekker, Inc., New York, 1978
Roesli et al. (2006), Nature Protocols, 1, 192-199.
Ruf et al. (1991) J. Biol. Chem. 226: 15719-15725.
Rybak et al. (2005), Nat. Methods, 2, 291-298.
Rybak et al. (2006), ChemMedChem., 2, 22-40.
Sambrook and Russell, *Molecular Cloning: a Laboratory Manual:* 3rd edition, 2001, Cold Spring Harbor Laboratory Press
Scarpati et al. (1987) Biochemistry 26: 5234-5238.
Scarpino et al. (1999) J. Pathol. 188, 163-167.
Scheurer et al. (2005), Proteomics 5, 3035-3039.
Segal et al. (1974), PNAS, 71:4298-4302.
Sharon et al. (1990a), PNAS, 87:4814-4817.
Sharon et al. (1990b), J. Immunol., 144:4863-4869.
Silacci et al. (2003), Proteomics, 5, 2340-2350.
Staerz U. D. and Bevan M. J. 1986 PNAS 83
Suresh et al., 1986 Method Enzymol. 121: 210-228
Taniguchi et al. (1983) Nature 302, 305-310;
Tavian et al. (1994), Int. J. Cancer, 56, 820-825.
Terrana et al. (1987), Cancer Res. 47, 3791-3797.
Thorpe (2004), Clin. Cancer Res., 10, 415-427.
Trachsel et al. (2006), Adv. Drug Deliv. Rev., 58, 735-754.
Viti et al. (2000), Methods Enzymol., 326, 480-505.
Ward et al. (1989), Nature 341, 544-546.
Wess In: BioCentury, The Bernstein Report on BioBusiness, 12(42), A1-A7, 2004

TABLE 1

Fibronectin peptides identified in normal liver and/or metastasis

| Peptide sequence | Seq. Position | | [1]Liver | [1]Metastasis |
| --- | --- | --- | --- | --- |
| | Start | End | Total = 6 | (Total = 8) |
| HYQINQQWER | 59 | 68 | | 6 |
| VGDTYERPK | 109 | 117 | | 4 |
| HALQSASAGSGSFTDVR | 274 | 290 | | 7 |
| IGDQWDK | 480 | 486 | | 1 |
| TFYQIGDSWEK | 568 | 578 | 1 | |
| WKEATIPGHLNSYTIK | 654 | 669 | | 2 |
| EATIPGHLNSYTIK | 656 | 669 | | 1 |
| GLTPGVIYEGQLISIQQYGHR | 670 | 690 | | 7 |
| WSRPQAPITGYR | 830 | 841 | 2 | 3 |
| SDNVPPPTDLQFVELTDVK | 903 | 921 | | 3 |
| VTIMWTPPDSVVSGYR | 922 | 937 | | 8 |
| VEVLPVSLPGEHGQR | 938 | 952 | | 8 |
| NTFAEITGLSPGVTYLFK | 958 | 975 | | 7 |
| VFAVHQGR | 976 | 983 | | 7 |

TABLE 1-continued

Fibronectin peptides identified in normal liver and/or metastasis

| Peptide sequence | Seq. Position Start | End | [1]Liver (Total = 6) | [1]Metastasis (Total = 8) |
|---|---|---|---|---|
| TVLVTWTPPR | 1011 | 1020 | 2 | 8 |
| QYNVGPLASK | 1040 | 1049 | | 4 |
| NLQPGSEYTVTLVAVK | 1054 | 1069 | | 6 |
| ATGVFTTLQPLR | 1077 | 1088 | 1 | 8 |
| LGVRPSQGGEAPR | 1116 | 1128 | | 7 |
| VVTPLSPPTNLHLEANPDTGVLTVSWER | 1169 | 1196 | | 3 |
| STTPDITGYR | 1197 | 1206 | | 7 |
| VTWAPPPSIELTNLLVR | 1375 | 1391 | 2 | 7 |
| TGLDSPTGFDSSDITANSFTVHWVAPR | 1446 | 1472 | | 4 |
| APITGYIIR | 1473 | 1481 | 1 | 8 |
| HHAEHSVGRPR | 1482 | 1492 | | 1 |
| EESPPLIGQQATVSDIPR | 1525 | 1542 | | 8 |
| ITYGETGGNSPVQEFTVPGSK | 1570 | 1590 | 2 | 8 |
| SPVQEFTVPGSK | 1579 | 1590 | | 6 |
| STATINNIKPGADYTITLYAVTGR | 1591 | 1614 | | 5 |
| GDSPASSKPVSINYK | 1615 | 1629 | | 4 |
| TEIDKPSQMQVTDVQDNSISVR | 1630 | 1651 | | 8 |
| WLPSTSPVTGYR | 1652 | 1663 | | 7 |
| TASPDQTEMTIEGLQPTVEYVVSVYAQNR | 1679 | 1707 | | 7 |
| [2]NGESQPLVQTAVTTIPAPTNLK | 1708 | 1819 | | 3 |
| [3]NGESQPLVQTAVTNIDRPK | 1708 | 1726 | | 1 |
| [3]IAWESPQGQVSR | 1740 | 1751 | | 8 |
| [3]VTYSSPEDGIR | 1754 | 1764 | | 1 |
| FSQVTPTSFTAQWIAPSVQLTGYR | 1820 | 1843 | 1 | 5 |
| YEVSVYALK | 1878 | 1886 | | 2 |
| TKTETITGFQVDAIPANGQTPVQR | 1926 | 1949 | 1 | 2 |
| TETITGFQVDAIPANGQTPVQR | 1928 | 1949 | | 3 |
| SYTITGLQPGTDYK | 1957 | 1970 | | 7 |
| IHLYTLNDNAR | 1971 | 1981 | | 7 |
| SSPVIIDASTAIDAPSNLR | 1982 | 2000 | 3 | 8 |
| FLTTTPNSLLVSWQAPR | 2001 | 2017 | 4 | 5 |
| ITGYIIK | 2020 | 2026 | | 5 |
| YEKPGSPPR | 2027 | 2035 | | 6 |
| [4]PYLPNVDEEVQIGHVPR | 2165 | 2181 | | 7 |

TABLE 1-continued

Fibronectin peptides identified in normal liver and/or metastasis

| Peptide sequence | Seq. Position Start | Seq. Position End | [1]Liver (Total = 6) | [1]Metastasis (Total = 8) |
|---|---|---|---|---|
| GVTYNIIVEALQNQR | 2255 | 2269 | 4 | 7 |
| RPGAAEPSPDGTTGHTYNQYTQR | 2425 | 2447 |  | 2 |

[1]Numbers indicate in how many of the 6 healthy in vivo biotinylated mice or the 8 metastases-bearing in vivo biotinylated mice the peptide was identified in the corresponding tissue samples. All peptides are listed here which had been annotated by the Mascot software to the fibronectin database entries P11276, Q3UHL6 or Q3TCF1.
[2]This pepetide covers a fibronectin sequence portion before AND after the ED-A domain, indicating the presence of an (EDA⁻)-fibronectin isoform.
[3]These peptides match to the sequence of the ED-A domain (Seq. positions 1721-1810).
[4]This peptide matches to the sequence of the IIICS stretch (Seq. positions 2082-2201).

TABLE 2

Nucleotide and amino acid sequences of the heavy chain (VH) and light chain (VL) CDR1s of the anti-ED-A affinity matured antibodies

| Antibody | CDR1 (VH) | CDR1 (VL) |
|---|---|---|
| H1 | CCG CGG AGG<br>P   R   R<br>(SEQ ID NO: 3) | TCT GCG TGG<br>S   A   W<br>(SEQ ID NO: 6) |
| B2 | GCG GCT AAG<br>A   A   K<br>(SEQ ID NO: 23) | GTG GCT TTT<br>V   A   F<br>(SEQ ID NO: 26) |
| C5 | CCG ATT ACT<br>P   I   T<br>(SEQ ID NO: 43) | TTG CAT TTT<br>L   H   F<br>(SEQ ID NO: 46) |
| D5 | GTG ATG AAG<br>V   M   K<br>(SEQ ID NO: 53) | AAT GCT TTT<br>N   A   F<br>(SEQ ID NO: 56) |
| E5 | ACT GGT TCT<br>T   G   S<br>(SEQ ID NO: 63) | CTT GCG CAT<br>L   A   H<br>(SEQ ID NO: 66) |
| C8 | CTT CAG ACT<br>L   Q   T<br>(SEQ ID NO: 73) | CTT CCT TTT<br>L   P   F<br>(SEQ ID NO: 76) |
| F8 | CTG TTT ACG<br>L   F   T<br>(SEQ ID NO: 83) | ATG CCG TTT<br>M   P   F<br>(SEQ ID NO: 86) |
| F1 | TAG GCG CGT<br>Q(Amber) A R<br>(SEQ ID NO: 93) | GCG CCT TTT<br>A   P   F<br>(SEQ ID NO: 96) |
| B7 | CAT TTT GAT<br>H   F   D<br>(SEQ ID NO: 103) | CTG GCT TTT<br>L   A   F<br>(SEQ ID NO: 106) |
| E8 | GAT ATG CAT<br>D   M   H<br>(SEQ ID NO: 113) | TCG TCT TTT<br>S   S   F<br>(SEQ ID NO: 116) |
| G9 | CAT ATG CAG<br>H   M   Q<br>(SEQ ID NO: 33) | ACT GCT TTT<br>T   A   F<br>(SEQ ID NO: 36) |

TABLE 3

BIAcore evaluation data

| Antibody | $k_{on}$ (1/Ms) | $k_{off}$ (1/s) | $K_D$ (M) |
|---|---|---|---|
| Parent anti-ED-A antibody | $2.5 \times 10^5$ | 0.02 | $\sim 1 \times 10^{-7}$ |
| B2 | $3.8 \times 10^5$ | $7.54 \times 10^{-3}$ | $\sim 2 \times 10^{-8}$ |
| C5 | $3.04 \times 10^5$ | $9.23 \times 10^{-3}$ | $\sim 3 \times 10^{-8}$ |
| D5 | $4.53 \times 10^5$ | $7.6 \times 10^{-3}$ | $\sim 1.7 \times 10^{-8}$ |
| C8 | $3.8 \times 10^5$ | $5.3 \times 10^{-3}$ | $\sim 1.4 \times 10^{-8}$ |
| F8 | $4.65 \times 10^5$ | $1.4 \times 10^{-3}$ | $\sim 3.1 \times 10^{-9}$ |
| B7 | $2.67 \times 10^5$ | $4.5 \times 10^{-3}$ | $\sim 1.68 \times 10^{-8}$ |
| G9 | $3.6 \times 10^5$ | $7.54 \times 10^{-3}$ | $\sim 2.09 \times 10^{-8}$ |

The invention claimed is:

1. A method of delivering a molecule to the neovasculature of tumour metastases in a human or animal comprising administering to the human or animal an antibody which binds the ED-A isoform of fibronectin comprising:
 a VH domain comprising a framework and a set of complementarity determining regions HCDR1, HCDR2 and HCDR3, wherein:
  HCDR1 has the amino acid sequence of SEQ ID NO:83,
  HCDR2 has the amino acid sequence of SEQ ID NO: 4, and
  HCDR3 has the amino acid sequence of SEQ ID NO: 5, and
 a VL domain comprising a framework and a set of complementarity determining regions LCDR1, LCDR2 and LCDR3, wherein:
  LCDR1 has the amino acid sequence of SEQ ID NO:86,
  LCDR2 has the amino acid sequence of SEQ ID NO: 7, and
  LCDR3 has the amino acid sequence of SEQ ID NO: 8;
 wherein the antibody is conjugated to the molecule.

2. The method of claim 1, wherein the antibody binds the ED-A of fibronectin.

3. The method of claim 1, wherein the molecule is a detectable label, a radioisotope, and/or has biocidal or cytotoxic activity.

4. The method of claim 1, wherein the VH domain framework is a human germline framework.

5. The method of claim 4, wherein the VH domain has the amino acid sequence of SEQ ID NO: 81.

6. The method of claim 1, wherein the VL domain framework is a human germline framework.

7. The method of claim 6, wherein the VL domain has the amino acid sequence of SEQ ID NO:82.

8. The method of claim 1, wherein the antibody is a single chain Fv.

9. The method of claim 1, wherein the antibody is a diabody.

10. The method of claim 1, wherein the antibody comprises:
 a VH domain comprising a set of complementarity determining regions HCDR1, HCDR2 and HCDR3 and a framework, wherein HCDR1 has the amino acid sequence of SEQ ID NO: 83, HCDR2 has the amino acid sequence of SEQ ID NO: 4, and HCDR3 has the amino acid sequence of SEQ ID NO: 5; and
 a VL domain comprising a set of complementarity determining regions LCDR1, LCDR2 and LCDR3 and a framework, wherein LCDR1 has the amino acid sequence of SEQ ID NO: 86, LCDR2 has the amino acid sequence of SEQ ID NO: 7, and LCDR3 has the amino acid sequence of SEQ ID NO: 8.

11. The method of claim 1, wherein the antibody comprises a VH domain having the amino acid sequence of SEQ ID NO: 81 and a VL domain having the amino acid sequence of SEQ ID NO: 82.

* * * * *